(12) United States Patent
Cheng et al.

(10) Patent No.: US 7,393,671 B2
(45) Date of Patent: Jul. 1, 2008

(54) MUTANT CAROTENOID KETOLASES

(75) Inventors: Qiong Cheng, Wilmington, DE (US); Luan Tao, Haverstown, PA (US)

(73) Assignee: E.I. du Pont de Nemours and Company, Wimington, DE (US)

( * ) Notice: Subject to any disclaimer, the term of this patent is extended or adjusted under 35 U.S.C. 154(b) by 0 days.

(21) Appl. No.: 11/393,082

(22) Filed: Mar. 30, 2006

(65) Prior Publication Data

US 2007/0238149 A1 Oct. 11, 2007

(51) Int. Cl.
*C12P 23/00* (2006.01)
*C12N 5/10* (2006.01)
*C12N 1/21* (2006.01)
*C12N 15/00* (2006.01)
*C12N 5/14* (2006.01)
*C12N 1/12* (2006.01)
*C12N 1/11* (2006.01)
*C12N 1/13* (2006.01)
*C12N 1/15* (2006.01)
*C12N 1/19* (2006.01)
*C07H 21/00* (2006.01)
*C12N 9/02* (2006.01)
*C12P 21/00* (2006.01)
*C07K 14/00* (2006.01)

(52) U.S. Cl. ............... 435/189; 435/325; 435/252.3; 435/252.31; 435/252.32; 435/252.33; 435/252.34; 435/252.35; 435/69.1; 435/410; 435/254.11; 435/257.2; 435/254.2; 435/254.3; 435/254.6; 435/254.21; 435/254.23; 435/254.22; 435/67; 435/320.1; 536/23.2; 530/350

(58) Field of Classification Search . 435/252.3–252.35, 435/325, 189, 69.1, 410, 254.11, 257.2, 254.2, 435/254.3, 254.6, 254.21, 254.23, 254.22; 536/23.2; 530/350
See application file for complete search history.

(56) References Cited

U.S. PATENT DOCUMENTS

| 6,150,130 | A | 11/2000 | Misawa et al. |
| 6,291,204 | B1 * | 9/2001 | Pasamontes et al. ......... 435/67 |
| 2003/0087337 | A1 | 5/2003 | Giraud et al. |
| 2005/0227311 | A1 | 10/2005 | Cheng et al. |

FOREIGN PATENT DOCUMENTS

| WO | WO 01/94418 | A2 | 12/2001 |
| WO | WO 02/079395 | A2 | 10/2002 |
| WO | WO 2005/062867 | A2 | 7/2005 |
| WO | WO 2005/118812 | A1 | 12/2005 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Nakamura et al., GenBank accession No. BAC89669, 2003.*
Nakamura et al., GenBank accession No. AP006574, 2003.*
Kappel et al., Current Opinion in Biotechnology 3:548-553, 1992.*
Mullins et al., Hypertension 22(4):630-633, 1993.*
Mullins et al., J. Clin. Invest. 97(7):1557-1560, 1996.*
Wigley et al., Reprod. Fert. Dev. 6:585-588, 1994.*
Cameron, E., Molecular Biotechnology 7:253-265, 1997.*
U.S. Appl. No. 11/015,433, filed Dec. 17, 2004, Cheng et al.
H. J. Nelis et al., Carotenoids From Micro-Organisms, The Journal of Applied Bacteriology, vol. 70:181-191, 1991.
Norihiko Misawa et al., Structure and Functional Analysis of a Marine Bacterial Carotenoid Biosynthesis Gene Cluster and Astaxanthin Biosynthetic Pathway Proposed at the Gene Level, Journal of Bacteriology, vol. 177(22):6575-6584, 1995.
Norihiko Misawa et al., Metabolic Engineering for the Production of Carotenoids in Non-Carotenogenic Bacteria and Yeasts, Journal of Biotechnology, vol. 59:169-181, 1998.
Laure Hannibal et al., Isolation and Chacterization of Canthaxanthin Biosynthesis Genes From the Photosynthetic Bacterium *Bradyrhizobium* sp. Strain ORS278, Journal of Bacteriology, vol. 182(13):3850-3853, 2000.
Blanca Fernandez-Gonzalez et al., A New Type of Asymmetrically Acting Beta-Carotene Ketolase is Required for the Synthesis of Echinenone in the Cyanobacterium *Synechocystis* sp. PCC 6803, The Journal of Biological Chemistry, vol. 272(15):9728-9733, 1997.
Yasuhiro Nishida et al., Elucidation of a Carotenoid Biosynthesis Gene Cluster Encoding a Novel Enzyme, 2,2'-Beta-Hydroxylase, From *Brevundimonas* sp. Strain SD212 and Combinatorial Biosynthesis of New or Rare Xanthophylls, Applied and Environmental Microbiology, vol. 71(8):4286-4296, 2005.
National Center for Biotechnology Information General Identifier No. 5912292, Accession No. CAB56059, Sep. 15, 1999, M. Harker et al., Carotenoid Biosynthesis Genes in the Bacterium *Paracoccus marcusii* MH1.
Tao et al., Engineering A B-Carotene Ketolase for Astaxanthin Production, Metabolic Engineering, 2006, vol. 8:523-531.
International Search Report Dated Aug. 10, 2007, International Application No. PCT/US2007/006930, International Filing Date: Mar. 20, 2007.

* cited by examiner

*Primary Examiner*—Delia M Ramirez

(57) ABSTRACT

CrtW carotenoid ketolases are provided that are useful for the production of astaxanthin and other cyclic ketocarotenoids. The mutant ketolase genes of the present invention encode polypeptides characterized by an improvement in astaxanthin synthesis activity when converting cyclic hydroxylated carotenoid intermediates into astaxanthin. Expression of the mutant carotenoid ketolases in heterologous hosts enabled increased production of astaxanthin relative to the *Sphingomonas melonis* DC18 CrtW.

11 Claims, 1 Drawing Sheet

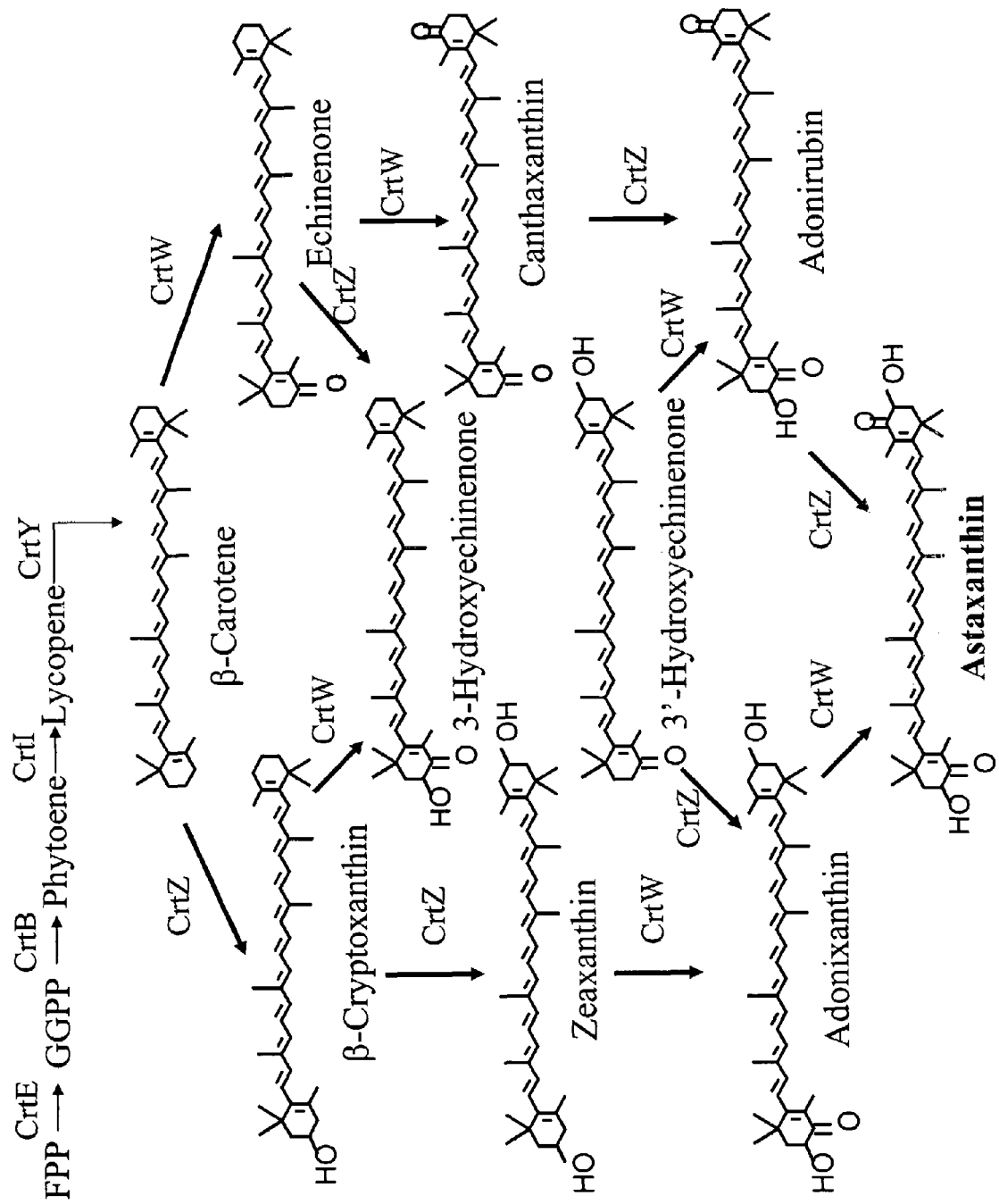

MUTANT CAROTENOID KETOLASES

FIELD OF THE INVENTION

This invention is in the field of microbiology and molecular biology. More specifically, this invention pertains to nucleic acid fragments encoding polypeptides having carotenoid ketolase activity useful for synthesizing astaxanthin.

BACKGROUND OF THE INVENTION

Carotenoids are pigments that are ubiquitous throughout nature and synthesized by all photosynthetic organisms, and in some heterotrophic growing bacteria and fungi. Carotenoids provide color for flowers, vegetables, insects, fish and birds. Colors of carotenoid range from yellow to red with variations of brown and purple. As precursors of vitamin A, carotenoids are fundamental components in our diet and they play additional important role in human health. Because animals are unable to synthesize carotenoid de novo, they must obtain them by dietary means. Thus, manipulation of carotenoid production and composition in plants or bacteria can provide new or improved source for carotenoids. Industrial uses of carotenoids include pharmaceuticals, food supplements, animal feed additives, and colorants in cosmetics, to mention a few.

Industrially, only a few carotenoids are used for food colors, animal feeds, pharmaceuticals, and cosmetics, despite the existence of more than 600 different carotenoids identified in nature. This is largely due to difficulties in production. Presently, most of the carotenoids used for industrial purposes are produced by chemical synthesis; however, these compounds are very difficult to make chemically (Nelis and Leenheer, *Appl. Bacteriol.*, 70:181-191 (1991)). Natural carotenoids can either be obtained by extraction of plant material or by microbial synthesis; but, only a few plants are widely used for commercial carotenoid production and the productivity of carotenoid synthesis in these plants is relatively low. As a result, carotenoids produced from these plants are very expensive. One way to increase the productive capacity of biosynthesis would be to apply recombinant DNA technology (reviewed in Misawa and Shimada, *J. Biotech.*, 59:169-181 (1998)). Thus, it would be desirable to produce carotenoids in non-carotenogenic bacteria and yeasts, thereby permitting control over quality, quantity, and selection of the most suitable and efficient producer organisms. The latter is especially important for commercial production economics (and therefore availability) to consumers.

Carotenoid ketolases are a class of enzymes that introduce keto groups to the ionone ring of the cyclic carotenoids, such as β-carotene, to produce ketocarotenoids. Examples of ketocarotenoids include astaxanthin, canthaxanthin, adonixanthin, adonirubin, echinenone, 3-hydroxyechinenone, 3'-hydroxyechinenone, 4-keto-gamma-carotene, 4-keto-rubixanthin, 4-keto-torulene, 3-hydroxy-4-keto-torulene, deoxyflexixanthin, and myxobactone. Two classes of ketolase, CrtW and CrtO, have been reported. The two classes have similar functionality yet appear to have arisen independently as they share very little sequence similarity. The CrtW is a symmetrically acting enzyme that adds keto-groups to both rings of D-carotene (Hannibal et al., *J. Bacteriol.*, 182: 3850-3853 (2000)). Fernández-González et al. (*J. of Biol. Chem.*, 272: 9728-9733 (1997)) reported that the CrtO ketolase enzyme from *Synechocystis* sp. PCC6803 adds a keto-group asymmetrically to only one of the two β-ionone rings of β-carotene.

Several examples of CrtW ketolases have been reported in variety of microorganisms including *Agrobacterium aurantiacum* (also known as *Paracoccus* sp. N81106; U.S. Pat. No. 6,150,130; Misawa et al., *Biochem. Biophys. Res. Comm.*, 209(3):867-876 (1995); and Misawa et al., *J. Bacteriol.*, 177 (2):6575-6584 (1995)), *Bradyrhizobium* sp. (US Patent Publication No. 20030087337; Hannibal et al., *J. Bactetiol.*, 182 (13):3850-3853 (2000)), *Brevundimonas aurantiacum* (de Souza et al., WO 02/079395), *Brevundimonas* sp. SD212 (WO2005/118812 A1 and Nishida et al., *Appl. Env. Microbiol.*, 71(8):42864296 (2005), *Paracoccus marcusii* (Harker, M. and Hirschberg, N., (GenBank® CAB56059), *Alcaligenes* sp. (Misawa et al., 1995 (supra)), *Sphingomonas melonis* DC18 (U.S. Ser. No. 11/015,433), *Brevundimonas vesicularis* (U.S. Ser. No. 11/015,433), and *Flavobacterium* sp. (U.S. Ser. No. 11/015,433).

One factor influencing the economics of recombinant microbial production of astaxanthin is the enzymatic activity when introducing keto groups to the β-ionone rings of β-carotene and the various cyclic hydroxylated intermediates involved in the production of astaxanthin (FIG. 1). Many CrtW ketolases efficiently introduce keto groups to β-carotene, forming ketocarotenoids such as canthaxanthin. Production of astaxanthin requires the addition of hydroxyl groups to the ionone rings. This is typically accomplished by coexpressing at least one CrtZ hydroylase in combination with the CrtW ketolase. Recombinant expression of crtWZ genes in host cells capable of producing β-carotene typically results in a mixture of astaxanthin and various cyclic hydroxylated intermediates (e.g., zeaxanthin and adonixanthin). However, most CrtW ketolases exhibit limited activity towards these cyclic hydroxylated carotenoid intermediates. The limited activity adversely affects astaxathin production (as measured by the percentage of astaxanthin produced relative to the total carotenoid content).

Recombinant expression of the *Sphingomonas melonis* DC18 CrtW ketolase in an β-carotene producing microbial host cell produced essentially 100% canthaxanthin (U.S. Ser. No. 11/015,433). However, expression of the DC18 CrtW ketolase gene in a host cell capable of producing zeaxanthin results in the limited production of astaxanthin (12-14% of the total carotenoid concentration) with the majority (about 85%) of the carotenoids in the host cell being unwanted cyclic hydroxylated carotenoid intermediates (i.e., adonixanthin and zeaxanthin).

The problem to be solved therefore is to provide CrtW ketolases characterized by improved activity for converting cyclic hydroxylated intermediates into astaxanthin.

SUMMARY OF THE INVENTION

Mutant CrtW ketolases are provided having an improved ability to convert cyclic hydroxylated carotenoid intermediates into astaxanthin. More specifically, mutant ketolases derived from the *Sphingomonas melonis* DC18 CrtW ketolase are provided having significantly improved astaxanthin synthesis activity.

In one embodiment, the invention provides a n isolated nucleic acid molecule encoding a polypeptide having carotenoid ketolase activity, said polypeptide comprising the amino acid as set forth in SEQ ID NO: 3 and further comprising at least one mutation selected from the group consisting of:

a) a mutation at amino acid position 96 changing histidine to leucine;

b) a mutation at amino acid position 203 changing arginine to tryptophan;

c) a mutations a amino acid position 205 changing alanine to valine;

d) a mutation at amino acid position 208 changing alaine to valine;

e) a mutation at amino acid position 213 changing phenylalanine to leucine; and f) a mutation at amino acid position 215 changing alanine to threonine.

Preferred embodiments of the invention include isolated nucleic acid molecules encoding mutant ketolase enzymes having at least a 2,4-fold improvement in ketolase activity for converting cyclic hydroxylated carotenoid intermediates into astaxanthin when compared to the ketolase activity of the Sphingomonas melonis DC18 CrtW ketolase under identical reaction conditions.

In another embodiment, the isolated nucleic acid fragment encodes a polypeptide having an amino acid sequence selected from the group consisting of SEQ ID NOs: 18, 20, 28, 30, 36, 38, 40, 42, 44, 46, 50, 52, 54, 56, 58, 62, 64, 66, 68, 70, 72, 72, and 78.

An yet another embodiment, the isolated nucleic acid fragment has a nucleic acid sequence selected from the group consisting of SEQ ID NOs: 17, 19, 21, 22, 23, 24, 25, 26, 27, 29, 31, 32, 33, 34, 35, 37, 39, 41, 43, 45, 47, 48, 49, 51, 53, 55, 57, 59, 60, 61, 63, 65, 67, 69, 71, 73, 77, and 81.

In still yet another embodiment, the isolated nucleic acid fragment has a nucleic acid sequence comprising nucleic acid residues. 32 through 778 from any one of SEQ ID NOs: 17, 19, 21, 22, 23, 24, 25, 26, 27, 29, 31, 32, 33, 34, 35, 37, 39, 41, 43, 45, 47, 48, 49, 51, 53, 55, 57, 59, 60, 61, 63, 65, 67, 69, 71, 73, 77, and 81.

In a further embodiment, the isolated nucleic acid fragment includes the a28t mutant ribosomal binding site comprising nucleic acid residues 19-31 of SEQ ID NO: 17.

In another embodiment the invention provides a method for the production of cyclic a ketocarotenoid compound comprising:

(a) providing a host cell that produces a cyclic hydroxylated carotenoid compound selected from the group consisting of β-cryptoxanthin, 3-hydroxyechinenone, 3'-hydroxyechinenone, zeaxanthin, and adonixanthin;

(b) transforming the host cell of (a) with the nucleic acid molecule of the invention operably linked to suitable regulatory sequences; and (c) growing the transformed host cell of (b) under conditions whereby a cyclic ketocarotenoid compound is produced.

BRIEF DESCRIPTION OF THE FIGURE AND SEQUENCE DESCRIPTIONS

FIG. 1. Illustration of possible pathway intermediates in the synthesis of astaxanthin via ketolase and hydroxylase reactions from β-carotene.

The invention can be more fully understood from the following detailed description and the accompanying sequence descriptions, which form a part of this application.

The following sequences comply with 37 C.F.R. 1.821-1.825 ("Requirements for patent applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822.

A Sequence Listing is provided herewith on Compact Disk. The contents of the Compact Disk containing the Sequence Listing are hereby incorporated by reference in compliance with 37 CFR 1.52(e). The Compact Discs are submitted in duplicate and are identical to one another. The discs are labeled "Copy 1 Sequence Listing" and "Copy 2 Sequence listing" The discs contain the following file: CL3329 US NA.ST25 having the following size: 198,000 bytes and which was created Jun. 5, 2006.

SEQ ID NO: 1 is the nucleotide sequence of the Sphingomonas melonis DC18 16S rRNA gene.

SEQ ID NO: 2 is the nucleotide sequence of the Sphingomonas melonis DC18 crtW ORF.

SEQ ID NO: 3 is the deduced amino acid sequence of the Sphingomonas melonis DC18 CrtW ketolase.

SEQ ID NO: 4 is the nucleotide sequence of plasmid pDCQ330.

SEQ ID NO: 5 is the nucleotide sequence of primer crtW-18_F2

SEQ ID NO: 6 is the nucleotide sequence of primer crtW-18_R2

SEQ ID NO: 7 is the nucleotide sequence of plasmid pDCQ395.

SEQ ID NO: 8 is the nucleotide sequence of the crtZ carotenoid hydroxylase gene from Pantoea agglomerans DC404 (U.S. Pat. No. 6,929,928).

SEQ ID NO: 9 is the deduced amino acid sequence of the CrtZ carotenoid hydroxylase gene from Pantoea agglomerans DC404 (U.S. Pat. No. 6,929,928).

SEQ ID NO: 10 is the nucleotide sequence of primer crt404ZF.

SEQ ID NO: 11 is the nucleotide sequence of primer crt404ZR.

SEQ ID NO: 12 is the nucleotide sequence of primer ptrc-35C-F.

SEQ ID NO: 13 is the nucleotide sequence of primer ptrc-35C-R

SEQ ID NO: 14 is the nucleotide sequence of the NcoI-EcoRI fragment from plasmid pDCQ351 M. The nucleic acid molecule comprises the ORF for the crtW ketolase and 5' and 3' flanking regions. The 5' flanking region comprises the wild type ribosomal binding sequence (nucleic acid residues 19-31).

SEQ ID NO: 15 is the nucleotide sequence of primer pTrcHis2-FF.

SEQ ID NO: 16 is the nucleotide sequence of primer pTrcHis2-RR.

SEQ ID NO: 17 is the nucleotide sequence of the mutant crtW gene "MM1". The nucleic acid molecule comprises the ORF of the mutant MM1 ketolase and 5' and 3' flanking regions. The 5' flanking region comprises the mutant ribosomal binding site (nucleic acid residues 19 through 31) having a mutation comprising an a28t substitution.

SEQ ID NO: 18 is the deduced amino acid sequence of the mutant crtW gene "MM1".

SEQ ID NO: 19 is the nucleotide sequence of CrtW mutant #1.

SEQ ID NO: 20 is the deduced amino acid sequence of CrtW mutants 1 through 7.

SEQ ID NO: 21 is the nucleotide sequence of CrtW mutant #2.

SEQ ID NO: 22 is the nucleotide sequence of CrtW mutant #3.

SEQ ID NO: 23 is the nucleotide sequence of CrtW mutant #4.

SEQ ID NO: 24 is the nucleotide sequence of CrtW mutant #5.

SEQ ID NO: 25 is the nucleotide sequence of CrtW mutant #6.

SEQ ID NO: 26 is the nucleotide sequence of CrtW mutant #7.

SEQ ID NO: 27 is the nucleotide sequence of CrtW mutant #8.

SEQ ID NO: 28 is the deduced amino acid sequence of CrtW mutant #8.

SEQ ID NO: 29 is the nucleotide sequence of CrtW mutant #9.

SEQ ID NO: 30 is the deduced amino acid sequence of CrtW mutants 9 through 13.

SEQ ID NO: 31 is the nucleotide sequence of CrtW mutant #10.

SEQ ID NO: 32 is the nucleotide sequence of CrtW mutant #11.

SEQ ID NO: 33 is the nucleotide sequence of CrtW mutant #12.

SEQ ID NO: 34 is the nucleotide sequence of CrtW mutant #13.

SEQ ID NO: 35 is the nucleotide sequence of CrtW mutant #14.

SEQ ID NO: 36 is the deduced amino acid sequence of CrtW mutant #14.

SEQ ID NO: 37 is the nucleotide sequence of CrtW mutant #15.

SEQ ID NO: 38 is the deduced amino acid sequence of CrtW mutant #15.

SEQ ID NO: 39 is the nucleotide sequence of CrtW mutant #16.

SEQ ID NO: 40 is the deduced amino acid sequence of CrtW mutant #16.

SEQ ID NO: 41 is the nucleotide sequence of CrtW mutant #17.

SEQ ID NO: 42 is the deduced amino acid sequence of CrtW mutant #17 and the mutant having SEQ ID NO: 83.

SEQ ID NO: 43 is the nucleotide sequence of CrtW mutant #18.

SEQ ID NO: 44 is the deduced amino acid sequence of CrtW mutant #18.

SEQ ID NO: 45 is the nucleotide sequence of CrtW mutant #19.

SEQ ID NO: 46 is the deduced amino acid sequence of CrtW mutants 19 through 21.

SEQ ID NO: 47 is the nucleotide sequence of CrtW mutant #20.

SEQ ID NO: 48 is the nucleotide sequence CrtW mutant #21.

SEQ ID NO: 49 is the nucleotide sequence of CrtW mutant #22.

SEQ ID NO: 50 is the deduced amino acid sequence of CrtW mutant #22.

SEQ ID NO: 51 is the nucleotide sequence of CrtW mutant #23.

SEQ ID NO: 52 is the deduced amino acid sequence of CrtW mutant #23.

SEQ ID NO: 53 is the nucleotide sequence of CrtW mutant #24.

SEQ ID NO: 54 is the deduced amino acid sequence of CrtW mutant #24.

SEQ ID NO: 55 is the nucleotide sequence of CrtW mutant #25.

SEQ ID NO: 56 is the deduced amino acid sequence of CrtW mutant #25.

SEQ ID NO: 57 is the nucleotide sequence of CrtW mutant #26.

SEQ ID NO: 58 is the deduced amino acid sequence of CrtW mutants 26 through 28.

SEQ ID NO: 59 is the nucleotide sequence of CrtW mutant #27.

SEQ ID NO: 60 is the nucleotide sequence of CrtW mutant #28.

SEQ ID NO: 61 is the nucleotide sequence of CrtW mutant #29.

SEQ ID NO: 62 is the deduced amino acid sequence of CrtW mutant #29.

SEQ ID NO: 63 is the nucleotide sequence of CrtW mutant #30.

SEQ ID NO: 64 is the deduced amino acid sequence of CrtW mutant #30.

SEQ ID NO: 65 is the nucleotide sequence of CrtW mutant #31.

SEQ ID NO: 66 is the deduced amino acid sequence of CrtW mutant #31.

SEQ ID NO: 67 is the nucleotide sequence of CrtW mutant #32.

SEQ ID NO: 68 is the deduced amino acid sequence of CrtW mutant #32.

SEQ ID NO: 69 is the nucleotide sequence of CrtW mutant #33.

SEQ ID NO: 70 is the deduced amino acid sequence of CrtW mutant #33.

SEQ ID NO: 71 is the nucleotide sequence of CrtW mutant #35.

SEQ ID NO: 72 is the deduced amino acid sequence of CrtW mutant #35.

SEQ ID NO: 73 is the nucleotide sequence of CrtW mutant #36.

SEQ ID NO: 74 is the deduced amino acid sequence of CrtW mutant #36.

SEQ ID NO: 75 is the nucleotide sequence of the first primer used to make an F213L and R203W double mutant.

SEQ ID NO: 76 is the nucleotide sequence of the second primer used to make an F213L and R203W double mutant.

SEQ ID NO: 77 is the nucleotide sequence of an NcoI-EcoRI fragment comprising the R203W/F213L double mutant on plasmid pDCQ425.

SEQ ID NO: 78 is the deduced amino acid sequence of the CrtW double mutant R203W/F213L.

SEQ ID NO: 79 is the nucleotide sequence of the first primer used to introduce a mutant ribosomal binding sequence to a mutant #17.

SEQ ID NO: 80 is the nucleotide sequence of the second primer used to introduce a mutant ribosomal binding sequence to mutant #17.

SEQ ID NO: 81 is the nucleotide sequence of an NcoI-EcoRI fragment comprising mutant #17 with a mutant ribosomal binding site.

DETAILED DESCRIPTION OF THE INVENTION

The present mutant crtW genes and their expression products, polypeptides having improved carotenoid ketolase activity (E.C. 1.13.-.-), are useful for the creation of recombinant organisms that have the ability to produce astaxanthin. A nucleic acid fragment encoding the CrtW ketolase from *Sphingomonas melonis* DC18 (U.S. Ser. No. 11/015,433; herein incorporated by reference) was isolated and subjected to, random mutagenesis. The resulting library of mutants were screened for improved conversion of cyclic hydroxylated cyclic carotenoid intermediates into astaxanthin. The present nucleic acid fragments reported herein exhibit a significant improved (at least 2,4-fold) in carotenoid ketolase activity when converting hydroyxlated carotenoids into astaxanthin.

The present mutant crtW ketolase genes were expressed in transgenic microbial hosts engineered to produce suitable substrates (i.e., zeaxanthin and other cyclic hydroxylated intermediates). Functional expression of the mutant genes was measured by the production of astaxanthin in the heterologous hosts expressing a zeaxanthin reporter plasmid. Improvements in carotenoid ketolase activity were measured relative to the wild type CrtW ketolase from *Sphingomonas melonis* DC18 (U.S. Ser. No. 11/015,433). Additionally, a mutation in the ribosomal binding site of the wild type trc promoter was also identified that further enhanced astaxanthin production.

The genes and gene products of the present invention may be used in a variety of ways for the production or regulation of astaxanthin biosynthesis. The present mutant crtW ketolase genes can be expressed in a variety of heterologous hosts having the ability to produce suitable substrates.

The gene and gene sequences described herein enable one to increase the production and/or percent conversion (relative to the total carotenoid content of the cell) of astaxanthin in an recombinant host cell. This aspect makes any recombinant host into which these genes are incorporated a more desirable production host. The astaxanthin produced can be isolated from the production host for use in a variety of applications, including animal feed. Optionally, the recombinant host cells (whole, homogenized, or autolysed) can be directly incorporated into animal feed. Salmon and shrimp aquacultures are particularly useful applications for this invention as carotenoid pigmentation is critically important for the value of these organisms (Shahidi, F. and Brown, J. A., *Critical Reviews in Food Science*, 38(1):1-67 (1998)).

In this disclosure, a number of terms and abbreviations are used. The following definitions are provided.

As used herein, the term "comprising" means the presence of the stated features, integers, steps, or components as referred to in the claims, but that it does not preclude the presence or addition of one or more other features, integers, steps, components or groups thereof.

The term "invention" or "present invention" as used herein is not meant to be limited to any specific embodiment of the invention but applies to all embodiments and variations encompassed by the claims and the specification.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

"Open reading frame" is abbreviated ORF.

"Polymerase chain reaction" is abbreviated PCR.

As used herein, the terms "isolated nucleic acid molecule" and "isolated nucleic acid fragment" will be used interchangeably and will mean a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

As used herein, the term "pDCQ330" refers to a β-carotene producing plasmid. The plasmid was constructed by cloning the crtEidiYIB carotenoid gene cluster from *Pantoea agglomerans* DC404 into broad host range vector pBHR1 (U.S. Pat. No. 6,929,928 and U.S. Ser. No. 11/015,433; each herein incorporated by reference).

As used herein, the term "pDCQ395" refers to a zeaxanthin producing plasmid. The plasmid was constructed by cloning the crtZ from *Pantoea agglomerans* DC404 upstream of the crtEidiYIB carotenoid gene cluster on pDCQ330.

As used herein, the term "isoprenoid" or "terpenoid" refers to the compounds are any molecule derived from the isoprenoid pathway including 10 carbon terpenoids and their derivatives, such as carotenoids and xanthophylls.

As used herein, the term "carotenoid" refers to a compound composed of a polyene backbone which is condensed from five-carbon isoprene unit. Carotenoids can be acyclic or terminated with one (monocyclic) or two (bicyclic) cyclic end groups. The term "carotenoid" may include both carotenes and xanthophylls. A "carotene" refers to a hydrocarbon carotenoid. Carotene derivatives that contain one or more oxygen atoms, in the form of hydroxy-, methoxy-, oxo-, epoxy-, carboxy-, or aldehydic functional groups, or within glycosides, glycoside esters, or sulfates, are collectively known as "xanthophylls". The present ketolases exhibit an improvement in activity for converting cyclic hydroxylated carotenoid intermediates into astaxanthin.

As used herein, the terms "cyclic hydroxylated carotenoid", "cyclic hydroxylated carotenoid intermediate", and "cyclic hydroxylated substrate" refers to C40 carontenoids derived from β-carotene having at least one hydroxyl group on the β-ionone ring. Carotenoid hydroxylases (e.g, CrtZ) and carotenoid ketolases (e.g., CrtW) are enzymes that typically accept a variety of carotenoid substrates in the biosynthetic pathway from β-carotene to astaxanthin, although the activity towards each substrate varies (FIG. 1). In one embodiment, the cyclic hydroxylated intermediates in the biosynthetic pathway to astaxanthin include, but are not limited to β-cryptoxanthin, 3-hydroxyechinenone, 3'-hydroxyechinenone, zeaxanthin, and adonixanthin. The present mutant CrtW ketolases exhibit an improved activity for converting cyclic hydroxylated carotenoid intermediates into astaxanthin. In a preferred embodiment, the present mutant CrtW ketolases exhibit an improved activity for converting zeaxanthin and/or adonixanthin to astaxanthin.

As used herein, the term "carotenoid biosynthetic pathway" refers to those genes comprising members of the "upper isoprenoid pathway" and/or the "lower carotenoid biosynthetic pathway".

As used herein, the terms "upper isoprenoid pathway" and "upper pathway" are used interchangeably and refer to enzymes involved in converting pyruvate and glyceraldehyde-3-phosphate to farnesyl pyrophosphate (FPP). Genes encoding these enzymes include, but are not limited to: the "dxs" gene (encoding 1-deoxyxylulose-5-phosphate synthase); the "dxr" gene (encoding 1-deoxyxylulose-5-phosphate reductoisomerase; also known as the ispC); the "ispD" gene (encoding a 2C-methyl-D-erythritol cytidyltransferase enzyme; also known as ygbP); the "ispE" gene (encoding 4-diphosphocytidyl-2-C-methylerythritol kinase; also known as ychB); the "ispF" gene (encoding a 2C-methyl-D-erythritol 2,4-cyclodiphosphate synthase; also known as ygbB); the "pyrg" gene (encoding a CTP synthase; also known as ispF); the "lytB" gene (also known as ispH)

involved in the formation of dimethylallyl diphosphate; the "gcpE" gene (also known as ispG) involved in the synthesis of 2-C-methyl-D-erythritol 4-phosphate; the "idi" gene (responsible for the intramolecular conversion of IPP to dimethylallyl pyrophosphate); and the "ispA" gene (encoding geranyltransferase or farnesyl diphosphate synthase) in the isoprenoid pathway.

As used herein, the terms "lower carotenoid biosynthetic pathway" and "lower pathway" will be used interchangeably and refer to those enzymes which convert FPP to astaxanthin. These genes and gene products comprise all of the "crt" genes including, but not limited to: crtE, crtY, crtI, crtB, crtZ, and crtW. Finally, the term "lower carotenoid biosynthetic enzyme" is an inclusive term referring to any and all of the enzymes in the lower pathway involved in the biosynthesis of astaxanthin including, but not limited to: CrtE, CrtY, CrtI, CrtB, CrtZ, and CrtW.

As used herein, the term "CrtZ" refers to a β-carotene hydroxylase enzyme encoded by the crtZ gene, which catalyzes a hydroxylation reaction from β-carotene to zeaxanthin.

As used herein, the term "CrtW" refers to a β-carotene ketolase enzyme capable of catalyzing an oxidation reaction where a keto group is introduced on the ionone ring of cyclic carotenoids. It is known that CrtW ketolases typically exhibit some substrate flexibility. As used herein, the term "carotenoid ketolase" or "β-carotene ketolase" or "ketolase" refers to the CrtW-type ketolases that can add keto groups to the β-ionone ring of cyclic carotenoids.

As used herein, the term "keto group" or "ketone group" will be used interchangeably and refers to a group in which a carbonyl group is bonded to two carbon atoms: $R_2C=O$ (neither R may be H).

As used herein, the term "ketocarotenoid" refers to carotenoids possessing at least one keto group on the ionone ring of a cyclic carotenoid. Examples of ketocarotenoids include, but are not limited to canthaxanthin and astaxanthin.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes the amino acid sequence for the present mutant CrtW ketolases. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. As used herein, the term "native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. As shown in the present sequence listing, the coding sequence within the provided NcoI-EcoRI fragments typically includes nucleotide 32 through 778 (corresponding to nucleotides 443 through 1189 on plasmid pDCQ351 M).

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing sites, ribosomal binding sites, effector binding sites, and stem-loop structures, to name a few.

As used herein, the terms "mutant ribososmal binding site", "mutant ribosomal binding sequence", and "mutant Shine-Dalgarno sequence" refer to any nucleotide mutation to the wild type ribosomal binding site and the flanking sequence for the Sphingomonas melonis DC18 crtW gene (aggaggaataaac; nucleic acid residues 19-31 of SEQ ID NO: 14). The present mutant ribosomal binding site enhances astaxanthin production in the present mutants. Specifically, the adenosine at position 28 of SEQ ID NO: 14 was changed to a thymidine, so that the present mutant ribosomal binding site is comprises the sequence aggaggaattaac (nucleic acid residues 19-31 of SEQ ID NO: 17).

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

As used herein, the "3' non-coding sequences" refer to DNA sequences located downstream of a coding sequence and include polyadenylation recognition sequences (normally limited to eukaryotes) and other sequences encoding regulatory signals capable of affecting mRNA processing or gene expression.

As used herein, the term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

As used herein, the term "sequence analysis software" refers to any computer algorithm or software program that is useful for the analysis of nucleotide or amino acid sequences. "Sequence analysis software" may be commercially available or independently developed. Typical sequence analysis-software will include: but is not limited to the GCG suite of programs (Wisconsin Package Version 9.0, Sequencher™ v. 4.05; Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.). Within the context of this application it will be understood that where sequence analysis software is used for analysis, that the results of the analysis will be based on the "default values" of the program referenced, unless otherwise specified. As used herein "default values" will mean any set of values or parameters (as set by the software manufacturer) which originally load with the software when first initialized.

The present invention provides mutant crtW genes encoding carotenoid ketolases having improved activity for converting cyclic hydroxylated carotenoids to astaxanthin. The present mutant CrtW ketolases may be used in vitro and/or in vivo for the production of astaxanthin.

Mutant CrtW Ketolases

The present mutant ketolases exhibit a significant improvement in converting cyclic hydroxylated carotenoid intermediates into astaxanthin (as measured by the % of astaxathin relative to the total carotenoid content, which remained relatively the same in all the strains). The improvement, reported relative to the wild type control (*Sphingomonas melonis* DC18 CrtW ketolase), was measured under identical reaction conditions.

As used herein, the terms "mutant carotenoid ketolase", "improved carotenoid ketolase", and "mutant CrtW ketolase" refer to the present carotenoid ketolases exhibiting an improved activity for converting cyclic hydroxylated carotenoids to astaxanthin. The mutant carotenoid ketolases were created by mutating the CrtW ketolase from *Sphingomonas melonis* DC18 (U.S. Ser. No. 11/015,433; hereby incorporated by reference). Improvements in activity were measured relative to the control (i.e., the ketolase activity of the CrtW ketolase isolated from *S. melonis* DC18 under identical reaction conditions). The present mutant carotenoid ketolases are comprised of at least one amino acid substitution relative to the CrtW ketolase from *Sphingomonas melonis* DC18 (SEQ ID NO: 3). As such, each of the present mutant ketolases have the amino acid sequence of SEQ ID NO: 3 and at least one amino acid substitution selected from the list of substitutions provided herein that increase astaxanthin production.

Each of the present mutants comprises at least one amino acid change relative to the DC18 CrtW ketolase sequence (SEQ ID NO:3). Comparisons between the present mutants and the control were conducted using identical expression systems. Improvements in activity were attributed to the structural modifications to the ketolase enzyme. The key mutations in the DC18 CrtW ketolase sequence (SEQ ID NO:3) that demonstrated an improvement in activity are as follows:

a) a mutation at amino acid position 96 changing histidine to leucine;

b) a mutation at amino acid position 203 changing arginine to tryptophan;

c) a mutations a amino acid position 205 changing alanine to valine;

d) a mutation at amino acid position 208 changing alaine to valine;

e) a mutation at amino acid position 213 changing phenylalanine to leucine; and f) a mutation at amino acid position 215 changing alanine to threonine.

Specific polypeptides of the invention corresponding to the above mutations were isolated and are described herein in SEQ ID NOs: 18, 20, 28, 30, 36, 38, 40, 42, 44, 46, 50, 52, 54, 56, 58, 62, 64, 66, 68, 70, 72, 72, and 78, where each of the polypeptides is encoded by an isolated nucleic acid molecule as set forth in SEQ ID NOs: 17, 19, 21, 22, 23, 24, 25, 26, 27, 29, 31, 32, 33, 34, 35, 37, 39, 41, 43, 45, 47, 48, 49, 51, 53, 55, 57, 59, 60, 61, 63, 65, 67, 69, 71, 73, 77, and 81, respectively.

With in the context of the above sequences the individual open reading frames of the mutants (apart from the ribosomal binding sequences) are contained within nucleic acid residues 32 through 778 from any one of SEQ ID NOs: 17, 19, 21, 22, 23, 24, 25, 26, 27, 29, 31, 32, 33, 34, 35, 37, 39, 41, 43, 45, 47, 48, 49, 51, 53, 55, 57, 59, 60, 61, 63, 65, 67, 69, 71, 73, 77, and 81.

For a particular mutant CrtW ketolase, point substitution mutations within the DNA coding region and the resulting amino acid change are specified with reference to the *Sphingomonas melonis* DC18 amino acid sequence (SEQ ID NO: 3). The wild-type amino acid (denoted by the capitalized standard single letter abbreviation) is followed by the amino acid residue position of SEQ ID NO: 3 followed by the mutant amino acid (also denoted by the standard capitalized single letter abbreviation). For example, "A205V" describes a mutation in SEQ ID NO: 3 at amino acid residue position 205 where alanine was changed to valine as a result of the mutation. A similar convention is used to describe nucleotide substitutions except that the standard lower case lettters are used (i.e., a, t, g, and c). For example, "a28t" describes a mutation in SEQ ID NO: 14 at nucleic acid residue position 28 where adenosine was changed to thymidine as a result of the mutation.

The present mutant CrtW ketolases exhibit a "significant improvement" in activity for converting cyclic hydroxylated carotenoid intermediates into astaxanthin. As used herein, a "significant improvement" is defined as having at least an 2,4-fold improvement in carotenoid ketolase activity when converting cyclic hydroxylated carotenoid intermediates into astaxanthin when compared to the activity of the *Sphingomonas melonis* DC18 CrtW ketolase (SEQ ID NO: 3) under identical reaction conditions. The activity is measured by the percentage of astaxanthin produced relative to the total carotenoid titer, which remained relatively the same in all the strains. In one embodiment, the improvement is at least 3-fold, preferably at least 4-fold, and most preferably at least 5-fold. In a preferred embodiment, the present mutant CrtW ketolases exhibit an improved activity for converting zeaxanthin and/or adonixanthin to astaxanthin.

Genes Involved in Carotenoid Production

The enzymatic pathway involved in the biosynthesis of carotenoids can be conveniently viewed in two parts, the upper isoprenoid pathway providing for the conversion of pyruvate and glyceraldehyde-3-phosphate to farnesyl pyrophosphate (FPP) and the lower carotenoid biosynthetic pathway, which provides for the synthesis of phytoene and all subsequently produced carotenoids. The upper pathway is ubiquitous in many non-carotogenic microorganisms and in these cases it will only be necessary to introduce genes that comprise the lower pathway for the biosynthesis of the desired carotenoid. The key division between the two pathways concerns the synthesis of farnesyl pyrophosphate. Where FPP is naturally present, only elements of the lower carotenoid pathway will be needed. However, it will be appreciated that for the lower pathway carotenoid genes to be effective in the production of carotenoids, it will be necessary for the host cell to have suitable levels of FPP within the cell. In another embodiment, isoprenoid biosynthesis genes may be optionally upregulated to increase the levels of FPP available for cartenoid biosynthesis. Where FPP synthesis is not provided by the host cell, it will be necessary to introduce the genes necessary for the production of FPP. Each of these pathways will be discussed below in detail.

The Upper Isoprenoid Pathway

Isoprenoid biosynthesis occurs through either of two pathways, generating the common C5 isoprene sub-unit, isopentenyl pyrophosphate (IPP). First, IPP may be synthesized through the well-known acetate/mevalonate pathway. However, recent studies have demonstrated that the mevalonate-dependent pathway does not operate in all living organisms. An alternate mevalonate-independent pathway for IPP biosynthesis has been characterized in bacteria and in green algae and higher plants (Horbach et al., *FEMS Microbiol. Lett.*, 111:135-140 (1993); Rohmer et al., *Biochem.*, 295: 517-524 (1993); Schwender et al., *Biochem.*, 316: 73-80 (1996); and Eisenreich et al., *Proc. Natl. Acad. Sci. USA*, 93: 6431-6436 (1996)).

Many steps in the mevalonate-independent isoprenoid pathway are well-known. For example, the initial steps of the alternate pathway leading to the production of IPP have been studied in *Mycobacterium tuberculosis* by Cole et al. (*Nature*, 393:537-544 (1998)). The first step of the pathway involves the condensation of two 3-carbon molecules (pyruvate and D-glyceraldehyde 3-phosphate) to yield a 5-carbon compound known as D-1-deoxyxylulose-5-phosphate. This reaction occurs by the DXS enzyme, encoded by the dxs gene. Next, the isomerization and reduction of D-1-deoxyxylulose-5-phosphate yields 2-C-methyl-D-erythritol-4-phosphate. One of the enzymes involved in the isomerization and reduction process is D-1-deoxyxylulose-5-phosphate reductoisomerase (DXR), encoded by the gene dxr (also known as ispC). 2-C-methyl-D-erythritol-4-phosphate is subsequently converted into 4-diphosphocytidyl-2C-methyl-D-erythritol in a CTP-dependent reaction by the enzyme encoded by the non-annotated gene ygbP. Recently, however, the ygbP gene was renamed as ispD as a part of the isp gene cluster (SwissProtein Accession #Q46893).

Next, the 2$^{nd}$ position hydroxy group of 4-diphosphocytidyl-2C-methyl-D-erythritol can be phosphorylated in an ATP-dependent reaction by the enzyme encoded by the ychB gene. YchB phosphorylates 4-diphosphocytidyl-2C-methyl-D-erythritol, resulting in 4-diphosphocytidyl-2C-methyl-D-erythritol 2-phosphate. The ychB gene was renamed as ispE, also as a part of the isp gene cluster (SwissProtein Accession #P24209). YgbB converts 4-diphosphocytidyl-2C-methyl-D-erythritol 2-phosphate to 2C-methyl-D-erythritol 2,4-cyclodiphosphate in a CTP-dependent manner. This gene has also been recently renamed as ispF (SwissProtein Accession #P36663).

The enzymes encoded by the gcpE (also known as ispG) and IytB (also known as ispH) genes (and perhaps others) are thought to participate in the reactions leading to formation of isopentenyl pyrophosphate (IPP) and dimethylallyl pyrophosphate (DMAPP). IPP may be isomerized to DMAPP via IPP isomerase, encoded by the idi gene. However, this enzyme is not essential for survival and may be absent in some bacteria using 2-C-methyl-D-erythritol 4-phosphate (MEP) pathway. Recent evidence suggests that the MEP pathway branches before IPP and separately produces IPP and DMAPP via the IytB gene product. A IytB knockout mutation is lethal in *E. coli* except in media supplemented with both IPP and DMAPP.

The synthesis of FPP occurs via the isomerization of IPP to dimethylallyl pyrophosphate. This reaction is followed by a sequence of two prenyltransferase reactions catalyzed by ispA, leading to the creation of geranyl pyrophosphate (GPP; a 10-carbon molecule) and farnesyl pyrophosphate (FPP; a 15-carbon molecule).

The Lower Carotenoid Biosynthetic Pathway

The division between the upper isoprenoid pathway and the lower carotenoid pathway is somewhat subjective. Because FPP synthesis is common in both carotenogenic and non-carotenogenic bacteria, the first step in the lower carotenoid biosynthetic pathway is considered to begin with the prenyltransferase reaction converting farnesyl pyrophosphate (FPP) to geranylgeranyl pyrophosphate (GGPP). The gene crtE, encoding GGPP synthetase, is responsible for this prenyltransferase reaction which adds IPP to FPP to produce the 20-carbon molecule GGPP. A condensation reaction of two molecules of GGPP occurs to form phytoene (PPPP), the first 40-carbon molecule of the lower carotenoid biosynthesis pathway. This enzymatic reaction is catalyzed by crtB, encoding phytoene synthase.

Lycopene is produced from phytoene through four sequential dehydrogenation reactions by the removal of eight atoms of hydrogen, catalyzed by the gene crtI (encoding phytoene desaturase). Intermediaries in this reaction are phytofluene, zeta-carotene, and neurosporene.

Lycopene cyclase (crtY) converts lycopene to β-carotene. In the present invention, a reporter plasmid is used which produces β-carotene as the genetic end product. However, additional genes may be used to create a variety of other carotenoids. For example, β-carotene is converted to zeaxanthin via a hydroxylation reaction resulting from the activity of β-carotene hydroxylase (encoded by the crtZ gene). β-cryptoxanthin is an intermediate in this reaction.

Carotenoid ketolases add ketogroups to the β-ionone ring of cyclic carotenoids. Carotenoid hydroxylases add hydroxyl groups to the β-ionone ring of cyclic carotenoids. Both carotenoid ketolases and hydroxylases have been reported to exhibit varying levels of substrate specificity (FIG. 1).

Preferred sources of the non-crtW carotenoid genes are from *Pantoea stewartii* (ATCC 8199; WO 02/079395), *Enterobactericeae* DC260 (U.S. Ser. No. 10/808,979), *Pantoea agglomerans* DC404 (U.S. Ser. No. 10/808,807), *Agrobacterium aurantiacum* (U.S. Pat. No. 5,811,273; U.S. Pat. No. 5,972,690; and U.S. Pat. No. 6,150,130), and *Brevundimonas vesicularis* DC263 (U.S. Ser. No. 11/015,433).

The present CrtW ketolases exhibit an improved activity for converting hydroyxiated carotenoid intermediates to astaxanthin. In one embodiment, the present CrtW ketolases are used to convert cyclic hydroxylated carotenoid intermediates into astaxanthin. In another embodiment, the present crtW genes encoding polypeptides having improved astaxanthin synthesis activity are recombinantly expressed in a host cell producing cyclic hydroxylated carotenoid intermediates. As such, the host cells are comprised of an isoprenoid biosynthesis pathway (i.e., have the ability to produce FPP) and have at least one enzyme having GGPP synthetase activity (CrtE), at least on enzyme having lycopene cyclase activity (CrtY), at least one enzyme having phytoene desaturase activity (CrtI), at least one enzyme having phytoene synthase activity (CrtB), and at least one enzyme having carotenoid hydroxylase activity (CrtZ). In a further embodiment, suitable host cells are those capable of producing FPP and functionally express at least one crtE gene, at least one crtY gene, at least one crtI gene, at least one crtB gene, and at least one crtZ gene. In yet a further embodiment, the host cell is comprises a carotenoid biosynthesis genes/gene clusters from *Pantoea agglomerans*DC404 (U.S. Ser. No. 10/808,807).

Recombinant Expression—Microbial

The gene and gene product of the instant sequences may be produced in heterologous host cells, particularly in the cells of microbial hosts. Expression in recombinant microbial hosts may be useful for the expression of various pathway intermediates, for the modulation of pathways already existing in the host, or for the synthesis of new products heretofore not possible using the host.

Preferred heterologous host cells for expression of the instant genes and nucleic acid fragments are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present nucleic acid fragments. Because of transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include, but are not limited to bacterial, fungal or yeast species such as *Aspergillus, Trichoderma, Saccharomyces, Pichia, Candida, Yarrowia, Phaffia, Hansenula*, or bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. In one embodiment, suitable bacterial host strains include *Escherichia, Bacillus*, and *Methylomonas*.

Microbial expression systems and expression vectors containing regulatory sequences that direct high-level expression of foreign proteins are well known to those skilled in the art. Any of these could be used to construct chimeric genes for expression of present ketolases. These chimeric genes could then be introduced into appropriate microorganisms via transformation to provide high level expression of the enzymes Accordingly, it is expected that introduction of chimeric genes encoding the instant bacterial enzymes under the control of the appropriate promoters will demonstrate increased or altered cyclic ketocarotenoid production. It is contemplated that it will be useful to express the instant genes both in natural host cells as well as heterologous host. Introduction of the present crtW genes into native host will result in an increased level of existing astaxanthin production. Additionally, the instant genes may also be introduced into non-native host bacteria where the existing carotenoid pathway may be manipulated.

The present mutant CrtW carotenoid ketolases are characterized by an increased activity for converting cyclic hydroxylated carotenoid intermediates into astaxanthin. In one aspect, the present CrtW ketolases are used to increase astaxanthin synthesis in a host cell capable of producing cyclic hydroxylated carotenoid intermediates. In another aspect the cyclic hydroxylated carotenoid intermediates (i.e., intermediates typically produced in the path from β-carotene to astaxanthin; FIG. 1) typically include β-cryptoxanthin, zeaxanthin, adonixanthin, 3-hydroxyechinenone, and 3'-hydroxyechinenone. In a further aspect, the cyclic hydroxylated carotenoid substrate is zeaxanthin and/or adonixanthin.

In one embodiment, the present mutant ketolases exhibit an improvement in carotenoid ketolase activity towards cyclic hydroxylated carotenoid intermediates. The improvement in activity significantly increases the percentage astaxanthin produced (i.e., conversion) relative to the total carotenoid content in the host cell. As used herein, a "significant improvement" is measured relative to a control CrtW ketolase expressed under identical conditions. The improvement in carotenoid ketolase activity is reported as a fold improvement in the percentage of astaxanthin produced relative to the amount of astaxanthin produced by the wild-type CrtW ketolase from *Sphingomonas melonis* DC18 (U.S. Ser. No. 11/015,433) measured under identical reaction conditions. In one embodiment, the significant improvement in carotenoid ketolase activity is at least 2,4-fold increase in the percentage of astaxanthin relative to the total carotenoid content of the cell, preferably at least 3-fold, more preferably at least 4-fold, and more preferably at least 5-fold improvement.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL 1, GAL10, ADH1, PGK, PHO5, GAPDH, ADC1, TRP1, URA3, LEU2, ENO, TPI (useful for expression in *Saccharomyces*); AOXI (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*, and promoters isolated from the nrta, glnB, moxF, glyoxiII, htpG, and hps genes useful for expression in Methylomonas (U.S. Ser. No. 10/689,200; herein incorporated by reference). Additionally, promoters such as the chloramphenicol resistance gene promoter may also be useful for expression in Methylomonas.

In one embodiment, a mutation to the ribosomal binding site (RBS) has been identified that enhanced astaxanthin production when operably linked to the coding region of a CrtW ketolase. In one preferred embodiment, the mutant ribosomal binding site is operably linked to one of the present mutant coding regions for enhanced astaxanthin production.

Termination control regions may also be derived from various genes native to the preferred hosts. Optionally, a termination site may be unnecessary, however, it is most preferred if included.

Industrial Production

Where commercial production of astaxanthin is desired using the present crtW ketolase genes, a variety of culture methodologies may be applied. For example, large-scale production of a specific gene product overexpressed from a recombinant microbial host may be produced by both batch and continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the fed-batch system. Fed-batch culture processes are also suitable in the present invention and comprise a typical batch system with the exception that the substrate is added in increments as the culture progresses. Fed-batch systems are useful when catabolite repression is apt to inhibit the metabolism of the cells and where it is desirable to have limited amounts of substrate in the media. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch culturing methods are common and well known in the art and examples may be found in Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36:227, (1992).

Commercial production of astaxanthin may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, disaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, methane, and/or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.*, 153:485-489 (1990)). Hence it is contemplated that the source of carbon utilized in the present invention may encompass a wide variety of carbon containing substrates and will only be limited by the choice of organism.

Recombinant Expression—Plants

Plants and algae are also known to produce carotenoid compounds. The nucleic acid fragments of the instant invention may be used to create transgenic plants having the ability to express the microbial protein. Preferred plant hosts will be any variety that will support a high production level of the instant proteins. Suitable green plants will include, but are not limited to soybean, rapeseed (*Brassica napus*, *B. campestris*), pepper, sunflower (*Helianthus annus*), cotton (*Gossypium hirsutum*), corn, tobacco (*Nicotiana tabacum*), alfalfa (*Medi-* cago sativa), wheat (*Triticum* sp), barley (*Hordeum vulgare*), oats (*Avena sativa*, L), sorghum (*Sorghum bicolor*), rice (*Oryza sativa*), *Arabidopsis*, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. *Algal* species include, but not limited to commercially significant hosts such as *Spirulina, Haemotacoccus*, and *Dunaliela*. Production of the carotenoid compounds may be accomplished by first constructing chimeric genes of present invention in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with the genetic sequences or the present invention should be capable of promoting expression of the present gene product. High-level plant promoters that may be used in this invention include the promoter of the small subunit (ss) of the ribulose-1,5-bisphosphate carboxylase from example from soybean (Berry-Lowe et al., *J. Molecular and App. Gen.*, 1:483-498 1982)), and the promoter of the chlorophyll a/b binding protein. These two promoters are known to be light-induced in plant cells (see, for example, *Genetic Engineerinq of Plants, an Agricultural Perspective*, A. Cashmore, Plenum, N.Y. (1983), pages 29-38; Coruzzi, G. et al., *J. Biol. Chem.*, 258:1399 (1983), and Dunsmuir, P. et al., *J. Mol. Appl. Gen.*, 2:285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.*, 4:2411-2418 (1985); De Almeida et al., *Mol. Gen. Genetics*, 218:78-86 (1989)), and thus that multiple events must be screened in order to obtain lines displaying the desired expression level and pattern. Such screening may be accomplished by Southern analysis of DNA blots (Southern, *J. Mol. Biol.*, 98:503 (1975)). Northern analysis of mRNA expression (Kroczek, *J. Chromatogr. Biomed. Appl.*, 618 (1-2):133-145 (1993)), Western analysis of protein expression, or phenotypic analysis.

For some applications it will be useful to direct the instant proteins to different cellular compartments. It is thus envisioned that the chimeric genes described above may be further supplemented by altering the coding sequences to encode enzymes with appropriate intracellular targeting sequences such as transit sequences (Keegstra, K., *Cell*, 56:247-253 (1989)), signal sequences or sequences encoding endoplasmic reticulum localization (Chrispeels, J. J., *Ann. Rev. Plant Phys. Plant Mol. Biol.*, 42:21-53 (1991)), or nuclear localization signals (Raikhel, N., *Plant Phys.*, 100:1627-1632 (1992)) added and/or with targeting sequences that are already present removed. While the references cited give examples of each of these, the list is not exhaustive and more targeting signals of utility may be discovered in the future that are useful in the invention.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories/BD Diagnostics (Sparks, Md.), Promega (Madison, Wis.), New England Biolabs (Beverly, Mass.), GIBCO/BRL Life Technologies (Carlsbad, Calif.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "μL" mean microliters, "L" means liters, "g" means grams, "mg" means milligrams, "μg" means micrograms, "ppm" means parts per million, and "RBS" means ribosomal binding site.

Example 1

Sphingomonas melonis DC18 crtW Ketolase

The isolation, characterization, and carotenoid profile analysis of *Sphingomonas melonis* DC18 is described in U.S. Ser. No. 11/015,433; herein incorporated by reference. Briefly, *Sphingomonas melonis* DC18 was isolated from a Pennsylvania stream. The 16S rRNA gene was isolated and sequenced (SEQ ID NO: 1). The carotenoid profile of this strain indicated the presence of a carotenoid ketolase gene. The gene encoding the CrtW ketolase was isolated and sequenced (SEQ ID NO: 2 encoding the amino acid sequence provided by SEQ ID NO: 3).

Carotenoid Analysis

*Sphingomonas melonis* DC18 cells were pelleted by centrifugation at 4000×g for 15 min, and the cell pellets were extracted with 10-mL acetone. The extraction was dried under nitrogen and redissolved in 1-2 mL of acetone. The extraction was filtered with an Acrodisc® CR25 mm syringe filter (Pall Corporation, Ann Arbor, Mich.). It was then concentrated in 0.1 mL 10% acetone+90% acetonitrile for HPLC analysis using an Agilent Series 1100 LC/MSD SI (Agilent, Foster City, Calif.).

Sample (20 µL) was loaded onto a 150 mm×4.6 mm ZOR-BAX C18 (3.5 µm particles) column (Agilent Technologies, Inc.). The column temperature was kept at 40° C. The flow rate was 1 mL/min, while the solvent running program used was:

0-2 min: 95% buffer A and 5% buffer B;
 2-10 min: linear gradient from 95% buffer A and 5% buffer B to 60% buffer A and 40% buffer B;
 10-12 min: linear gradient from 60% buffer A and 40% buffer B to 50% buffer A and 50% buffer B;
 12-18 min: 50% buffer A and 50% buffer B; and
 18-20 min: 95% buffer A and 5% buffer B.

Buffer A was 95% acetonitrile and 5% dH$_2$O; buffer B was 100% tetrahydrofuran.

The molecular weight of the major carotenoid was determined by LC-MS. Each sample of 50 µL was run on a Zorbax 2.1×150 mm SB-C18 LC column (Agilent Technologies, CA) with solvent program of:

0-30 min: linear gradient from 70% acetonitrile and 30% water to 100% acetonitrile; and
 30-45 min: 100% acetonitrile.

The mass spectrometer (Micromass Quaftro LC triple quadrapole, Micromass Limited, UK) was scanned from 100 to 1000 AMU's in 0.9 sec with an 0.1 sec interscan delay in APCI (Atomspheric Pressure Chemical Ionization) mode with the corona discharge needle at 3 KV and the APCI probe at 450° C. LC-MS analyses determined the molecular weight of the major carotenoid in DC18 to be 614. The absorption spectrum of the major carotenoid in DC18 was round-shaped at 464 nm ($\lambda_{max}$: 464). The major carotenoid in DC18 was predicted to be tretrahydroxy-β, β'-caroten-4-one. The properties we determined for the major carotenoid in DC18 ($\lambda_{max}$: 464: m/e:614) was consistent with those reported in the literature for this carotenoid (Yokoyama, A. et al, *Biosci. Biotech. Biochem.*, 60:200-203, 1996; Kleinig, H. et al., *Helvetica Chimica Acta*, 60:254-258, 1977).

Example 2

Expression of the *Sphingomonas melonis* DC18 crtW Gene in *E. coli*

This example describes expression of the *Sphingomonas melonis* DC18 crtW gene in an *E. coli* strain producing β-carotene (U.S. Ser. No. 11/015,433). Function of the ketolase gene was demonstrated by the enzymatic conversion of β-carotene to canthaxanthin.

The β-carotene producing strain used in this study was the *E. coli* strain containing plasmid pDCQ330 (SEQ ID NO: 4), which carried the βcarotene synthesis gene cluster from *Pantoea agglomerans* DC404 (U.S. Pat. No. 6,929,928 and U.S. Ser. No. 11/015433; each hereby incorporated by reference). Briefly, the β-carotene biosynthesis gene cluster crtEidiYIB from *Pantoea agglomerans* DC404 was cloned into broad host range vector pBHR1 (MoBiTec, LLC, Marco Island, Fla.). Plasmid pDCQ330 contains a unique SpeI site was engineered upstream of crtE.

The crtW ketolase gene from DC18 was amplified by PCR using primers crtW-18_F2: 5'-TCTAGAAAGGAG-GAATAACCATGACCGTCGATCACGACGCAC-3' (SEQ ID NO: 5) and crtW-18_R2: 5'-ACTAGTCTACCG-GTCTTTGCTTAACGAC-3' (SEQ ID NO:6). The PCR product was cloned into pTrcHis2-TOPO® vector and screened for clones containing the insert in the forward orientation. This resulted in pDCQ351 expressing the crtW gene from DC18. The plasmid pDCQ351 was transformed into the β-carotene accumulating *E. coli* strain containing pDCQ330. Orange transformants were obtained and their carotenoids were analyzed by HPLC as described in Example 1. Canthaxanthin standard was purchased from CaroteNature (Lupsingen, Switzerland). Canthaxanthin was the carotenoid exclusively produced in each of the strain, demonstrating the ketolase function of the crtW gene isolated from DC18.

Example 3

Isolation of Improved DC18 Ketolase Mutants for Astaxanthin Production

Although most ketolases are very active on β-carotene to make canthaxanthin, they have limited activity on cyclic hydroxylated carotenoids such as zeaxanthin and adonixanthin to make astaxanthin (FIG. 1). This example describes the screening system used to isolate improved DC18 ketolase mutants for enhanced astaxanthin production.

An *E. coli* strain producing zeaxanthin from pDCQ395 was used as the reporter strain. Zeaxanthin synthesis plasmid pDCQ395 (SEQ ID NO: 7) was constructed by cloning the β-carotene hydroxylase gene crtZ (SEQ ID NO: 8) from *Pantoea agglomerans* DC404 (U.S. Pat. No. 6,929,928) upstream of the crtEidiYIB gene cluster in the β-carotene producing plasmid pDCQ330. The DC404 crtZ was amplified with the forward primer crt404ZF: 5'-ACTAGTAAG-GAGGAATAAACCATGCTTGCGTTGTGGAATACCG-3'; SEQ ID NO: 10 and the reverse primer crt404ZR: 5'-TCTA-GAGCCTAGGTTATTTCCGGCGCGAAG-3'; SEQ ID NO: 11. The DNA fragment containing the crtZ was digested with SpeI and XbaI, and cloned into the SpeI site upstream of the crtEidiYIB genes in pDCQ330 resulting in the zeaxanthin producing plasmid pDCQ395 (SEQ ID NO: 7). Plasmid pDCQ351 contains the wild-type DC18 β-carotene ketolase gene crtW (SEQ ID NO: 2; U.S. Ser. No. 11/015,433)) expressed from the trc promoter on pTrcHis2-TOPO® vector. When pDCQ351 was transformed into the zeaxanthin reporter strain (*E. coli* containing pDCQ395), cells turned orange indicating that the ketolase activity from the wild-type crtW on pDCQ351 was too high for screening of improved crtW mutants. In order to have a clear visual screening system, the expression level of the crtW gene was reduced. The first nucleotide of the −35 region (TTGACA) of the trc promoter was mutated from T to C by site-directed mutagenesis using QuickChange® site-directed mutagenesis kit (Stratagene, La Jolla, Calif.) according to manufacturer's instructions, creating plasmid pDCQ351 M. The primers used for the site-directed mutagenesis were ptrc-35C-F: 5'-CTGAAAT-GAGCTGCTGACAATTAATCATCCGGCTCG-3' (SEQ ID NO: 12) and ptrc-35C-R: 5'-CGAGCCGGATGATTAAT-TGTCAGCAGCTCATTTCAG-3' (SEQ ID NO: 13). Plasmid pDCQ351M containing the wild type DC18 crtW expressed from the mutated trc promoter was confirmed by sequencing. When pDCQ351 M was transformed into the zeaxanthin reporter E. coli containing pDCQ395, cells remained yellow. This allowed screening of improved crtW mutants by looking for colonies changing from yellow to orange and/or orange/red. Error-prone PCR was performed with the NcoI-EcoRI fragment (SEQ ID NO: 14; "control" sequence encoding the CrtW ketolase from Sphingomonas melonis DC18) on pDCQ351 M, which include the crtW gene and its upstream ribosomal binding site (RBS). The PCR reaction was performed with AmpliTaq® DNA polymerase (Applied Biosystems, Foster City, Calif.) in GeneAmp® 10×PCR Buffer II containing $MgCl_2$ (250 µM), dNTPs (200 µM of each), primers (pTrcHis2-FF: 5'-TATCATCGACTG-CACGGTGCAC-3' (SEQ ID NO: 15) and pTrcHis2-RR: 5'-TCCTACTCAGGAGAGCGTTCAC-3'; (SEQ ID NO: 16), and pDCQ351M DNA (10 ng). In addition, each reaction contained 50, 75, 100, 125, 150 or 200 µM $MnCl_2$. The PCR conditions were as follows: 5 min at 95° C.; then 35 cycles at 92° C. for 1 min, 55° C. for 1 min, and 72° C. for 1 min; followed by additional 10 min at 72° C. The purified PCR products from reactions containing different amount $MnCl_2$ were combined and digested with NcoI and EcoRI. The digested error-prone PCR product was gel purified and ligated to NcoI/EcoRI sites of pDCQ351 M to replace the wild-type crtW gene and its RBS. The ligated DNA was electroporated into E. coli 10G (pDCQ395) reporter cells. The transformed cells were spread on LB agar containing 50 µg/mL kanamycin and 100 µg/mL ampicillin, and incubated at 30° C. for 2-3 days. One of the mutants ("MM1") was isolated from the error-prone PCR library having orange/red color indicating improved β-carotene ketolase activity.

Example 4

Confirmation of the Improved DC18 Ketolase Mutant for Astaxanthin Production This example describes characterization and confirmation of the mutant MM1 for enhanced astaxanthin production.

Mutant MM1 and the parent control containing the wild type crtW gene on pDCQ351 M were grown in 20-mL LB broth with 100 µg/mL ampicillin and 50 µg/mL kanamycin at 30° C. shaking for 2 days. Cells were pelleted by centrifugation and the carotenoids were extracted with 50% acetone+50% methanol (v/v) and analyzed by HPLC as described in Example 1. The total carotenoid titer in the control and the mutant was similar. The control (expressing the wild-type CrtW ketolase from Sphingomonas melonis DC18) produced 12% astaxanthin, 51% adonixanthin and 34% zeaxanthin. Mutant MM1 produced 81% astaxanthin, 16% adonixanthin and 2% zeaxanthin under identical reaction conditions. The analysis showed that mutant MM1 exhibited much higher activity towards adonixanthin and zeaxanthin than the parent control and most of the cyclic hydroxylated carotenoid intermediates were converted to astaxanthin as the predominant carotenoid in MM1.

Sequencing analysis indicated that mutant MM1 (SEQ ID NOs: 20-21) contained several mutations in the crtW gene as well as a mutation at the RBS (Table 1). It has an a28t mutation (SEQ ID NO: 20) at the RBS upstream of the crtW gene. It has a c209g mutation that resulted in a silent mutation at valine 59 (codon changed from gtc to gtg) of the crtW gene. It has a c655t mutation that resulted in an alanine 208 changed to valine. It has an a754g mutation that resulted in a histidine 241 changed to arginine. To confirm that the mutations in the crtW gene and/or the RBS site contributed to the phenotype of enhanced astaxanthin production, the mutant crtW gene was subcloned with the wild-type RBS (pDCQ421) or the mutant RBS (pDCQ422) into the pTrcHis2-TOPO® vector with the wild-type trc promoter. Plasmid pDCQ421 was constructed by amplifying the mutant crtW in pDCQ351 mM1 with the primers (see Example 2) crtW-18_F2 (SEQ ID NO: 5) and the crtW-18_R2 (SEQ ID NO: 6) containing the wild-type RBS and cloned the PCR product into pTrcHis2-TOPO® vector. Plasmid pDCQ422 was constructed by subcloning the mutant RBS and the mutant crtW in pDCQ351 MM1 as the NcoI-EcoRI fragment into the NcoI and EcoRI digested pDCQ351 to replace the wild type crtW with its RBS. Plasmids pDCQ421, pDCQ422 and the pDCQ351 with the wild type crtW control were transformed into the zeaxanthin reporter 10G(pDCQ395). These strains together with the original MM1 mutants were grown in 2 mL/well of LB broth with 100 µg/mL ampicillin and 50 µg/mL kanamycin in 24-well block at 30° C. shaking for 2 days. HPLC analysis of the carotenoids in the cells is shown in Table 1. Data in Table 1 confirmed that crtW mutations in MM1 contributed to the enhanced astaxanthin production. The a28t mutation in the RBS had an additional positive effect on astaxanthin production.

TABLE 1

Characterization and confirmation of the effect of MM1 mutations on improving astaxanthin production.

| Plasmid | −35[1] | RBS[2] | CrtW (443-1189)[3] | AST %[4] |
|---|---|---|---|---|
| pDCQ351M | t−>c | | | 14 |
| pDCQ351MM1 | t−>c | a28t | V59V, A208V, H241R | 83 |
| pDCQ351 | | | | 33 |
| pDCQ421 | | | V59V, A208V, H241R | 67 |
| pDCQ422 | | a28t | V59V, A208V, H241R | 91 |

[1]t−>c indicated that the first nucleotide (T) of the −35 region of the trc promoter (TTGACA) was changed to C to reduce expression.
[2]A deletion occurred at the nucleotide C of position 31 in the RBS site of pDCQ351M (corresponding to position 31 of SEQ ID NO: 14), which was inherited in the mutants and is also present in the pDCQ351M control.
[3]The crtW gene encoded on the plasmid spans from nucleotide 443 to 1189 (of plasmid pDCQ351M), corresponding to nucleotide positions 32 to 778 of SEQ ID NO: 14 (NcoI-EcoRI fragment including the RBS).
[4]Astaxanthin percentage in the total carotenoids when the crtW-encoding plasmid was transformed into the zeaxanthin reporter strain 10G(pDCQ395) and assayed under conditions as described in the example.

Example 5

Characterization of More DC18 Ketolase Mutants for Improved Astaxanthin Production Approximately 100,000 colonies were obtained from the crtW library generated by error-prone PCR. Forty-eight orange or orange/red colonies were isolated. They were grown in two of the 24-well block, each in 2 mL/well of LB broth with 100 µg/mL ampicillin and 50 µg/mL kanamycin. The blocks were incubated at 30° C. shaking for 2 days. The cells were pelleted by centrifugation and carotenoids were extracted and analyzed by HPLC as described before. The total carotenoid titer remained relatively the same in all the strains. All of the analyzed mutants showed higher astaxanthin production than the wild-type crtW control The highest was the MM1 mutant that produced 83% astaxanthin comparing to 14% astaxanthin produced by the wild-type control. These mutants were sequenced and the mutations were localized in several hot spots. Among all the 48 sequenced mutants, 40 mutants contained mutations that occurred more than once (Table 2). Some were isolated as the single mutants, and some were isolated as the mutants combined with other mutations. Eleven mutants contained the F213L mutation. Eleven mutants contained the R203W mutation. Seven mutants contained the A215T mutation. Six mutants contained the A205V mutation. Three mutants contained the A208V mutation. Two mutants contained the H96L mutation.

Except for the H96L mutation, all the other mutations were clustered at the carboxyl terminal region of the CrtW protein near the conserved H is motif involved in $Fe^{2+}$ binding. The F213 residue was conserved among many CrtW proteins. The F213L single mutation showed the largest effect on improving astaxanthin production (~72% astaxanthin). The A208V single mutant produced 43% astaxanthin. The high astaxanthin in MM1 was most likely a combinational effect of the beneficial gene mutation(s) and the beneficial RBS mutation.

TABLE 2

DC18 crtW mutations isolated more than once from the library that increased astaxanthin production. All mutations are described relative to the wild-type CrtW ketolase (SEQ ID NOs: 2-3) isolated from *Sphinogmonas melonis* DC18 (U.S. Pat. No. 11/015433).

| Mutant # | Nucletide Sequence (SEQ ID NO.) | Deduced Amino Acid (SEQ ID NO.) | Mutation[1] | RBS[2] | Additional Non-silent Mutations | Silent Mutations | Astaxanthin (% of total carotenoids) | Fold increase versus control |
|---|---|---|---|---|---|---|---|---|
| Control | NcoI-EcoRI framgent (SEQ ID NO: 14) comprising the wild type DC18 crtW ORF (SEQ ID NO: 2) | 3 | — | — | — | — | 14 | — |
| 1 | 19[3] | 20 | F213L | | | | 67-74 | 4.8-5.3 |
| 2 | 21 | 20 | F213L | | | | 72 | 5.1 |
| 3 | 22 | 20 | F213L | — | — | — | 71 | 5.1 |
| 4 | 23 | 20 | F213L | — | — | A164A | 70 | 5.0 |
| 5 | 24 | 20 | F213L | — | — | R128R | 69 | 4.9 |
| 6 | 25 | 20 | F213L | — | — | A50A | 76 | 5.4 |
| 7 | 26 | 20 | F213L | — | — | V147V | 71 | 5.1 |
| 8 | 27 | 28 | F213L | — | N199S | V79V, R184R | 71 | 5.1 |
| 9 | 29[4] | 30 | R203W | — | — | — | 51 | 3.6 |
| 10 | 31 | 30 | R203W | — | — | L165L | 51 | 3.6 |
| 11 | 32 | 30 | R203W | — | — | P70P | 50 | 3.6 |
| 12 | 33 | 30 | R203W | — | — | T108T | 51 | 3.6 |
| 13 | 34 | 30 | R203W | — | — | A28A | 54 | 3.9 |
| 14 | 35 | 36 | R203W | — | R33Q | S198S | 57 | 4.1 |
| 15 | 37 | 38 | R203W | t14c | L165V | — | 56 | 4.0 |
| 16 | 39 | 40 | R203W | a26g | K246R | — | 49 | 3.5 |
| 17 | 41[5] | 42 | R203W | | A193T | N195N | 40 | 2.9 |
| 18 | 43 | 44 | R203W | | A144V | L47L | 54 | 3.9 |
| 19 | 45 | 46 | A215T | — | — | — | 53 | 3.8 |
| 20 | 47 | 46 | A215T | — | — | G85G | 50 | 3.6 |
| 21 | 48 | 46 | A215T | — | — | T2T | 70 | 5.0 |
| 22 | 49 | 50 | A215T | — | T131A | P106P | 69 | 4.9 |
| 23 | 51 | 52 | A215T | — | W225R | A20A | 59 | 4.2 |
| 24 | 53 | 54 | A215T | — | V30M, T131A | — | 62 | 4.4 |
| 25 | 55 | 56 | A215T | — | V147E | — | 67 | 4.8 |
| 26 | 57 | 58 | A205V | — | — | — | 44 | 3.1 |
| 27 | 59 | 58 | A205V | — | — | D6D, P73P | 52 | 3.7 |
| 28 | 60 | 58 | A205V | — | — | L165L, P202P | 66 | 4.7 |
| 29 | 61 | 62 | A205V | — | V154A | — | 51 | 3.6 |
| 30 | 63 | 64 | A205V | — | T38A, L41F, A74S, S245G | A60A | 46 | 3.3 |
| 31 | 65 | 66 | A205V | — | R203Q | H96H, S121S | 35 | 2.4 |
| 32 | 67 | 68 | A208V | — | — | G55G | 43 | 3.1 |
| 33 | 69 | 70 | A208V | — | I9V | — | 44 | 3.1 |
| 34 | 20[6] | 21 | A208V | a28t | H241R | V59V | 83 | 5.9 |
| 35 | 71 | 72 | H96L | t27c | — | G55G | 64 | 4.6 |
| 36 | 73 | 74 | H96L | — | A193E | L151L | 43 | 3.1 |

[1]The nucleotide change for the corresponding amino acid change can be found in the nucleiotide sequence. Listed are locations of the amino acid residue positions relative to the wild-type CrtW ketolase sequence (SEQ ID NO: 3). The letter before the number indicates the wild type residue, and the letter after indicates the mutation residue.
[2]The C31 deletion in the ribosomal binding site (RBS) was present in all the mutants and the control, which is not shown in this table. All the mutants and the control also contain −35 ribosomal binding site t->c change in the trc promoter, which is not shown in this table.
[3]This F213L mutants was isolated four times.
[4]This R203W mutants was isolated twice.
[5]This R203W mutant containing additional A193T mutation and silent N195N mutation was designated as mutant "MM2".
[6]This A208V mutant containing additional a28t mutation at the RBS and H241R mutation and silent V59V mutation was designated as mutant "MM1".

Example 6

Construction of Other DC18 Ketolase Mutants by Combining Different Beneficial Gene Mutations for Improved Astaxanthin Production This example describes a method to further improve astaxanthin production by combining the isolated beneficial mutations.

The F213L and R203W mutations were isolated with high frequencies. Single F213L mutant showed about 72% astaxanthin selectivity. Single R203W mutant showed about 52% astaxanthin selectivity. A double mutant containing both F213L and R203W mutations was constructed by introducing the targeted R203W mutation in a single F213L mutant using the QuickChange® site-directed mutagenesis kit (Stratagene). The primers used for the site-directed mutagenesis were: 5'-MTGCCCGCAGCAACGGCTGGCCATG-GCTGGCGTCGCTGGCGAC-3'; SEQ ID NO: 75 and 5'-GTCGCCAGCGACGCCAGCCATGGCCAGC-CGTTGCTGCGGGCATT-3'; SEQ ID NO: 76.

Plasmid pDCQ425 containing the R203W/F213L double mutation (SEQ ID NOs: 77-78) was confirmed by sequencing. Plasmid pDCQ425 was transformed into the *E. coli* zeaxanthin reporter strain 10G(pDCQ395) and carotenoids were analyzed by HPLC as described above. The CrtW with the R203W/F213L double mutations showed 88% astaxanthin selectivity, which was higher than the individual mutant. This demonstrated that higher astaxanthin production could be achieved by combining different beneficial mutations in the CrtW.

Example 7

Construction of Other DC18 Ketolase Mutants by Combining the Beneficial RBS Mutations with the Gene Mutations for Improved Astaxanthin Production This example describes a method to further improve astaxanthin production by combining the isolated beneficial mutations with beneficial RBS mutations.

In Example 4, it was shown that the RBS mutation a28t in MM1 had additive effect on improving astaxanthin selectivity with the beneficial crtW gene mutations in MM1. To determine if the a28t RBS mutation could exert its additional positive effect when it was combined with another gene mutation, the a28t RBS mutation was introduced into the upstream region of a R203W mutant that had additional A193T mutation and N195N silent mutation (i.e., Mutant #17; SEQ ID NOs: 41-42). This mutant (MM2) showed about 40% astaxanthin selectivity. The primers used to introduce a28t RBS mutation to MM2 by site-directed mutagenesis were: 5'-TG-GCCCTTTCTAGAAAGGAGGGAATTAAC-CATGACCGTCGATCACGAC-3'; SEQ ID NO: 79 and 5'-GTCGTGATCGACGGTCATGGTTAATTC-CTCCTTTCTAGAAAGGGCCA-3'; SEQ ID NO: 80. The plasmid pDCQ426 containing the a28t RBS mutation in addition to the original mutations in MM2 was confirmed by sequencing (SEQ ID NO: 81). Plasmid pDCQ426 was transformed into the *E. coli* zeaxanthin reporter strain 10G (pDCQ395) and carotenoids were analyzed by HPLC as described above. This new mutant containing the MM2 gene mutation combined with the a28t RBS mutation showed 83% astaxanthin selectivity, which doubled the effect of the gene mutation alone in MM2. This demonstrated that higher astaxanthin production could be achieved by combining the beneficial RBS mutations with the beneficial mutations in the CrtW ketolase.

What is claimed is:

1. An isolated nucleic acid molecule encoding a polypeptide having carotenoid ketolase activity, wherein said polypeptide comprises an amino acid sequence which differs from SEQ ID NO: 3 solely by an amino acid substitution selected from the group consisting of:
   (a) at amino acid position number 96 of SEQ ID NO:3, substitution of histidine with leucine;
   (b) at amino acid position number 203 of SEQ ID NO:3, substitution of arginine with tryptophan;
   (c) at amino acid position number 205 of SEQ ID NO:3, substitution of alanine with valine;
   (d) at amino acid position number 208 of SEQ ID NO:3, substitution of alanine with valine;
   (e) at amino acid position number 213 of SEQ ID NO:3, substitution of phenylalanine with leucine;
   (f) at amino acid position number 215 of SEQ ID NO:3, substitution of alanine with threonine; and
   (g) any combination of (a)-(f).

2. The isolated nucleic acid molecule of claim 1 wherein said polypeptide is characterized by at least an 2.4-fold improvement in ketolase activity for converting cyclic hydroxylated carotenoid intermediates into astaxanthin when compared to the ketolase activity of the *Sphingomonas melonis* DC18 CrtW ketolase of SEQ ID NO: 3 under identical reaction conditions.

3. A chimeric gene comprising the isolated nucleic acid molecule of claim 1 operably linked to suitable regulatory sequences.

4. An isolated transformed host cell comprising the isolated nucleic acid molecule of claim 1.

5. The transformed host cell of claim 4 wherein said host cell is selected from the group consisting of bacteria, yeast, filamentous fungi, algae, and green plant cells.

6. The transformed host cell of claim 5 wherein said host cell is selected from the group consisting of *Aspergillus, Trichoderma, Saccharomyces, Pichia, Candida, Yarrowia, Phaffia, Hansenula, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus.*

7. A method for the production of a cyclic ketocarotenoid compound comprising:
   (a) providing a host cell that produces a cyclic hydroxylated carotenoid compound selected from the group consisting of β-cryptoxanthin, 3-hydroxyechinenone, 3'-hydroxyechinenone, zeaxanthin, and adonixanthin;
   (b) transforming the host cell of (a) with the nucleic acid molecule of claim 1, operably linked to suitable regulatory sequences; and
   (c) growing the transformed host cell of (b) under conditions whereby a cyclic ketocarotenoid compound is produced.

8. The method of claim 7 wherein the cyclic ketocarotenoid compound is astaxanthin.

9. The method of claim 8 wherein the transformed host cell is selected from the group consisting of bacteria, yeast, filamentous fungi, algae, and green plant cells.

10. The method of claim 9 wherein the transformed host cell is selected form the group consisting of *Aspergillus, Trichoderma, Saccharomyces, Pichia, Candida, Phaffia, Yarrowia, Hansenula, Salmonella, Bacillus, Acinetobacter, Zymomonas, Agrobacterium, Erythrobacter Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus.*

11. The method according to claim 9 wherein the transformed host cell is selected from the group consisting of *Phaffia, Yarrowia, Saccharomyces, Pichia,* and *Candida.*

* * * * *

SEQUENCE LISTING

<160> NUMBER OF SEQ ID NOS: 81

<210> SEQ ID NO 1
<211> LENGTH: 1291
<212> TYPE: DNA
<213> ORGANISM: Sphingomonas melonis DC18

<400> SEQUENCE: 1

```
acgctggcgg catgcctaac acatgcaagt cgaacgagat cttcgggtct agtggcgcac       60
gggtgcgtaa cgcgtgggaa tctgcccctt ggttcggaat aaccgttgga aacgacggct      120
aataccggat gacgacgtaa gtccaaagat ttatcgccga gggatgagcc cgcgtaggat      180
tagctagttg gtgtggtaaa ggcgcaccaa ggcgacgatc cttagctggt ctgagaggat      240
gatcagccac actgggactg agacacggcc cagactccta cgggaggcag cagtggggaa      300
tattggacaa tgggcgcaag cctgatccag caatgccgcg tgagtgatga aggccttagg      360
gttgtaaagc tctttaccc gggatgataa tgacagtacc gggagaataa gctccggcta      420
actccgtgcc agcagccgcg gtaatacgga gggagctagc gttgttcgga attactgggc      480
gtaaagcgca cgtaggcggc tttgtaagtt agaggtgaaa gcctggagct caactccaga      540
attgccttta agactgcatc gcttgaatcc aggagaggtg agtggaattc cgagtgtaga      600
ggtgaaattc gtagatattc ggaagaacac cagtggcgaa ggcggctcac tggactggta      660
```

-continued

```
ttgacgctga ggtgcgaaag cgtggggagc aaacaggatt agataccctg gtagtccacg    720
ccgtaaacga tgataactag ctgtccgggg acttggtctt tgggtggcgc agctaacgca    780
ttaagttatc cgcctgggga gtacggccgc aaggttaaaa ctcaaatgaa ttgacggggg    840
cctgcacaag cggtggagca tgtggtttaa ttcgaagcaa cgcgcagaac cttaccagcg    900
tttgacatgt ccggacgatt tccagagatg gatctctttc cttcgggaac tggaacacag    960
gtgctgcatg gctgtcgtca gctcgtgtcg tgagatgttg ggttaagtcc cgcaacgagc   1020
gcaaccctcg cctttagtta ccatcattca gttggggact ctaaaggaac cgccggtgat   1080
aagccggagg aaggtgggga tgacgtcaag tcctcatggc ccttacgcgc tgggctacac   1140
acgtgctaca atggcggtga cagtgggcag caagcacgcg agtgtgcgct aatctccaaa   1200
agccgtctca gttcggattg cactctgcaa ctcgagtgca tgaaggcgga atcgctagta   1260
atcgcggatc agcatgccgc ggtgaatacg t                                  1291
```

<210> SEQ ID NO 2
<211> LENGTH: 747
<212> TYPE: DNA
<213> ORGANISM: Sphingomonas melonis DC18
<220> FEATURE:
<221> NAME/KEY: CDS
<222> LOCATION: (1)..(747)

<400> SEQUENCE: 2

```
atg acc gtc gat cac gac gca cgg atc agc ctg ctg ctg gcc gca gcc    48
Met Thr Val Asp His Asp Ala Arg Ile Ser Leu Leu Leu Ala Ala Ala
1               5                   10                  15 atc ggc gcc gcg tgg ctg gcg atc cat gtc ggg gcg atc gtg tgg tgg    96
Ile Gly Ala Ala Trp Leu Ala Ile His Val Gly Ala Ile Val Trp Trp
            20                  25                  30 cga tgg agc ccg gcg acg gcg gtg ctc gcg atc ccc gtc gtg ctc gta   144
Arg Trp Ser Pro Ala Thr Ala Val Leu Ala Ile Pro Val Val Leu Val
        35                  40                  45 cag gcg tgg ctg agc acc ggc ctg ttc atc gtc gcg cac gat tgc atg   192
Gln Ala Trp Leu Ser Thr Gly Leu Phe Ile Val Ala His Asp Cys Met
    50                  55                  60 cac gga tcg ttc gtg ccc ggc cgg ccc gcg gtc aac cgg acc gtc ggg   240
His Gly Ser Phe Val Pro Gly Arg Pro Ala Val Asn Arg Thr Val Gly
65                  70                  75                  80 acg ctg tgc ctc ggc gcc tat gcg gga ctg tcc tat ggc cag ctc cat   288
Thr Leu Cys Leu Gly Ala Tyr Ala Gly Leu Ser Tyr Gly Gln Leu His
                85                  90                  95 ccc aag cat cat gcg cat cac gat gcg ccg ggc acc gcc gcc gac ccc   336
Pro Lys His His Ala His His Asp Ala Pro Gly Thr Ala Ala Asp Pro
            100                 105                 110 gat ttc cat gcc ggc gcg ccg cga tcc gca ctg ccg tgg ttc gcg cgc   384
Asp Phe His Ala Gly Ala Pro Arg Ser Ala Leu Pro Trp Phe Ala Arg
        115                 120                 125 ttc ttc acc agc tat tac acg cac ggc cag atc ctc cgg atc acc gcg   432
Phe Phe Thr Ser Tyr Tyr Thr His Gly Gln Ile Leu Arg Ile Thr Ala
    130                 135                 140 gcg gcg gtg ctg tac atg ctg ctc ggt gtg tcg ctg ctc aac atc gtc   480
Ala Ala Val Leu Tyr Met Leu Leu Gly Val Ser Leu Leu Asn Ile Val
145                 150                 155                 160 gtg ttc tgg gcg ttg ccg gcg ctg atc gcg ctg gcg cag ctg ttc gtc   528
Val Phe Trp Ala Leu Pro Ala Leu Ile Ala Leu Ala Gln Leu Phe Val
                165                 170                 175
```

```
ttc ggc acc ttc ctg ccg cat cgc cac ggc gac acg ccg ttc gcg gac      576
Phe Gly Thr Phe Leu Pro His Arg His Gly Asp Thr Pro Phe Ala Asp
            180                 185                 190 gcg cac aat gcc cgc agc aac ggc tgg cca cgg ctg gcg tcg ctg gcg      624
Ala His Asn Ala Arg Ser Asn Gly Trp Pro Arg Leu Ala Ser Leu Ala
        195                 200                 205 acc tgc ttc cac ttc ggc gcc tat cat cac gaa cat cac ctg agc ccg      672
Thr Cys Phe His Phe Gly Ala Tyr His His Glu His His Leu Ser Pro
210                 215                 220 tgg acg ccc tgg tgg cag ttg ccg cgc gtc ggc cag cct gcc gcc gga      720
Trp Thr Pro Trp Trp Gln Leu Pro Arg Val Gly Gln Pro Ala Ala Gly
225                 230                 235                 240 cac cgg tcg tta agc aaa gac cgg tag                                  747
His Arg Ser Leu Ser Lys Asp Arg
                245
```

<210> SEQ ID NO 3
<211> LENGTH: 248
<212> TYPE: PRT
<213> ORGANISM: Sphingomonas melonis DC18

<400> SEQUENCE: 3

```
Met Thr Val Asp His Asp Ala Arg Ile Ser Leu Leu Ala Ala Ala
1               5                   10                  15

Ile Gly Ala Ala Trp Leu Ala Ile His Val Gly Ala Ile Val Trp Trp
                20                  25                  30

Arg Trp Ser Pro Ala Thr Ala Val Leu Ala Ile Pro Val Val Leu Val
            35                  40                  45

Gln Ala Trp Leu Ser Thr Gly Leu Phe Ile Val Ala His Asp Cys Met
        50                  55                  60

His Gly Ser Phe Val Pro Gly Arg Pro Ala Val Asn Arg Thr Val Gly
65                  70                  75                  80

Thr Leu Cys Leu Gly Ala Tyr Ala Gly Leu Ser Tyr Gly Gln Leu His
                85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125

Phe Phe Thr Ser Tyr Tyr Thr His Gly Gln Ile Leu Arg Ile Thr Ala
    130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Ala His Asn Ala Arg Ser Asn Gly Trp Pro Arg Leu Ala Ser Leu Ala
        195                 200                 205

Thr Cys Phe His Phe Gly Ala Tyr His His Glu His His Leu Ser Pro
    210                 215                 220

Trp Thr Pro Trp Trp Gln Leu Pro Arg Val Gly Gln Pro Ala Ala Gly
225                 230                 235                 240

His Arg Ser Leu Ser Lys Asp Arg
                245
```

<210> SEQ ID NO 4
<211> LENGTH: 10926

<210> TYPE: DNA
<213> ORGANISM: artificial sequence
<220> FEATURE:
<223> OTHER INFORMATION: plasmid

<400> SEQUENCE: 4

```
ctcgggccgt ctcttgggct tgatcggcct tcttgcgcat ctcacgcgct cctgcggcgg      60
cctgtagggc aggctcatac ccctgccgaa ccgcttttgt cagccggtcg gccacggctt     120
ccggcgtctc aacgcgcttt gagattccca gcttttcggc caatccctgc ggtgcatagg     180
cgcgtggctc gaccgcttgc gggctgatgg tgacgtggcc cactggtggc cgctccaggg     240
cctcgtagaa cgcctgaatg cgcgtgtgac gtgccttgct gccctcgatg ccccgttgca     300
gccctagatc ggccacagcg gccgcaaacg tggtctggtc gcgggtcatc tgcgctttgt     360
tgccgatgaa ctccttggcc gacagcctgc cgtcctgcgt cagcggcacc acgaacgcgg     420
tcatgtgcgg gctggtttcg tcacggtgga tgctggccgt cacgatgcga tccgccccgt     480
acttgtccgc cagccacttg tgcgccttct cgaagaacgc cgcctgctgt tcttggctgg     540
ccgacttcca ccattccggg ctggccgtca tgacgtactc gaccgccaac acagcgtcct     600
tgcgccgctt ctctggcagc aactcgcgca gtcggcccat cgcttcatcg gtgctgctgg     660
ccgcccagtg ctcgttctct ggcgtcctgc tggcgtcagc gttgggcgtc tcgcgctcgc     720
ggtaggcgtg cttgagactg gccgccacgt tgcccatttt cgccagcttc ttgcatcgca     780
tgatcgcgta tgccgccatg cctgcccctc ccttttggtg tccaaccggc tcgacggggg     840
cagcgcaagg cggtgcctcc ggcgggccac tcaatgcttg agtatactca ctagactttg     900
cttcgcaaag tcgtgaccgc ctacggcggc tgcggcgccc tacgggcttg ctctccgggc     960
ttcgccctgc gcggtcgctg cgctcccttg ccagcccgtg gatatgtgga cgatggccgc    1020
gagcggccac cggctggctc gcttcgctcg gcccgtggac aaccctgctg acaagctga    1080
tggacaggct gcgcctgccc acgagcttga ccacagggat tgcccaccgg ctacccagcc    1140
ttcgaccaca tacccaccgg ctccaactgc gcggcctgcg gccttgcccc atcaattttt    1200
ttaattttct ctggggaaaa gcctccggcc tgcggcctgc gcgcttcgct tgccggttgg    1260
acaccaagtg gaaggcgggt caaggctcgc gcagcgaccg cgcagcggct tggccttgac    1320
gcgcctggaa cgaccaagc ctatgcgagt ggggcagtc gaaggcgaag cccgcccgcc     1380
tgccccccga gacctgcagg gggggggggg cgctgaggtc tgcctcgtga agaaggtgtt    1440
gctgactcat accaggcctg aatcgcccca tcatccagcc agaaagtgag ggagccacgg    1500
ttgatgagag ctttgttgta ggtggaccag ttggtgattt tgaacttttg ctttgccacg    1560
gaacggtctg cgttgtcggg aagatgcgtg atctgatcct tcaactcagc aaaagttcga    1620
tttattcaac aaagccgccg tcccgtcaag tcagcgtaat gctctgccag tgttacaacc    1680
aattaaccaa ttctgattag aaaaactcat cgagcatcaa atgaaactgc aatttattca    1740
tatcaggatt atcaatacca tatttttgaa aaagccgttt ctgtaatgaa ggagaaaact    1800
caccgaggca gttccatagg atggcaagat cctggtatcg gtctgcgatt ccgactcgtc    1860
caacatcaat acaacctatt aatttcccct cgtcaaaaat aaggttatca agtgagaaat    1920
caccatgagt gacgactgaa tccggtgaga atggcaaaag cttatgcatt tctttccaga    1980
cttgttcaac aggccagcca ttacgctcgt catcaaaatc actcgcatca accaaaccgt    2040
tattcattcg tgattgcgcc tgagcgagac gaaatacgcg atcgctgtta aaaggacaat    2100
tacaaacagg aatcgaatgc aaccggcgca ggaacactgc cagcgcatca acaatatttt    2160
```

```
cacctgaatc aggatattct tctaatacct ggaatgctgt tttcccgggg atcgcagtgg    2220
tgagtaacca tgcatcatca ggagtacgga taaaatgctt gatggtcgga agaggcataa    2280
attccgtcag ccagtttagt ctgaccatct catctgtaac atcattggca acgctacctt    2340
tgccatgttt cagaaacaac tctggcgcat cgggcttccc atacaatcga tagattgtcg    2400
cacctgattg cccgacatta tcgcgagccc atttataccc atataaatca gcatccatgt    2460
tggaatttaa tcgcggcctc gagcaagacg tttcccgttg aatatggctc ataacacccc    2520
ttgtattact gtttatgtaa gcagacagtt ttattgttca tgatgatata ttttttatctt    2580 gtgcaatgta acatcagaga ttttgagaca caacgtggct ttccccccccc cccctgcagg    2640 tcccgagcct cacggcggcg agtgcggggg ttccaagggg gcagcgccac cttgggcaag    2700
gccgaaggcc gcgcagtcga tcaacaagcc cggaggggc cacttttgc cggaggggga    2760 gccgcgccga aggcgtgggg gaaccccgca ggggtgccct tctttgggca ccaaagaact    2820
agatataggc gaaatgcga aagacttaaa aatcaacaac ttaaaaaagg ggggtacgca    2880
acagctcatt gcggcacccc ccgcaatagc tcattgcgta ggttaaagaa aatctgtaat    2940
tgactgccac ttttacgcaa cgcataattg ttgtcgcgct gccgaaaagt tgcagctgat    3000
tgcgcatggt gccgcaaccg tgcggcaccc taccgcatgg agataagcat ggccacgcag    3060
tccagagaaa tcggcattca agccaagaac aagcccggtc actgggtgca aacgaacgc    3120 aaagcgcatg aggcgtgggc cgggcttatt gcgaggaaac ccacggcggc aatgctgctg    3180
catcacctcg tggcgcagat gggccaccag aacgccgtgg tggtcagcca aagacactt    3240 tccaagctca tcggacgttc tttgcggacg gtccaatacg cagtcaagga cttggtggcc    3300
gagcgctgga tctccgtcgt gaagctcaac ggccccggca ccgtgtcggc ctacgtggtc    3360
aatgaccgcg tggcgtgggg ccagccccgc gaccagttgc gcctgtcggt gttcagtgcc    3420
gccgtggtgg ttgatcacga cgaccaggac gaatcgctgt tggggcatgg cgacctgcgc    3480
cgcatcccga ccctgtatcc gggcgagcag caactaccga ccggccccgg cgaggagccg    3540
cccagccagc ccggcattcc gggcatggaa ccagacctgc cagccttgac cgaaacggag    3600
gaatgggaac ggcgcgggca gcagcgcctg ccgatgcccg atgagccgtg ttttctggac    3660
gatggcgagc cgttggagcc gccgacacgg gtcacgctgc cgcgccggta gcacttgggt    3720
tgcgcagcaa cccgtaagtg cgctgttcca gactatcggc tgtagccgcc tcgccgccct    3780 atccttgtc tgcctcccg cgttgcgtcg cggtgcatgg agccgggcca cctcgacctg    3840
aatggaagcc ggcggcacct cgctaacgga ttcaccgttt ttatcaggct ctgggaggca    3900
gaataaatga tcatatcgtc aattattacc tccacgggga gagcctgagc aaactggcct    3960
caggcatttg agaagcacac ggtcacactg cttccggtag tcaataaacc ggtaaaccag    4020
caatagacat aagcggctat ttaacgaccc tgccctgaac cgacgaccgg gtcgaatttg    4080
ctttcgaatt tctgccattc atccgcttat tatacttatt caggcgtagc accaggcgtt    4140
taagggcacc aataactgcc ttaaaaaaat tacgccccgc cctgccactc atcgcagtac    4200
tgttgtaatt cattaagcat tctgccgaca tggaagccat cacagacggc atgatgaacc    4260
tgaatcgcca gcggcatcag caccttgtcg ccttgcgtat aatatttgcc catggtgaaa    4320
acgggggcga agaagttgtc catattggcc acgtttaaat caaaactggt gaaactcacc    4380
cagggattgg ctgagacgaa aaacatattc tcaataaacc ctttagggaa ataggccagg    4440
ttttcaccgt aacacgccac atcttgcgaa tatatgtgta gaaactgccg gaaatcgtcg    4500
tggtattcac tccagagcga tgaaaacgtt tcagtttgct catggaaaac ggtgtaacaa    4560
```

```
gggtgaacac tatcccatat caccagctca ccgtctttca ttgccatacg gaattctagc    4620
gcgggcgctg ccagaggtgc ggatcgcgcg gcggccagct cgccttccgg gaagccatcg    4680
cctgcttcgc gccggaaata accagcgcca gcttctccgc gcgcgtcgtg ccctggcggg    4740
tatcccatgc tttttcaccc gccatcagca ccttcacccc gatctcacga tacaccccgt    4800
gcgcggtggc aatcgcccag gcggagcgca ggggcagatc ccccagcccg caagcgctg     4860
actgataata gggctcagcc tcggtcacca gccgcgctgc cagacgcgcc agcgccggac    4920
ggttggcccg cacggtgcag gtctgttcat tgagtccgac ttccgccagc cactgctgcg    4980
gcaggtagca gcgtcccacc tgcgcatcgt caacgatatc cctggcgata ttggtgagct    5040
gaaaggcaat gcccagatcg caggcgcgat ccagcgtggc ttcgtcccgc actcccatca    5100
ccctggccat catcaggccg accacgcccg ccacgtgata acagtagcgg agcgtatcat    5160
cgaggctgta atagcgctcg ttgcgcacgt ccatcgcata gccttccagg tggtcgaagg    5220
cctgagtagg cggaatggca tgggcgaggg caacctcctg aaaggcggcg aacggcggct    5280
cttgcatggt ttccccgtcg taggcgcggc gcgtcatctt acgcagccgt tgcaggcgcg    5340
cctcgggcgt gtcgctctgc tcggtcgggg cagcaaaacc caccacctgt ccgtcgataa    5400
catcgtcgca gtagcggcac caggtataga gcatcagcgc gctgcgccgg gtgcgtttgt    5460
caaacagctt tgaggcggtg gcgaaacttt tagaaccggc ggtcatggtg gcgctggcgt    5520
gttcgagaag cggctgggac attacgctaa atcctttaac attaactggg ccgttgcctt    5580
ggcggatccg atcacgcccg gcacgccagc gccgggatgc gttccggcgc cgaccaggta    5640
gaggttatca accacgctgt cgcggttgtg cgcggccgga accaggcgctct gggtgaggat    5700
cggctccagt gaaaacgctg acccctgcca ggcatcgagc gtatcgcgaa aatcttccgg    5760
cgtgaacatg cggtgcgtca ccagctggga gcgcagcccc ggcatatagc gcgcttcgag    5820
ataatcaaaa atgcgatccc gcagacgcgg cccttccacg ctccagtcga gcggggcgtt    5880
accgaggtgc ggcaccggcg cgagcacata gtagctgccg caccccggcg gggccagcga    5940
cgggtcggtt acgcagggcg catgcagata gagcgaaaaa tcttccgaca gggtgtcggc    6000
gctgaaaatt tcatcgatta gcgctttata acgcgggcca aagcagacgg tatggtgcgc    6060
cagctgggtg tgatggtgat ccaggccaaa atagagcacg aacagcgagt tgctcatgcg    6120
cttgcgtttc agcttttttgg ccgtagcggc gccgtgcggg tgatggccga gcagtcgggc    6180
ataggtattt accacgtccg cgttcgaggc caccgccgca gcctccagcc gctgcccgtt    6240
aaccagatgc acggccttca cctgattgtc caccgtctcc agccgctcaa cctgagcgtt    6300
aagggtgagg gtgccgccaa gatcctgaaa cagcttcacc atgccctgaa ccagcgcacc    6360
ggtgccgccg cgcgggaacc agacgcccca ttcccgctcc agggcgtgga tcagggtgta    6420
aatagaagac gtggagaacg ggttgccgcc caccagcagc gagtgaaacg aaaatgcctg    6480
ccgcaggtgc tcgtcttcca cgtaggccga cactttgtcg tacacgctgc gccatgcctg    6540
cagccgcgcc agttgaggac cggcgcgcag catgtcgcga acgagagaa acggcaccgc     6600
gccgagcttc agatagcctt cggcaaacac cgcccgggag tagtcgagga agcggtgata    6660
gcccgccacg tcgttcgggt taaacgcggc gatctgcgac tcaagcgccg cctgatcgtt    6720
ggcgtagtcg aaaaccttgc cgtcttccca gcacaggcga tagaacggcg tcaccggcat    6780
cagctcaacg tagtccttca gccgttttcc ggcgagggtg aacagctcct caatggcgga    6840
gggatcggtg atgacggtgg gacccgcatc aaaggtaaag ccgcgatctt cgtagacata    6900
```

-continued

```
ggcgcggccg ccgggtttgt cgcggctctc cagcagcgtg gtaggaatgc ccgccgcctg    6960
gaggcgaatc gccagcgcca gtccgccgaa cccggcgcca attacaatgg tttgtttcat    7020
ttatgatggg ctcgcagaga agaatgagtg tggagcaggg cttttgatcgc ccgacaatc    7080 ggcaccggcg gtttgccaag cagcaggcgc gcgcggtcgg cggagcgaag ctggccggca    7140
taaaaacggg cgatcagctg ctcgtcaagc tggtaaaacc gctgcatcac gcgccagcgc    7200
tggtcgggtg tgccggccag gaaaagcatg cggttaagca ggcggaaaaa gcgttgtgtc    7260
tgccagtggc gcgccgcgaa atcggcgatc agctgataga gcgcgccctg atgcagtccc    7320
ggcgcgttgg caatgcggtc cgccagccga accgccagcg gcagcgaata gccggtggtg    7380
gcatggaaca gaccggcgcg caggccgctg accggctgat gatggaactg gtgccagaag    7440
gcggccggat cgccggacag ggtgatcggc agcgcccct gttcctcacg caccagccgc     7500
gcaagctgcc agccctgctg gcgggcgtaa tcggcaatcc gcgcgcgggc tgaatcggcg    7560
tcgagcgtcg ggccgtcaat gtagtgcgtg tcttcgataa gcagggtgtc ggcgctgagc    7620
ggcagggtat agacaaagcg gtagccgttg ccctgggcga cgcgggcatc catcaggatc    7680
gggcgcgtta acccgtgggg cgcggtcagt tgccactcct ggccgatgaa cgcctgatag    7740
ccaatgctga ggtgcggcga gggctgatag ccgcggccat caatcaccgc cccggcggta    7800
aagcgtcgtc cgtcgctgag ggttacttcc tgcccgctca cccgtgacac ggtcacgttt    7860
gtcagcaaat tctctttcat cagcccgcgc atcgcttggg caaaacgcgt ggaggtgatg    7920
gtcaggtagc cgtcatgcag ggtgcgcgac acgttcggaa agtggacgtc gtacccgtcc    7980
cagcgatggg ccaccagcgg cgccagccag gcgtgctggg ctggcgtgat atcgtgttgg    8040
tgaaaggacc aggtgtggtt tccgccgggc gcgtcgccgc actccagcat taatacagca    8100
agcgtcggat gacgctgctt tagtcgccag gcgataagcc cgttggccag ccccgcgccg    8160
accagaatca gatcccattt tttcataccg ctccccggta taaggcaccg tactgcgtca    8220
cagggatgcg ccgccgttga ccggaagcag cgtggcgtgt cgcaacgcct gcaggtttgc    8280
actgccggta cagaaacagg cgatccgcag ctgcgtaatc agggtgcgga aatgggcaat    8340
tgccgcgtcg ccggaggcgt tggcatgcgc cagcaccgcc gcggcctggc ccaccagatc    8400
tgcacccagc gcgatggctt ttgctgcgtc aatgccgttg gcgatgccgc cggaggcgat    8460
aagcgggata tcaggcagcg caagatggac gcgacgcagc gcatcggcag taggaatgcc    8520
ccagtcggca aaggccatcg ccacatttcg cgcctcgggg gtcggggcgc gttcagcttc    8580
caccgccgcc cagctggttc cgcccgcgcc ggcaatgtcg atcatcgcca cgccgacgtc    8640
cgccagtcgg caggcaacgt ccggggagat cccggcgccc acctctttaa ccaccaccgg    8700
taccggcagg tcgcgcacca gctgcgcaat ggcgttgagg atgccgcgcc agtcgcgatc    8760
gccgccgccc tggagcgcct cctgcagcgg gttcagatgc acaattaacg cgtcggcgtc    8820
gatcatgtcc accgcgcgcc gggcgtagtc cagcccctgc gcaccgcgga tctgcgccgc    8880
gccaaggtta gccagcagcg gcacgtccgg ggcgatatgg cgtagctggg catccagccc    8940
gtgctgcgcg ccgtcctcca gcgccacgcg ctgggaaccg acgcccatcg ccagcccaag    9000
ggtttgcgcc gcctgggcca gatgacggtt aatgtctctg gcgcgcgccg cgccgccggt    9060
catggagctg atcagcaccg gggctttcag cgggcgggaa acagggtgg tggagagatc     9120 gataccgtcg agatccagct ccgggagggc gcagtgttca aaacgccagg cgtcaaatcc    9180
ggtgcgaatg gtactcatcg cccggtcagg gtgcagcacg atatccaggt ggtcattttt    9240
acgctgaacc agatgcgcgt ccttcatgtg atctccacaa atattaccgg ggtgtatccg    9300
```

-continued

```
ttgctcagct aaacgcggcc agctgttttg aaaaccaggc gtgcataaag cgtcgcgtgg    9360
cctggttttt tccgcaggcg cgtgaaaaat gggcgtctgc gcggcgcaga tgggtgtcga    9420
gccgctcgcg caccgcgtcg ctgccgagca tcgccaccag cgtggactta cccgcgtcct    9480
tattgatgtc tttgccggtc ccggcatggc cgtccgccag atcgtccagc agctggaacg    9540
cctggcctaa atcctgcgca aagcagcgca ttttctggcg cgccgccggc gaggcgcctg    9600
ccgccagggc cgcgatttgc agcgtggcac caaacagcac gctggttttc agttcgttgg    9660
tggtggcgat ctcctcggcg ctgcgcgggg cggtgccttc acgcagatcc ttatactgac    9720
cctgcaccag accctgggta ccgaccgcca tcgacagctc cgccaccgcc tggctgcggc    9780
actcgggaga caatccctgc gccgcgacca tcacgccaaa ggcgctgctg agcaacgcta    9840
ccgcagcgag aattgccacg tcttcaccat actggcgatg aatggtaggg cgaccgcgcc    9900
ggagcgccgc gttatccatg cagggaatat cgtcgaggat cagcgacgag gcgtgcacca    9960
tttccaccgc acaggccata tccagcaggc cggggtggtc gcgatcgcag ccgaggtcgc   10020
gggcggcgag gatcaggagc agcgggcgaa tgcgtttccc cggtgccagt acgccttcgc   10080
gcattgcgct gctgacccga tcccgctcat cgccaacggg cagcagttca tccaggcgac   10140
gttgcagggc agcgtgcagc tcatgcagtt ccccgtcgtg accggatgtg gtttcaaagg   10200
gtcttgtcat ggttggtacc cggcgtctcg actagtgaat tccggatgag cattcatcag   10260
gcgggcaaga atgtgaataa aggccggata aaacttgtgc ttattttctt ttacggtctt   10320
taaaaaggcc gtaatatcca gctgaacggt ctggttatag gtacattgag caactgactg   10380
aaatgcctca aaatgttctt tacgatgcca ttgggatata tcaacggtgg tatatccagt   10440
gatttttttc tccattttag cttccttagc tcctgaaaat ctcgataact caaaaaatac   10500
gcccggtagt gatcttattt cattatggtg aaagttggaa cctcttacgt gccgatcaac   10560
gtctcatttt cgccaaaagt tggcccaggg cttcccggta tcaacaggga caccaggatt   10620
tatttattct gcgaagtgat cttccgtcac aggtatttat tcggcgcaaa gggcctcgtg   10680
atacgcctat ttttataggt taatgtcatg ataataatgg tttcttagac gtcaggtggc   10740
acttttcggg gaaatgtgcg cgcccgcgtt cctgctggcg ctgggcctgt ttctggcgct   10800
ggacttcccg ctgttccgtc agcagctttt cgcccacggc cttgatgatc gcggcggcct   10860
tggcctgcat atcccgattc aacggcccca gggcgtccag aacgggcttc aggcgctccc   10920
gaaggt                                                              10926
```

<210> SEQ ID NO 5
<211> LENGTH: 43
<212> TYPE: DNA
<213> ORGANISM: artificial sequence
<220> FEATURE:
<223> OTHER INFORMATION: primer

<400> SEQUENCE: 5
tctagaaagg aggaataaac catgaccgtc gatcacgacg cac     43

<210> SEQ ID NO 6
<211> LENGTH: 28
<212> TYPE: DNA
<213> ORGANISM: artificial sequence
<220> FEATURE:
<223> OTHER INFORMATION: primer

<400> SEQUENCE: 6

```
actagtctac cggtctttgc ttaacgac                                           28
```

<210> SEQ ID NO 7
<211> LENGTH: 11512
<212> TYPE: DNA
<213> ORGANISM: artificial sequence
<220> FEATURE:
<223> OTHER INFORMATION: plasmid

<400> SEQUENCE: 7

```
ctcgggccgt ctcttgggct tgatcggcct tcttgcgcat ctcacgcgct cctgcggcgg       60
cctgtagggc aggctcatac ccctgccgaa ccgcttttgt cagccggtcg ccacggctt       120
ccggcgtctc aacgcgcttt gagattccca gcttttcggc caatccctgc ggtgcatagg      180
cgcgtggctc gaccgcttgc gggctgatgg tgacgtggcc cactggtggc cgctccaggg      240
cctcgtagaa cgcctgaatg cgcgtgtgac gtgccttgct gccctcgatg ccccgttgca      300
gccctagatc ggccacagcg gccgcaaacg tggtctggtc gcgggtcatc tgcgctttgt      360
tgccgatgaa ctccttggcc gacagcctgc cgtcctgcgt cagcggcacc acgaacgcgg      420
tcatgtgcgg gctggtttcg tcacggtgga tgctggccgt cacgatgcga tccgccccgt      480
acttgtccgc cagccacttg tgcgccttct cgaagaacgc cgcctgctgt cttggctgg      540
ccgacttcca ccattccggg ctggccgtca tgacgtactc gaccgccaac acagcgtcct      600
tgcgccgctt ctctggcagc aactcgcgca gtcggcccat cgcttcatcg gtgctgctgg      660
ccgcccagtg ctcgttctct ggcgtcctgc tggcgtcagc gttgggcgtc tcgcgctcgc      720
ggtaggcgtg cttgagactg gccgccacgt tgcccatttt cgccagcttc ttgcatcgca      780
tgatcgcgta tgccgccatg cctgccgctc cttttggtg tccaaccggc tcgacgggg      840
cagcgcaagg cggtgcctcc ggcgggccac tcaatgcttg agtatactca ctagactttg      900
cttcgcaaag tcgtgaccgc ctacggcggc tgcggcgccc tacgggcttg ctctccgggc      960
ttcgccctgc gcggtcgctg cgctcccttg ccagcccgtg gatatgtgga cgatggccgc     1020
gagcggccac cggctggctc gcttcgctcg gccccgtggac aaccctgctg acaagctga     1080
tggacaggct gcgcctgccc acgagcttga ccacagggat tgcccaccgg ctacccagcc     1140
ttcgaccaca tacccaccgg ctccaactgc gcggcctgcg gccttgcccc atcaattttt     1200
ttaattttct ctggggaaaa gcctccggcc tgcggcctgc gcgcttcgct tgccggttgg     1260
acaccaagtg gaaggcgggt caaggctcgc gcagcgaccg cgcagcggct tggccttgac     1320
gcgcctggaa cgacccaagc ctatgcgagt gggggcagtc gaaggcgaag cccgcccgcc     1380
tgccccccga gacctgcagg ggggggggg cgctgaggtc tgcctcgtga agaaggtgtt     1440
gctgactcat accaggcctg aatcgcccca tcatccagcc agaaagtgag ggagccacgg     1500
ttgatgagag ctttgttgta ggtggaccag ttggtgattt tgaacttttg ctttgccacg     1560
gaacggtctg cgttgtcggg aagatgcgtg atctgatcct tcaactcagc aaaagttcga     1620
tttattcaac aaagccgccg tcccgtcaag tcagcgtaat gctctgccag tgttacaacc     1680
aattaaccaa ttctgattag aaaaactcat cgagcatcaa atgaaactgc aatttattca     1740
tatcaggatt atcaatacca tatttttgaa aaagccgttt ctgtaatgaa ggagaaaact     1800
caccgaggca gttccatagg atggcaagat cctggtatcg gtctgcgatt ccgactcgtc     1860
caacatcaat acaacctatt aatttcccct cgtcaaaaat aaggttatca agtgagaaat     1920
caccatgagt gacgactgaa tccggtgaga atggcaaaag cttatgcatt tctttccaga     1980
cttgttcaac aggccagcca ttacgctcgt catcaaaatc actcgcatca accaaaccgt     2040
```

```
tattcattcg tgattgcgcc tgagcgagac gaaatacgcg atcgctgtta aaaggacaat    2100
tacaaacagg aatcgaatgc aaccggcgca ggaacactgc cagcgcatca acaatatttt    2160
cacctgaatc aggatattct tctaataaacct ggaatgctgt tttcccgggg atcgcagtgg    2220
tgagtaacca tgcatcatca ggagtacgga taaaatgctt gatggtcgga agaggcataa    2280
attccgtcag ccagtttagt ctgaccatct catctgtaac atcattggca acgctacctt    2340
tgccatgttt cagaaacaac tctggcgcat cgggcttccc atacaatcga tagattgtcg    2400
cacctgattg cccgacatta tcgcgagccc atttataccc atataaatca gcatccatgt    2460
tggaatttaa tcgcggcctc gagcaagacg tttcccgttg aatatggctc ataacacccc    2520
ttgtattact gtttatgtaa gcagacagtt ttattgttca tgatgatata tttttatctt    2580
gtgcaatgta acatcagaga ttttgagaca caacgtggct ttccccccccc ccctgcagg    2640 tcccgagcct cacggcggcg agtgcggggg ttccaagggg gcagcgccac cttgggcaag    2700
gccgaaggcc gcgcagtcga tcaacaagcc ccggagggc cacttttgc cggaggggga    2760 gccgcgccga aggcgtgggg gaaccccgca ggggtgccct tctttgggca ccaaagaact    2820
agatataggg cgaaatgcga aagacttaaa aatcaacaac ttaaaaaagg ggggtacgca    2880
acagctcatt gcggcacccc ccgcaatagc tcattgcgta ggttaaagaa aatctgtaat    2940
tgactgccac ttttacgcaa cgcataattg ttgtcgcgct gccgaaaagt tgcagctgat    3000
tgcgcatggt gccgcaaccg tgcggcaccc taccgcatgg agataagcat ggccacgcag    3060
tccagagaaa tcggcattca agccaagaac aagcccggtc actgggtgca aacgaacgc    3120 aaagcgcatg aggcgtgggc cgggcttatt gcgaggaaac ccacggcggc aatgctgctg    3180
catcacctcg tggcgcagat gggccaccag aacgccgtgg tggtcagcca aagacactt    3240 tccaagctca tcggacgttc tttgcggacg gtccaatacg cagtcaagga cttggtggcc    3300
gagcgctgga tctccgtcgt gaagctcaac ggccccggca ccgtgtcggc ctacgtggtc    3360
aatgaccgcg tggcgtgggg ccagccccgc gaccagttgc gcctgtcggt gttcagtgcc    3420
gccgtggtgg ttgatcacga cgaccaggac gaatcgctgt tggggcatgg cgacctgcgc    3480
cgcatcccga ccctgtatcc gggcgagcag caactaccga ccggccccgg cgaggagccg    3540
cccagccagc ccggcattcc gggcatggaa ccagacctgc cagccttgac cgaaacggag    3600
gaatgggaac ggcgcgggca gcagcgcctg ccgatgcccg atgagccgtg ttttctggac    3660
gatggcgagc cgttggagcc gccgacacgg gtcacgctgc cgcgccggta gcacttgggt    3720
tgcgcagcaa cccgtaagtg cgctgttcca gactatcggc tgtagccgcc tcgccgccct    3780
ataccttgtc tgcctccccg cgttgcgtcg cggtgcatgg agccgggcca cctcgacctg    3840
aatggaagcc ggcggcacct cgctaacgga ttcaccgttt ttatcaggct ctgggaggca    3900
gaataaatga tcatatcgtc aattattacc tccacgggga gagcctgagc aaactggcct    3960
caggcatttg agaagcacac ggtcacactg cttccggtag tcaataaacc ggtaaaccag    4020
caatagacat aagcggctat ttaacgaccc tgccctgaac cgacgaccgg gtcgaatttg    4080
ctttcgaatt tctgccattc atccgcttat tatacttatt caggcgtagc accaggcgtt    4140
taagggcacc aataactgcc ttaaaaaaat tacgccccgc cctgccactc atcgcagtac    4200
tgttgtaatt cattaagcat tctgccgaca tggaagccat cacagacggc atgatgaacc    4260
tgaatcgcca gcggcatcag cacccttgtcg ccttgcgtat aatatttgcc catggtgaaa    4320
acgggggcga agaagttgtc catattggcc acgtttaaat caaaactggt gaaactcacc    4380
```

-continued

```
cagggattgg ctgagacgaa aaacatattc tcaataaacc ctttagggaa ataggccagg    4440
ttttcaccgt aacacgccac atcttgcgaa tatatgtgta gaaactgccg gaaatcgtcg    4500
tggtattcac tccagagcga tgaaaacgtt tcagtttgct catggaaaac ggtgtaacaa    4560
gggtgaacac tatcccatat caccagctca ccgtctttca ttgccatacg gaattctagc    4620
gcgggcgctg ccagaggtgc ggatcgcgcg gcggccagct cgccttccgg gaagccatcg    4680
cctgcttcgc gccggaaata accagcgcca gcttctccgc gcgcgtcgtg ccctggcggg    4740
tatcccatgc ttttcaccc gccatcagca ccttcacccc gatctcacga tacacccgt    4800 gcgcggtggc aatcgcccag cggagcgca ggggcagatc ccccagcccg caagcgctg    4860 actgataata gggctcagcc tcggtcacca gccgcgctgc cagacgcgcc agcgccggac    4920
ggttggcccg cacggtgcag gtctgttcat tgagtccgac ttccgccagc cactgctgcg    4980
gcaggtagca gcgtcccacc tgcgcatcgt caacgatatc cctggcgata ttggtgagct    5040
gaaaggcaat gcccagatcg caggcgcgat ccagcgtggc ttcgtcccgc actcccatca    5100
ccctggccat catcaggccg accacgcccg ccacgtgata acagtagcgg agcgtatcat    5160
cgaggctgta atagcgctcg ttgcgcacgt ccatcgcata gccttccagg tggtcgaagg    5220
cctgagtagg cggaatggca tgggcgaggg caacctcctg aaaggcggcg aacggcggct    5280
cttgcatggt ttccccgtcg taggcgcggc gcgtcatctt acgcagccgt tgcaggcgcg    5340
cctcgggcgt gtcgctctgc tcggtcgggg cagcaaaacc caccacctgt ccgtcgataa    5400
catcgtcgca gtagcggcac caggtataga gcatcagcgc gctgcgccgg gtgcgtttgt    5460
caaacagctt tgaggcggtg gcgaaacttt tagaaccggc ggtcatggtg gcgctggcgt    5520
gttcgagaag cggctgggac attacgctaa atcctttaac attaactggg ccgttgcctt    5580
ggcggatccg atcacgcccg gcacgccagc gccgggatgc gttccggcgc cgaccaggta    5640
gaggttatca accacgctgt cgcggttgtg cggccggaac caggcgctct gggtgaggat    5700
cggctccagt gaaaacgctg acccctgcca ggcatcgagc gtatcgcgaa aatcttccgg    5760
cgtgaacatg cggtgcgtca ccagctggga gcgcagcccc ggcatatagc gcgcttcgag    5820
ataatcaaaa atgcgatccc gcagacgcgg cccttccacg ctccagtcga gcgggcgtt    5880 accgaggtgc ggcaccggcg cgagcacata gtagctgccg caccccgcg gggcagcga    5940 cgggtcggtt acgcagggcg catgcagata gagcgaaaaa tcttccgaca gggtgtcggc    6000
gctgaaaatt tcatcgatta gcgctttata acgcgggcca aagcagacgg tatggtgcgc    6060
cagctgggtg tgatggtgat ccaggccaaa atagagcacg aacagcgagt tgctcatgcg    6120
cttgcgtttc agcttttttgg ccgtagcggc gccgtgcggg tgatggccga gcagtcgggc    6180
ataggtattt accacgtccg cgttcgaggc caccgccgca gcctccagcc gctgcccgtt    6240
aaccagatgc acggccttca cctgattgtc caccgtctcc agccgctcaa cctgagcgtt    6300
aagggtgagg gtgccgccaa gatcctgaaa cagcttcacc atgccctgaa ccagcgcacc    6360
ggtgccgccg cgcgggaacc agacgcccca ttcccgctcc agggcgtgga tcagggtgta    6420
aatagaagac gtggagaacg ggttgccgcc caccagcagc gagtgaaacg aaaatgcctg    6480
ccgcaggtgc tcgtcttcca cgtaggccga cactttgtcg tacacgctgc gccatgcctg    6540
cagccgcgcc agttgaggac cggcgcgcag catgtcgcga aacgagagaa acggcaccgc    6600
gccgagcttc agatagcctt cggcaaacac cgcccgggag tagtcgagga agcggtgata    6660
gcccgccacg tcgttcgggt taaacgcggc gatctgcgac tcaagcgccg cctgatcgtt    6720
ggcgtagtcg aaaaccttgc cgtcttccca gcacaggcga tagaacggcg tcaccggcat    6780
```

```
cagctcaacg tagtccttca gccgttttcc ggcgagggtg aacagctcct caatggcgga    6840
gggatcggtg atgacggtgg gacccgcatc aaaggtaaag ccgcgatctt cgtagacata    6900
ggcgcggccg ccgggtttgt cgcggctctc cagcagcgtg gtaggaatgc ccgccgcctg    6960
gaggcgaatc gccagcgcca gtccgccgaa cccggcgcca attacaatgg tttgtttcat    7020
ttatgatggg ctcgcagaga agaatgagtg tggagcaggg cttttgatcgc cccgacaatc    7080 ggcaccggcg gtttgccaag cagcaggcgc gcgcggtcgg cggagcgaag ctggccggca    7140
taaaaacggg cgatcagctg ctcgtcaagc tggtaaaacc gctgcatcac gcgccagcgc    7200
tggtcgggtg tgccggccag gaaaagcatg cggttaagca ggcggaaaaa gcgttgtgtc    7260
tgccagtggc gcgccgcgaa atcggcgatc agctgataga gcgcgccctg atgcagtccc    7320
ggcgcgttgg caatgcggtc cgccagccga accgccagcg cagcgaata ccggtggtg    7380 gcatggaaca gaccggcgcg caggccgctg accggctgat gatggaactg gtgccagaag    7440
gcggccggat cgccggacag ggtgatcggc agcgccccct gttcctcacg caccagccgc    7500
gcaagctgcc agccctgctg gcgggcgtaa tcggcaatcc gcgcgcgggc tgaatcggcg    7560
tcgagcgtcg ggccgtcaat gtagtgcgtg tcttcgataa gcagggtgtc ggcgctgagc    7620
ggcagggtat agacaaagcg gtagccgttg ccctgggcga cgcgggcatc catcaggatc    7680
gggcgcgtta cccgtgggg cgcggtcagt tgccactcct ggccgatgaa cgcctgatag    7740
ccaatgctga ggtgcggcga gggctgatag ccgcggccat caataccgc cccggcggta    7800 aagcgtcgtc cgtcgctgag ggttacttcc tgcccgctca cccgtgacac ggtcacgttt    7860
gtcagcaaat tctctttcat cagcccgcgc atcgcttggg caaaacgcgt ggaggtgatg    7920
gtcaggtagc cgtcatgcag ggtgcgcgac acgttcggaa agtggacgtc gtacccgtcc    7980
cagcgatggg ccaccagcgg cgccagccag gcgtgctggg ctggcgtgat atcgtgttgg    8040
tgaaaggacc aggtgtggtt tccgccgggc gcgtcgccgc actccagcat taatacagca    8100
agcgtcggat gacgctgctt tagtcgccag gcgataagcc cgttggccag cccgcgccg    8160 accagaatca gatcccattt tttcataccg ctccccggta taaggcaccg tactgcgtca    8220
cagggatgcg ccgccgttga ccggaagcag cgtggcgtgt cgcaacgcct gcaggtttgc    8280
actgccggta cagaaacagg cgatccgcag ctgcgtaatc agggtgcgga aatgggcaat    8340
tgccgcgtcg ccggaggcgt tggcatgcgc cagcaccgcc gcggcctggc ccaccagatc    8400
tgcacccagc gcgatggctt ttgctgcgtc aatgccgttg gcgatgccgc cggaggcgat    8460
aagcgggata tcaggcagcg caagatggac gcgacgcagc gcatcggcag taggaatgcc    8520
ccagtcggca aaggccatcg ccacatttcg cgcctcgggg gtcggggcgc gttcagcttc    8580
caccgccgcc cagctggttc cgcccgcgcc ggcaatgtcg atcatcgcca cgccgacgtc    8640
cgccagtcgg caggcaacgt ccggggagat cccggcgccc acctctttaa ccaccaccgg    8700
taccggcagg tcgcgcacca gctgcgcaat ggcgttgagg atgccgcgcc agtcgcgatc    8760
gccgccgccc tggagcgcct cctgcagcgg gttcagatgc acaattaacg cgtcggcgtc    8820
gatcatgtcc accgcgcgcc gggcgtagtc cagcccctgc gcaccgcgga tctgcgccgc    8880
gccaaggtta gccagcagcg gcacgtccgg ggcgatatgg cgtagctggg catccagccc    8940
gtgctgcgcg ccgtcctcca gcgccacgcg ctgggaaccg acgcccatcg ccagcccaag    9000
ggtttgcgcc gcctgggcca gatgacggtt aatgtctctg gcgcgcgccg cgccgccggt    9060
catggagctg atcagcaccg gggctttcag cgggcgggaa aacagggtgg tggagagatc    9120
```

```
gataccgtcg agatccagct ccgggagggc gcagtgttca aaacgccagg cgtcaaatcc    9180
ggtgcgaatg gtactcatcg cccggtcagg gtgcagcacg atatccaggt ggtcattttt    9240
acgctgaacc agatgcgcgt ccttcatgtg atctccacaa atattaccgg ggtgtatccg    9300
ttgctcagct aaacgcggcc agctgttttg aaaaccaggc gtgcataaag cgtcgcgtgg    9360
cctggttttt tccgcaggcg cgtgaaaaat gggcgtctgc gcggcgcaga tgggtgtcga    9420
gccgctcgcg caccgcgtcg ctgccgagca tcgccaccag cgtggactta cccgcgtcct    9480
tattgatgtc tttgccggtc ccggcatggc cgtccgccag atcgtccagc agctggaacg    9540
cctggcctaa atcctgcgca aagcagcgca ttttctggcg cgccgccggc gaggcgcctg    9600
ccgccagggc cgcgatttgc agcgtggcac caaacagcac gctggttttc agttcgttgg    9660
tggtggcgat ctcctcggcg ctgcgcgggg cggtgccttc acgcagatcc ttatactgac    9720
cctgcaccag accctgggta ccgaccgcca tcgacagctc cgccaccgcc tggctgcggc    9780
actcgggaga caatccctgc gccgcgacca tcacgccaaa ggcgctgctg agcaacgcta    9840
ccgcagcgag aattgccacg tcttcaccat actggcgatg aatggtaggg cgaccgcgcc    9900
ggagcgccgc gttatccatg cagggaatat cgtcgaggat cagcgacgag gcgtgcacca    9960
tttccaccgc acaggccata tccagcaggc cggggtggtc gcgatcgcag ccgaggtcgc   10020
gggcggcgag gatcaggagc agcgggcgaa tgcgtttccc cggtgccagt acgccttcgc   10080
gcattgcgct gctgacccga tcccgctcat cgccaacggg cagcagttca tccaggcgac   10140
gttgcagggc agcgtgcagc tcatgcagtt ccccgtcgtg accgggatgt gtttcaaagg   10200
gtcttgtcat ggttggtacc cggcgtctcg actagagcct aggttatttc cggcgcgaag   10260
caggcgatgg cttcccggaa ggcgagctgg ccgccgcgcg atccgcacct ctggcagcgc   10320
ccgcgctagc gggtctgccg ttacgttcgc gcagcaccgc ctgcagcttg tccaccggtg   10380
gggcgtagat aaacccgaag gagacgcacc cttcgcgccc ccgcaccgcg tgatgcagcc   10440
ggtgtgccat gtagaggcgg cgcagatagc gcgcgcgcgg cacgtaacgg aacgccagc   10500 gctggtggac taaaccatcg tgaacgataa agtagatcac gccgtagccg gtcattcccg   10560
cgccaatcca ctgaagcggc cagtacccctt cgctgcccgc gtaaatcagc gcaatggcca   10620
gtagcgcaaa caccaccgca tagagatcgt tacgctcaaa cgccccttttg cgcggggtat   10680 ggtgcgaatg atgccagccc catccccagc cgtgcatgat gtacttgtgt gcgaacgttg   10740
ccaccccttc catgatgatg atagtcagta gcacgatccc ggtattccac aacgcaagca   10800
tggtttattc ctccttacta gtgaattccg gatgagcatt catcaggcgg gcaagaatgt   10860
gaataaaggc cggataaaac ttgtgcttat ttttctttac ggtctttaaa aaggccgtaa   10920
tatccagctg aacggtctgg ttataggtac attgagcaac tgactgaaat gcctcaaaat   10980
gttctttacg atgccattgg gatatatcaa cggtggtata ccagtgatt ttttttctcca   11040 ttttagcttc cttagctcct gaaaatctcg ataactcaaa aaatacgccc ggtagtgatc   11100
ttatttcatt atggtgaaag ttggaacctc ttacgtgccg atcaacgtct cattttcgcc   11160
aaaagttggc ccagggcttc ccggtatcaa cagggacacc aggatttatt tattctgcga   11220
agtgatcttc cgtcacaggt atttattcgg cgcaaagggc ctcgtgatac gcctattttt   11280
ataggttaat gtcatgataa taatggtttc ttagacgtca ggtggcactt tcgggaaa    11340 tgtgcgcgcc cgcgttcctg ctggcgctgg gcctgtttct ggcgctggac ttcccgctgt   11400
tccgtcagca gcttttcgcc cacggccttg atgatcgcgg cggccttggc ctgcatatcc   11460
cgattcaacg gccccagggc gtccagaacg ggcttcaggc gctcccgaag gt           11512
```

<210> SEQ ID NO 8
<211> LENGTH: 558
<212> TYPE: DNA
<213> ORGANISM: Pantoea agglomerans DC404
<220> FEATURE:
<221> NAME/KEY: CDS
<222> LOCATION: (1)..(558)

<400> SEQUENCE: 8

| | | | | | | | | | | | | | | | | |
|---|---|---|---|---|---|---|---|---|---|---|---|---|---|---|---|---|
| atg | ctt | gcg | ttg | tgg | aat | acc | ggg | atc | gtg | cta | ctg | act | atc | atc | atc | 48 |
| Met | Leu | Ala | Leu | Trp | Asn | Thr | Gly | Ile | Val | Leu | Leu | Thr | Ile | Ile | Ile | |
| 1 | | | | 5 | | | | | 10 | | | | | 15 | | |
| atg | gaa | ggg | gtg | gca | acg | ttc | gca | cac | aag | tac | atc | atg | cac | ggc | tgg | 96 |
| Met | Glu | Gly | Val | Ala | Thr | Phe | Ala | His | Lys | Tyr | Ile | Met | His | Gly | Trp | |
| | | | 20 | | | | | 25 | | | | | 30 | | | |
| gga | tgg | ggc | tgg | cat | cat | tcg | cac | cat | acc | ccg | cgc | aaa | ggg | gcg | ttt | 144 |
| Gly | Trp | Gly | Trp | His | His | Ser | His | His | Thr | Pro | Arg | Lys | Gly | Ala | Phe | |
| | 35 | | | | | 40 | | | | | 45 | | | | | |
| gag | cgt | aac | gat | ctc | tat | gcg | gtg | gtg | ttt | gcg | cta | ctg | gcc | att | gcg | 192 |
| Glu | Arg | Asn | Asp | Leu | Tyr | Ala | Val | Val | Phe | Ala | Leu | Leu | Ala | Ile | Ala | |
| 50 | | | | | 55 | | | | | 60 | | | | | | |
| ctg | att | tac | gcg | ggc | agc | gaa | ggg | tac | tgg | ccg | ctt | cag | tgg | att | ggc | 240 |
| Leu | Ile | Tyr | Ala | Gly | Ser | Glu | Gly | Tyr | Trp | Pro | Leu | Gln | Trp | Ile | Gly | |
| 65 | | | | | 70 | | | | | 75 | | | | | 80 | |
| gcg | gga | atg | acc | ggc | tac | ggc | gtg | atc | tac | ttt | atc | gtt | cac | gat | ggt | 288 |
| Ala | Gly | Met | Thr | Gly | Tyr | Gly | Val | Ile | Tyr | Phe | Ile | Val | His | Asp | Gly | |
| | | | | 85 | | | | | 90 | | | | | 95 | | |
| tta | gtc | cac | cag | cgc | tgg | ccg | ttc | cgt | tac | gtg | ccg | cgc | cgc | ggc | tat | 336 |
| Leu | Val | His | Gln | Arg | Trp | Pro | Phe | Arg | Tyr | Val | Pro | Arg | Arg | Gly | Tyr | |
| | | | 100 | | | | | 105 | | | | | 110 | | | |
| ctg | cgc | cgc | ctc | tac | atg | gca | cac | cgg | ctg | cat | cac | gcg | gtg | cgg | ggg | 384 |
| Leu | Arg | Arg | Leu | Tyr | Met | Ala | His | Arg | Leu | His | His | Ala | Val | Arg | Gly | |
| | | 115 | | | | | 120 | | | | | 125 | | | | |
| cgc | gaa | ggg | tgc | gtc | tcc | ttc | ggg | ttt | atc | tac | gcc | cca | ccg | gtg | gac | 432 |
| Arg | Glu | Gly | Cys | Val | Ser | Phe | Gly | Phe | Ile | Tyr | Ala | Pro | Pro | Val | Asp | |
| | 130 | | | | | 135 | | | | | 140 | | | | | |
| aag | ctg | cag | gcg | gtg | ctg | cgc | gaa | cgt | aac | ggc | aga | ccc | gct | agc | gcg | 480 |
| Lys | Leu | Gln | Ala | Val | Leu | Arg | Glu | Arg | Asn | Gly | Arg | Pro | Ala | Ser | Ala | |
| 145 | | | | | 150 | | | | | 155 | | | | | 160 | |
| ggc | gct | gcc | aga | ggt | gcg | gat | cgc | gcg | gcg | gcc | agc | tcg | cct | tcc | ggg | 528 |
| Gly | Ala | Ala | Arg | Gly | Ala | Asp | Arg | Ala | Ala | Ala | Ser | Ser | Pro | Ser | Gly | |
| | | | | 165 | | | | | 170 | | | | | 175 | | |
| aag | cca | tcg | cct | gct | tcg | cgc | cgg | aaa | taa | | | | | | | 558 |
| Lys | Pro | Ser | Pro | Ala | Ser | Arg | Arg | Lys | | | | | | | | |
| | | | 180 | | | | | 185 | | | | | | | | |

<210> SEQ ID NO 9
<211> LENGTH: 185
<212> TYPE: PRT
<213> ORGANISM: Pantoea agglomerans DC404

<400> SEQUENCE: 9

Met Leu Ala Leu Trp Asn Thr Gly Ile Val Leu Leu Thr Ile Ile Ile
1               5                   10                  15

Met Glu Gly Val Ala Thr Phe Ala His Lys Tyr Ile Met His Gly Trp
                20                  25                  30

Gly Trp Gly Trp His His Ser His His Thr Pro Arg Lys Gly Ala Phe
            35                  40                  45

Glu Arg Asn Asp Leu Tyr Ala Val Val Phe Ala Leu Leu Ala Ile Ala
        50                  55                  60

```
Leu Ile Tyr Ala Gly Ser Glu Gly Tyr Trp Pro Leu Gln Trp Ile Gly
 65                  70                  75                  80

Ala Gly Met Thr Gly Tyr Gly Val Ile Tyr Phe Ile Val His Asp Gly
                 85                  90                  95

Leu Val His Gln Arg Trp Pro Phe Arg Tyr Val Pro Arg Arg Gly Tyr
            100                 105                 110

Leu Arg Arg Leu Tyr Met Ala His Arg Leu His Ala Val Arg Gly
        115                 120                 125

Arg Glu Gly Cys Val Ser Phe Gly Phe Ile Tyr Ala Pro Pro Val Asp
    130                 135                 140

Lys Leu Gln Ala Val Leu Arg Glu Arg Asn Gly Arg Pro Ala Ser Ala
145                 150                 155                 160

Gly Ala Ala Arg Gly Ala Asp Arg Ala Ala Ser Ser Pro Ser Gly
                165                 170                 175

Lys Pro Ser Pro Ala Ser Arg Arg Lys
            180                 185

<210> SEQ ID NO 10
<211> LENGTH: 43
<212> TYPE: DNA
<213> ORGANISM: artificial sequence
<220> FEATURE:
<223> OTHER INFORMATION: primer

<400> SEQUENCE: 10
actagtaagg aggaataaac catgcttgcg ttgtggaata ccg                    43

<210> SEQ ID NO 11
<211> LENGTH: 30
<212> TYPE: DNA
<213> ORGANISM: artificial sequence
<220> FEATURE:
<223> OTHER INFORMATION: primer

<400> SEQUENCE: 11
tctagagcct aggttatttc cggcgcgaag                                   30

<210> SEQ ID NO 12
<211> LENGTH: 36
<212> TYPE: DNA
<213> ORGANISM: artificial sequence
<220> FEATURE:
<223> OTHER INFORMATION: primer

<400> SEQUENCE: 12
ctgaaatgag ctgctgacaa ttaatcatcc ggctcg                            36

<210> SEQ ID NO 13
<211> LENGTH: 36
<212> TYPE: DNA
<213> ORGANISM: artificial sequence
<220> FEATURE:
<223> OTHER INFORMATION: primer

<400> SEQUENCE: 13
cgagccggat gattaattgt cagcagctca tttcag                            36

<210> SEQ ID NO 14
<211> LENGTH: 796
<212> TYPE: DNA
<213> ORGANISM: Sphingomonas melonis DC18
<220> FEATURE:
```

```
<221> NAME/KEY: RBS
<222> LOCATION: (19)..(31)
<223> OTHER INFORMATION: Wild type ribosomal binding site

<400> SEQUENCE: 14
ccatggccct ttctagaaag gaggaataaa catgaccgtc gatcacgacg cacggatcag      60
cctgctgctg gccgcagcca tcggcgccgc gtggctggcg atccatgtcg ggcgatcgt     120 gtggtggcga tggagcccgg cgacggcggt gctcgcgatc cccgtcgtgc tcgtacaggc     180
gtggctgagc accggcctgt tcatcgtcgc gcacgattgc atgcacggat cgttcgtgcc     240
cggccggccc gcggtcaacc ggaccgtcgg gacgctgtgc ctcggcgcct atgcgggact     300
gtcctatggc cagctccatc ccaagcatca tgcgcatcac gatgcgccgg gcaccgccgc     360
cgaccccgat ttccatgccg gcgcgccgcg atccgcactg ccgtggttcg cgcgcttctt     420
caccagctat tacacgcacg gccagatcct ccggatcacc gcggcggcgg tgctgtacat     480
gctgctcggt gtgtcgctgc tcaacatcgt cgtgttctgg gcgttgccgg cgctgatcgc     540
gctggcgcag ctgttcgtct tcggcacctt cctgccgcat cgccacggcg acacgccgtt     600
cgcggacgcg cacaatgccc gcagcaacgg ctggccacgg ctggcgtcgc tggcgacctg     660
cttccacttc ggcgcctatc atcacgaaca tcacctgagc ccgtggacgc cctggtggca     720
gttgccgcgc gtcggccagc ctgccgccgg acaccggtcg ttaagcaaag accggtagac     780
tagtaagggc gaattc                                                    796

<210> SEQ ID NO 15
<211> LENGTH: 22
<212> TYPE: DNA
<213> ORGANISM: artificial sequence
<220> FEATURE:
<223> OTHER INFORMATION: primer

<400> SEQUENCE: 15
tatcatcgac tgcacggtgc ac                                              22

<210> SEQ ID NO 16
<211> LENGTH: 22
<212> TYPE: DNA
<213> ORGANISM: artificial sequence
<220> FEATURE:
<223> OTHER INFORMATION: primer

<400> SEQUENCE: 16
tcctactcag gagagcgttc ac                                              22

<210> SEQ ID NO 17
<211> LENGTH: 796
<212> TYPE: DNA
<213> ORGANISM: Sphingomonas melonis DC18
<220> FEATURE:
<221> NAME/KEY: RBS
<222> LOCATION: (19)..(31)
<223> OTHER INFORMATION: Mutant RBS with a28t substitution.
<220> FEATURE:
<221> NAME/KEY: CDS
<222> LOCATION: (32)..(778)

<400> SEQUENCE: 17
ccatggccct ttctagaaag gaggaattaa c atg acc gtc gat cac gac gca        52
                                   Met Thr Val Asp His Asp Ala
                                    1               5 cgg atc agc ctg ctg ctg gcc gca gcc atc ggc gcc gcg tgg ctg gcg      100
Arg Ile Ser Leu Leu Leu Ala Ala Ala Ile Gly Ala Ala Trp Leu Ala
```

```
                10                  15                  20
atc cat gtc ggg gcg atc gtg tgg tgg cga tgg agc ccg gcg acg gcg      148
Ile His Val Gly Ala Ile Val Trp Trp Arg Trp Ser Pro Ala Thr Ala
     25                  30                  35 gtg ctc gcg atc ccc gtc gtg ctc gta cag gcg tgg ctg agc acc ggc      196
Val Leu Ala Ile Pro Val Val Leu Val Gln Ala Trp Leu Ser Thr Gly
 40                  45                  50                  55 ctg ttc atc gtg gcg cac gat tgc atg cac gga tcg ttc gtg ccc ggc      244
Leu Phe Ile Val Ala His Asp Cys Met His Gly Ser Phe Val Pro Gly
                 60                  65                  70 cgg ccc gcg gtc aac cgg acc gtc ggg acg ctg tgc ctc ggc gcc tat      292
Arg Pro Ala Val Asn Arg Thr Val Gly Thr Leu Cys Leu Gly Ala Tyr
             75                  80                  85 gcg gga ctg tcc tat ggc cag ctc cat ccc aag cat cat gcg cat cac      340
Ala Gly Leu Ser Tyr Gly Gln Leu His Pro Lys His His Ala His His
         90                  95                 100 gat gcg ccg ggc acc gcc gcc gac ccc gat ttc cat gcc ggc gcg ccg      388
Asp Ala Pro Gly Thr Ala Ala Asp Pro Asp Phe His Ala Gly Ala Pro
    105                 110                 115 cga tcc gca ctg ccg tgg ttc gcg cgc ttc ttc acc agc tat tac acg      436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gtg ctg tac atg ctg      484
His Gly Gln Ile Leu Arg Ile Thr Ala Ala Ala Val Leu Tyr Met Leu
                140                 145                 150 ctc ggt gtg tcg ctg ctc aac atc gtc gtg ttc tgg gcg ttg ccg gcg      532
Leu Gly Val Ser Leu Leu Asn Ile Val Val Phe Trp Ala Leu Pro Ala
            155                 160                 165 ctg atc gcg ctg gcg cag ctg ttc gtc ttc ggc acc ttc ctg ccg cat      580
Leu Ile Ala Leu Ala Gln Leu Phe Val Phe Gly Thr Phe Leu Pro His
        170                 175                 180 cgc cac ggc gac acg ccg ttc gcg gac gcg cac aat gcc cgc agc aac      628
Arg His Gly Asp Thr Pro Phe Ala Asp Ala His Asn Ala Arg Ser Asn
    185                 190                 195 ggc tgg cca cgg ctg gcg tcg ctg gtg acc tgc ttc cac ttc ggc gcc      676
Gly Trp Pro Arg Leu Ala Ser Leu Val Thr Cys Phe His Phe Gly Ala
200                 205                 210                 215 tat cat cac gaa cat cac ctg agc ccg tgg acg ccc tgg tgg cag ttg      724
Tyr His His Glu His His Leu Ser Pro Trp Thr Pro Trp Trp Gln Leu
                220                 225                 230 ccg cgc gtc ggc cag cct gcc gcc gga cgc cgg tcg tta agc aaa gac      772
Pro Arg Val Gly Gln Pro Ala Ala Gly Arg Arg Ser Leu Ser Lys Asp
            235                 240                 245 cgg tag actagtaagg gcgaattc                                          796
Arg

<210> SEQ ID NO 18
<211> LENGTH: 248
<212> TYPE: PRT
<213> ORGANISM: Sphingomonas melonis DC18

<400> SEQUENCE: 18

Met Thr Val Asp His Asp Ala Arg Ile Ser Leu Leu Ala Ala Ala
  1               5                  10                  15

Ile Gly Ala Ala Trp Leu Ala Ile His Val Gly Ala Ile Val Trp Trp
                 20                  25                  30

Arg Trp Ser Pro Ala Thr Ala Val Leu Ala Ile Pro Val Val Leu Val
             35                  40                  45

Gln Ala Trp Leu Ser Thr Gly Leu Phe Ile Val Ala His Asp Cys Met
```

-continued

```
                    50                  55                  60
His Gly Ser Phe Val Pro Gly Arg Pro Ala Val Asn Arg Thr Val Gly
 65                  70                  75                  80

Thr Leu Cys Leu Gly Ala Tyr Ala Gly Leu Ser Tyr Gly Gln Leu His
                 85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125

Phe Phe Thr Ser Tyr Tyr Thr His Gly Gln Ile Leu Arg Ile Thr Ala
    130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Ala His Asn Ala Arg Ser Asn Gly Trp Pro Arg Leu Ala Ser Leu Val
        195                 200                 205

Thr Cys Phe His Phe Gly Ala Tyr His His Glu His His Leu Ser Pro
    210                 215                 220

Trp Thr Pro Trp Trp Gln Leu Pro Arg Val Gly Gln Pro Ala Ala Gly
225                 230                 235                 240

Arg Arg Ser Leu Ser Lys Asp Arg
                245

<210> SEQ ID NO 19
<211> LENGTH: 796
<212> TYPE: DNA
<213> ORGANISM: Sphingomonas melonis DC18
<220> FEATURE:
<221> NAME/KEY: CDS
<222> LOCATION: (32)..(778)

<400> SEQUENCE: 19
ccatggccct ttctagaaag gaggaataaa c atg acc gtc gat cac gac gca         52
                                  Met Thr Val Asp His Asp Ala
                                   1               5 cgg atc agc ctg ctg ctg gcc gca gcc atc ggc gcc gcg tgg ctg gcg       100
Arg Ile Ser Leu Leu Leu Ala Ala Ala Ile Gly Ala Ala Trp Leu Ala
            10                  15                  20 atc cat gtc ggg gcg atc gtg tgg tgg cga tgg agc ccg gcg acg gcg       148
Ile His Val Gly Ala Ile Val Trp Trp Arg Trp Ser Pro Ala Thr Ala
 25                  30                  35 gtg ctc gcg atc ccc gtc gtg ctc gta cag gcg tgg ctg agc acc ggc       196
Val Leu Ala Ile Pro Val Val Leu Val Gln Ala Trp Leu Ser Thr Gly
 40                  45                  50                  55 ctg ttc atc gtc gcg cac gat tgc atg cac gga tcg ttc gtg ccc ggc       244
Leu Phe Ile Val Ala His Asp Cys Met His Gly Ser Phe Val Pro Gly
                 60                  65                  70 cgg ccc gcg gtc aac cgg acc gtc ggg acg ctg tgc ctc ggc gcc tat       292
Arg Pro Ala Val Asn Arg Thr Val Gly Thr Leu Cys Leu Gly Ala Tyr
             75                  80                  85 gcg gga ctg tcc tat ggc cag ctc cat ccc aag cat cat gcg cat cac       340
Ala Gly Leu Ser Tyr Gly Gln Leu His Pro Lys His His Ala His His
         90                  95                 100 gat gcg ccg ggc acc gcc gcc gac ccc gat ttc cat gcc ggc gcg ccg       388
Asp Ala Pro Gly Thr Ala Ala Asp Pro Asp Phe His Ala Gly Ala Pro
```

```
                105                 110                 115
cga tcc gca ctg ccg tgg ttc gcg cgc ttc ttc acc agc tat tac acg    436
Arg Ser Ala Leu Pro Trp Phe Ala Arg Phe Phe Thr Ser Tyr Tyr Thr
120             125                 130                 135 cac ggc cag atc ctc cgg atc acc gcg gcg gtg ctg tac atg ctg        484
His Gly Gln Ile Leu Arg Ile Thr Ala Ala Val Leu Tyr Met Leu
            140                 145                 150 ctc ggt gtg tcg ctg ctc aac atc gtc gtg ttc tgg gcg ttg ccg gcg    532
Leu Gly Val Ser Leu Leu Asn Ile Val Val Phe Trp Ala Leu Pro Ala
                155                 160                 165 ctg atc gcg ctg gcg cag ctg ttc gtc ttc ggc acc ttc ctg ccg cat    580
Leu Ile Ala Leu Ala Gln Leu Phe Val Phe Gly Thr Phe Leu Pro His
            170                 175                 180 cgc cac ggc gac acg ccg ttc gcg gac gcg cac aat gcc cgc agc aac    628
Arg His Gly Asp Thr Pro Phe Ala Asp Ala His Asn Ala Arg Ser Asn
        185                 190                 195 ggc tgg cca cgg ctg gcg tcg ctg gcg acc tgc ttc cac ctc ggc gcc    676
Gly Trp Pro Arg Leu Ala Ser Leu Ala Thr Cys Phe His Leu Gly Ala
200                 205                 210                 215 tat cat cac gaa cat cac ctg agc ccg tgg acg ccc tgg tgg cag ttg    724
Tyr His His Glu His His Leu Ser Pro Trp Thr Pro Trp Trp Gln Leu
                220                 225                 230 ccg cgc gtc ggc cag cct gcc gcc gga cac cgg tcg tta agc aaa gac    772
Pro Arg Val Gly Gln Pro Ala Ala Gly His Arg Ser Leu Ser Lys Asp
            235                 240                 245 cgg tag actagtaagg gcgaattc                                        796
Arg

<210> SEQ ID NO 20
<211> LENGTH: 248
<212> TYPE: PRT
<213> ORGANISM: Sphingomonas melonis DC18

<400> SEQUENCE: 20

Met Thr Val Asp His Asp Ala Arg Ile Ser Leu Leu Ala Ala Ala
1               5                   10                  15

Ile Gly Ala Ala Trp Leu Ala Ile His Val Gly Ala Ile Val Trp Trp
            20                  25                  30

Arg Trp Ser Pro Ala Thr Ala Val Leu Ala Ile Pro Val Val Leu Val
        35                  40                  45

Gln Ala Trp Leu Ser Thr Gly Leu Phe Ile Val Ala His Asp Cys Met
    50                  55                  60

His Gly Ser Phe Val Pro Gly Arg Pro Ala Val Asn Arg Thr Val Gly
65              70                  75                  80

Thr Leu Cys Leu Gly Ala Tyr Ala Gly Leu Ser Tyr Gly Gln Leu His
                85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125

Phe Phe Thr Ser Tyr Tyr Thr His Gly Gln Ile Leu Arg Ile Thr Ala
    130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
```

```
                180              185              190
Ala His Asn Ala Arg Ser Asn Gly Trp Pro Arg Leu Ala Ser Leu Ala
            195                  200                  205

Thr Cys Phe His Leu Gly Ala Tyr His His Glu His His Leu Ser Pro
    210                  215                  220

Trp Thr Pro Trp Trp Gln Leu Pro Arg Val Gly Gln Pro Ala Ala Gly
225                  230                  235                  240

His Arg Ser Leu Ser Lys Asp Arg
                245

<210> SEQ ID NO 21
<211> LENGTH: 796
<212> TYPE: DNA
<213> ORGANISM: Sphingomonas melonis DC18

<400> SEQUENCE: 21
ccatggccct ttctagaaag gaggaataaa catgaccgtc gatcacgacg cacggatcag      60
cctgctgctg gccgcagcca tcggcgccgc gtggctggcg atccatgtcg gggcgatcgt     120
gtggtggcga tggagcccgg cgacggcggt gctcgcgatc cccgtcgtgc tcgtacaggc     180
gtggctgagc accggcctgt tcatcgtcgc gcacgattgc atgcacggat cgttcgtgcc     240
cggccggccc gcggtcaacc ggaccgtcgg gacgctgtgc ctcggcgcct atgcgggact     300
gtcctatggc cagctccatc ccaagcatca tgcgcatcac gatgcgccgg gcaccgccgc     360
cgaccccgat ttccatgccg gcgcgccgcg atccgcactg ccgtggttcg cgcgcttctt     420
caccagctat tacacgcacg gccagatcct ccggatcacc gcggcggcgg tgctgtacat     480
gctgctcggt gtgtcgctgc tcaacatcgt cgtgttctgg gcgttgccgg cgctgatcgc     540
gctggcgcag ctgttcgtct tcggcacctt cctgccgcat cgccacggcg acacgccgtt     600
cgcggacgcg cacaatgccc gcagcaacgg ctggccacgg ctggcgtcgc tggcgacctg     660
cttccacttg ggcgcctatc atcacgaaca tcacctgagc ccgtggacgc cctggtggca     720
gttgccgcgc gtcggccagc ctgccgccgg acaccggtcg ttaagcaaag accggtagac     780
tagtaagggc gaattc                                                    796

<210> SEQ ID NO 22
<211> LENGTH: 796
<212> TYPE: DNA
<213> ORGANISM: Sphingomonas melonis DC18

<400> SEQUENCE: 22
ccatggccct ttctagaaag gaggaataaa catgaccgtc gatcacgacg cacggatcag      60
cctgctgctg gccgcagcca tcggcgccgc gtggctggcg atccatgtcg gggcgatcgt     120
gtggtggcga tggagcccgg cgacggcggt gctcgcgatc cccgtcgtgc tcgtacaggc     180
gtggctgagc accggcctgt tcatcgtcgc gcacgattgc atgcacggat cgttcgtgcc     240
cggccggccc gcggtcaacc ggaccgtcgg gacgctgtgc ctcggcgcct atgcgggact     300
gtcctatggc cagctccatc ccaagcatca tgcgcatcac gatgcgccgg gcaccgccgc     360
cgaccccgat ttccatgccg gcgcgccgcg atccgcactg ccgtggttcg cgcgcttctt     420
caccagctat tacacgcacg gccagatcct ccggatcacc gcggcggcgg tgctgtacat     480
gctgctcggt gtgtcgctgc tcaacatcgt cgtgttctgg gcgttgccgg cgctgatcgc     540
gctggcgcag ctgttcgtct tcggcacctt cctgccgcat cgccacggcg acacgccgtt     600
cgcggacgcg cacaatgccc gcagcaacgg ctggccacgg ctggcgtcgc tggcgacctg     660
```
cttccactta ggcgcctatc atcacgaaca tcacctgagc ccgtggacgc cctggtggca    720
gttgccgcgc gtcggccagc ctgccgccgg acaccggtcg ttaagcaaag accggtagac    780
tagtaagggc gaattc                                                    796

<210> SEQ ID NO 23
<211> LENGTH: 796
<212> TYPE: DNA
<213> ORGANISM: Sphingomonas melonis DC18

<400> SEQUENCE: 23
ccatggccct ttctagaaag gaggaataaa catgaccgtc gatcacgacg cacggatcag     60
cctgctgctg gccgcagcca tcggcgccgc gtggctggcg atccatgtcg ggcgatcgt    120 gtggtggcga tggagcccgg cgacggcggt gctcgcgatc cccgtcgtgc tcgtacaggc    180
gtggctgagc accggcctgt tcatcgtcgc gcacgattgc atgcacggat cgttcgtgcc    240
cggccggccc gcggtcaacc ggaccgtcgg gacgctgtgc ctcggcgcct atgcgggact    300
gtcctatggc cagctccatc ccaagcatca tgcgcatcac gatgcgccgg gcaccgccgc    360
cgaccccgat ttccatgccg gcgcgccgcg atccgcactg ccgtggttcg cgcgcttctt    420
caccagctat tacacgcacg gccagatcct ccggatcacc gcggcggcgg tgctgtacat    480
gctgctcggt gtgtcgctgc tcaacatcgt cgtgttctgg gcattgccgg cgctgatcgc    540
gctggcgcag ctgttcgtct tcggcaccct cctgccgcat cgccacggcg acacgccgtt    600
cgcggacgcg cacaatgccc gcagcaacgg ctggccacgg ctggcgtcgc tggcgacctg    660
cttccacctc ggcgcctatc atcacgaaca tcacctgagc ccgtggacgc cctggtggca    720
gttgccgcgc gtcggccagc ctgccgccgg acaccggtcg ttaagcaaag accggtagac    780
tagtaagggc gaattc                                                    796

<210> SEQ ID NO 24
<211> LENGTH: 796
<212> TYPE: DNA
<213> ORGANISM: Sphingomonas melonis DC18

<400> SEQUENCE: 24
ccatggccct ttctagaaag gaggaataaa catgaccgtc gatcacgacg cacggatcag     60
cctgctgctg gccgcagcca tcggcgccgc gtggctggcg atccatgtcg ggcgatcgt    120 gtggtggcga tggagcccgg cgacggcggt gctcgcgatc cccgtcgtgc tcgtacaggc    180
gtggctgagc accggcctgt tcatcgtcgc gcacgattgc atgcacggat cgttcgtgcc    240
cggccggccc gcggtcaacc ggaccgtcgg gacgctgtgc ctcggcgcct atgcgggact    300
gtcctatggc cagctccatc ccaagcatca tgcgcatcac gatgcgccgg gcaccgccgc    360
cgaccccgat ttccatgccg gcgcgccgcg atccgcactg ccgtggttcg cgcgtttctt    420
caccagctat tacacgcacg gccagatcct ccggatcacc gcggcggcgg tgctgtacat    480
gctgctcggt gtgtcgctgc tcaacatcgt cgtgttctgg gcgttgccgg cgctgatcgc    540
gctggcgcag ctgttcgtct tcggcaccct cctgccgcat cgccacggcg acacgccgtt    600
cgcggacgcg cacaatgccc gcagcaacgg ctggccacgg ctggcgtcgc tggcgacctg    660
cttccacctc ggcgcctatc atcacgaaca tcacctgagc ccgtggacgc cctggtggca    720
gttgccgcgc gtcggccagc ctgccgccgg acaccggtcg ttaagcaaag accggtagac    780
tagtaagggc gaattc                                                    796

<210> SEQ ID NO 25
<211> LENGTH: 796
<212> TYPE: DNA
<213> ORGANISM: Sphingomonas melonis DC18

<400> SEQUENCE: 25

| | | |
|---|---|---|
| ccatggccct tctagaaag gaggaataaa catgaccgtc gatcacgacg cacggatcag | 60 |
| cctgctgctg gccgcagcca tcggcgccgc gtggctggcg atccatgtcg gggcgatcgt | 120 |
| gtggtggcga tggagcccgg cgacggcggt gctcgcgatc ccgtcgtgc tcgtacaggc | 180 |
| atggctgagc accggcctgt tcatcgtcgc gcacgattgc atgcacggat cgttcgtgcc | 240 |
| cggccggccc gcggtcaacc ggaccgtcgg gacgctgtgc ctcggcgcct atgcgggact | 300 |
| gtcctatggc cagctccatc ccaagcatca tgcgcatcac gatgcgccgg gcaccgccgc | 360 |
| cgaccccgat ttccatgccg gcgcgccgcg atccgcactg ccgtggttcg cgcgcttctt | 420 |
| caccagctat tacacgcacg gccagatcct ccggatcacc gcggcggcgg tgctgtacat | 480 |
| gctgctcggt gtgtcgctgc tcaacatcgt cgtgttctgg gcgttgccgg cgctgatcgc | 540 |
| gctggcgcag ctgttcgtct tcggcacctt cctgccgcat cgccacggcg acacgccgtt | 600 |
| cgcggacgcg cacaatgccc gcagcaacgg ctggccacgg ctggcgtcgc tggcgacctg | 660 |
| cttccacctc ggcgcctatc atcacgaaca tcacctgagc ccgtggacgc cctggtggca | 720 |
| gttgccgcgc gtcggccagc ctgccgccgg acaccggtcg ttaagcaaag accggtagac | 780 |
| tagtaagggc gaattc | 796 |

<210> SEQ ID NO 26
<211> LENGTH: 796
<212> TYPE: DNA
<213> ORGANISM: Sphingomonas melonis DC18

<400> SEQUENCE: 26

| | | |
|---|---|---|
| ccatggccct ttctagaaag gaggaataaa catgaccgtc gatcacgacg cacggatcag | 60 |
| cctgctgctg gccgcagcca tcggcgccgc gtggctggcg atccatgtcg gggcgatcgt | 120 |
| gtggtggcga tggagcccgg cgacggcggt gctcgcgatc ccgtcgtgc tcgtacaggc | 180 |
| gtggctgagc accggcctgt tcatcgtcgc gcacgattgc atgcacggat cgttcgtgcc | 240 |
| cggccggccc gcggtcaacc ggaccgtcgg gacgctgtgc ctcggcgcct atgcgggact | 300 |
| gtcctatggc cagctccatc ccaagcatca tgcgcatcac gatgcgccgg gcaccgccgc | 360 |
| cgaccccgat ttccatgccg gcgcgccgcg atccgcactg ccgtggttcg cgcgcttctt | 420 |
| caccagctat tacacgcacg gccagatcct ccggatcacc gcggcggcgg tactgtacat | 480 |
| gctgctcggt gtgtcgctgc tcaacatcgt cgtgttctgg gcgttgccgg cgctgatcgc | 540 |
| gctggcgcag ctgttcgtct tcggcacctt cctgccgcat cgccacggcg acacgccgtt | 600 |
| cgcggacgcg cacaatgccc gcagcaacgg ctggccacgg ctggcgtcgc tggcgacctg | 660 |
| cttccacctc ggcgcctatc atcacgaaca tcacctgagc ccgtggacgc cctggtggca | 720 |
| gttgccgcgc gtcggccagc ctgccgccgg acaccggtcg ttaagcaaag accggtagac | 780 |
| tagtaagggc gaattc | 796 |

<210> SEQ ID NO 27
<211> LENGTH: 796
<212> TYPE: DNA
<213> ORGANISM: Sphingomonas melonis DC18
<220> FEATURE:
<221> NAME/KEY: CDS

<222> LOCATION: (32)..(778)

<400> SEQUENCE: 27

```
ccatggccct ttctagaaag gaggaataaa c atg acc gtc gat cac gac gca         52
                                   Met Thr Val Asp His Asp Ala
                                     1               5 cgg atc agc ctg ctg ctg gcc gca gcc atc ggc gcc gcg tgg ctg gcg        100
Arg Ile Ser Leu Leu Leu Ala Ala Ala Ile Gly Ala Ala Trp Leu Ala
         10                  15                  20 atc cat gtc ggg gcg atc gtg tgg tgg cga tgg agc ccg gcg acg gcg        148
Ile His Val Gly Ala Ile Val Trp Trp Arg Trp Ser Pro Ala Thr Ala
 25                  30                  35 gtg ctc gcg atc ccc gtc gtg ctc gta cag gcg tgg ctg agc acc ggc        196
Val Leu Ala Ile Pro Val Val Leu Val Gln Ala Trp Leu Ser Thr Gly
40                  45                  50                  55 ctg ttc atc gtc gcg cac gat tgc atg cac gga tcg ttc gtg ccc ggc        244
Leu Phe Ile Val Ala His Asp Cys Met His Gly Ser Phe Val Pro Gly
                 60                  65                  70 cgg ccc gcg gtc aac cgg acc gtt ggg acg ctg tgc ctc ggc gcc tat        292
Arg Pro Ala Val Asn Arg Thr Val Gly Thr Leu Cys Leu Gly Ala Tyr
             75                  80                  85 gcg gga ctg tcc tat ggc cag ctc cat ccc aag cat cat gcg cat cac        340
Ala Gly Leu Ser Tyr Gly Gln Leu His Pro Lys His His Ala His His
         90                  95                 100 gat gcg ccg ggc acc gcc gcc gac ccc gat ttc cat gcc ggc gcg ccg        388
Asp Ala Pro Gly Thr Ala Ala Asp Pro Asp Phe His Ala Gly Ala Pro
105                 110                 115 cga tcc gca ctg ccg tgg ttc gcg cgc ttc ttc acc agc tat tac acg        436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gtg ctg tac atg ctg        484
His Gly Gln Ile Leu Arg Ile Thr Ala Ala Ala Val Leu Tyr Met Leu
                140                 145                 150 ctc ggt gtg tcg ctg ctc aac atc gtc gtg ttc tgg gcg ttg ccg gcg        532
Leu Gly Val Ser Leu Leu Asn Ile Val Val Phe Trp Ala Leu Pro Ala
            155                 160                 165 ctg atc gcg ctg gcg cag ctg ttc gtc ttc ggc acc ttc ctg ccg cat        580
Leu Ile Ala Leu Ala Gln Leu Phe Val Phe Gly Thr Phe Leu Pro His
        170                 175                 180 cgt cac ggc gac acg ccg ttc gcg gac gcg cac aat gcc cgc agc agc        628
Arg His Gly Asp Thr Pro Phe Ala Asp Ala His Asn Ala Arg Ser Ser
    185                 190                 195 ggc tgg cca cgg ctg gcg tcg ctg gcg acc tgc ttc cac ctc ggc gcc        676
Gly Trp Pro Arg Leu Ala Ser Leu Ala Thr Cys Phe His Leu Gly Ala
200                 205                 210                 215 tat cat cac gaa cat cac ctg agc ccg tgg acg ccc tgg tgg cag ttg        724
Tyr His His Glu His His Leu Ser Pro Trp Thr Pro Trp Trp Gln Leu
                220                 225                 230 ccg cgc gtc ggc cag cct gcc gcc gga cac cgg tcg tta agc aaa gac        772
Pro Arg Val Gly Gln Pro Ala Ala Gly His Arg Ser Leu Ser Lys Asp
            235                 240                 245 cgg tag actagtaagg gcgaattc                                            796
Arg
```

<210> SEQ ID NO 28
<211> LENGTH: 248
<212> TYPE: PRT
<213> ORGANISM: Sphingomonas melonis DC18

<400> SEQUENCE: 28

```
Met Thr Val Asp His Asp Ala Arg Ile Ser Leu Leu Ala Ala Ala
1               5                   10                  15

Ile Gly Ala Ala Trp Leu Ala Ile His Val Gly Ala Ile Val Trp Trp
            20                  25                  30

Arg Trp Ser Pro Ala Thr Ala Val Leu Ala Ile Pro Val Val Leu Val
            35                  40                  45

Gln Ala Trp Leu Ser Thr Gly Leu Phe Ile Val Ala His Asp Cys Met
50                  55                  60

His Gly Ser Phe Val Pro Gly Arg Pro Ala Val Asn Arg Thr Val Gly
65                  70                  75                  80

Thr Leu Cys Leu Gly Ala Tyr Ala Gly Leu Ser Tyr Gly Gln Leu His
                85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
            115                 120                 125

Phe Phe Thr Ser Tyr Tyr Thr His Gly Gln Ile Leu Arg Ile Thr Ala
130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Ala His Asn Ala Arg Ser Ser Gly Trp Pro Arg Leu Ala Ser Leu Ala
            195                 200                 205

Thr Cys Phe His Leu Gly Ala Tyr His His Glu His His Leu Ser Pro
210                 215                 220

Trp Thr Pro Trp Trp Gln Leu Pro Arg Val Gly Gln Pro Ala Ala Gly
225                 230                 235                 240

His Arg Ser Leu Ser Lys Asp Arg
                245
```

<210> SEQ ID NO 29
<211> LENGTH: 796
<212> TYPE: DNA
<213> ORGANISM: Sphingomonas melonis DC18
<220> FEATURE:
<221> NAME/KEY: CDS
<222> LOCATION: (32)..(778)

<400> SEQUENCE: 29

```
ccatggccct ttctagaaag gaggaataaa c atg acc gtc gat cac gac gca         52
                                   Met Thr Val Asp His Asp Ala
                                   1               5 cgg atc agc ctg ctg ctg gcc gca gcc atc ggc gcc gcg tgg ctg gcg       100
Arg Ile Ser Leu Leu Leu Ala Ala Ala Ile Gly Ala Ala Trp Leu Ala
            10                  15                  20 atc cat gtc ggg gcg atc gtg tgg tgg cga tgg agc ccg gcg acg gcg       148
Ile His Val Gly Ala Ile Val Trp Trp Arg Trp Ser Pro Ala Thr Ala
25                  30                  35 gtg ctc gcg atc ccc gtc gtg ctc gta cag gcg tgg ctg agc acc ggc       196
Val Leu Ala Ile Pro Val Val Leu Val Gln Ala Trp Leu Ser Thr Gly
40                  45                  50                  55 ctg ttc atc gtc gcg cac gat tgc atg cac gga tcg ttc gtg ccc ggc       244
Leu Phe Ile Val Ala His Asp Cys Met His Gly Ser Phe Val Pro Gly
                60                  65                  70
```

```
cgg ccc gcg gtc aac cgg acc gtc ggg acg ctg tgc ctc ggc gcc tat      292
Arg Pro Ala Val Asn Arg Thr Val Gly Thr Leu Cys Leu Gly Ala Tyr
         75                  80                  85 gcg gga ctg tcc tat ggc cag ctc cat ccc aag cat cat gcg cat cac      340
Ala Gly Leu Ser Tyr Gly Gln Leu His Pro Lys His His Ala His His
     90                  95                 100 gat gcg ccg ggc acc gcc gcc gac ccc gat ttc cat gcc ggc gcg ccg      388
Asp Ala Pro Gly Thr Ala Ala Asp Pro Asp Phe His Ala Gly Ala Pro
105                 110                 115 cga tcc gca ctg ccg tgg ttc gcg cgc ttc ttc acc agc tat tac acg      436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gtg ctg tac atg ctg      484
His Gly Gln Ile Leu Arg Ile Thr Ala Ala Ala Val Leu Tyr Met Leu
             140                 145                 150 ctc ggt gtg tcg ctg ctc aac atc gtc gtg ttc tgg gcg ttg ccg gcg      532
Leu Gly Val Ser Leu Leu Asn Ile Val Val Phe Trp Ala Leu Pro Ala
             155                 160                 165 ctg atc gcg ctg gcg cag ctg ttc gtc ttc ggc acc ttc ctg ccg cat      580
Leu Ile Ala Leu Ala Gln Leu Phe Val Phe Gly Thr Phe Leu Pro His
         170                 175                 180 cgc cac ggc gac acg ccg ttc gcg gac gcg cac aat gcc cgc agc aac      628
Arg His Gly Asp Thr Pro Phe Ala Asp Ala His Asn Ala Arg Ser Asn
     185                 190                 195 ggc tgg cca tgg ctg gcg tcg ctg gcg acc tgc ttc cac ttc ggc gcc      676
Gly Trp Pro Trp Leu Ala Ser Leu Ala Thr Cys Phe His Phe Gly Ala
200                 205                 210                 215 tat cat cac gaa cat cac ctg agc ccg tgg acg ccc tgg tgg cag ttg      724
Tyr His His Glu His His Leu Ser Pro Trp Thr Pro Trp Trp Gln Leu
                220                 225                 230 ccg cgc gtc ggc cag cct gcc gcc gga cac cgg tcg tta agc aaa gac      772
Pro Arg Val Gly Gln Pro Ala Ala Gly His Arg Ser Leu Ser Lys Asp
            235                 240                 245 cgg tag actagtaagg gcgaattc                                         796
Arg
```

```
<210> SEQ ID NO 30
<211> LENGTH: 248
<212> TYPE: PRT
<213> ORGANISM: Sphingomonas melonis DC18

<400> SEQUENCE: 30

Met Thr Val Asp His Asp Ala Arg Ile Ser Leu Leu Ala Ala Ala
1               5                   10                  15

Ile Gly Ala Ala Trp Leu Ala Ile His Val Gly Ala Ile Val Trp Trp
            20                  25                  30

Arg Trp Ser Pro Ala Thr Ala Val Leu Ala Ile Pro Val Val Leu Val
        35                  40                  45

Gln Ala Trp Leu Ser Thr Gly Leu Phe Ile Val Ala His Asp Cys Met
    50                  55                  60

His Gly Ser Phe Val Pro Gly Arg Pro Ala Val Asn Arg Thr Val Gly
65                  70                  75                  80

Thr Leu Cys Leu Gly Ala Tyr Ala Gly Leu Ser Tyr Gly Gln Leu His
                85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125
```

```
Phe Phe Thr Ser Tyr Tyr Thr His Gly Gln Ile Leu Arg Ile Thr Ala
    130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Ala His Asn Ala Arg Ser Asn Gly Trp Pro Trp Leu Ala Ser Leu Ala
        195                 200                 205

Thr Cys Phe His Phe Gly Ala Tyr His His Glu His His Leu Ser Pro
    210                 215                 220

Trp Thr Pro Trp Trp Gln Leu Pro Arg Val Gly Gln Pro Ala Ala Gly
225                 230                 235                 240

His Arg Ser Leu Ser Lys Asp Arg
                245
```

<210> SEQ ID NO 31
<211> LENGTH: 796
<212> TYPE: DNA
<213> ORGANISM: Sphingomonas melonis DC18

<400> SEQUENCE: 31

```
ccatggccct ttctagaaag gaggaataaa catgaccgtc gatcacgacg cacggatcag    60
cctgctgctg gccgcagcca tcggcgccgc gtggctggcg atccatgtcg gggcgatcgt   120
gtggtggcga tggagcccgg cgacggcggt gctcgcgatc ccgtcgtgc tcgtacaggc   180
gtggctgagc accggcctgt tcatcgtcgc gacgattgc atgcacggat cgttcgtgcc   240
cggccggccc gcggtcaacc ggaccgtcgg gacgctgtgc ctcggcgcct atgcgggact   300
gtcctatggc cagctccatc ccaagcatca tgcgcatcac gatgcgccgg gcaccgccgc   360
cgaccccgat ttccatgccg gcgcgccgcg atccgcactg ccgtggttcg cgcgcttctt   420
caccagctat tacacgcacg gccagatcct ccggatcacc gcggcggcgg tgctgtacat   480
gctgctcggt gtgtcgctgc tcaacatcgt cgtgttctgg gcgctgccgg cgctgatcgc   540
gctggcgcag ctgttcgtct tcggcacctt cctgccgcat cgccacgcg acacgccgtt   600
cgcggacgcg cacaatgccc gcagcaacgg ctggccatgg ctggcgtcgc tggcgacctg   660
cttccactc ggcgcctatc atcacgaaca tcacctgagc ccgtggacgc cctggtggca   720
gttgccgcgc gtcggccagc ctgccgccgg acaccggtcg ttaagcaaag accggtagac   780
tagtaagggc gaattc                                                   796
```

<210> SEQ ID NO 32
<211> LENGTH: 796
<212> TYPE: DNA
<213> ORGANISM: Sphingomonas melonis DC18

<400> SEQUENCE: 32

```
ccatggccct ttctagaaag gaggaataaa catgaccgtc gatcacgacg cacggatcag    60
cctgctgctg gccgcagcca tcggcgccgc gtggctggcg atccatgtcg gggcgatcgt   120
gtggtggcga tggagcccgg cgacggcggt gctcgcgatc ccgtcgtgc tcgtacaggc   180
gtggctgagc accggcctgt tcatcgtcgc gacgattgc atgcacggat cgttcgtgcc   240
tggccggccc gcggtcaacc ggaccgtcgg gacgctgtgc ctcggcgcct atgcgggact   300
gtcctatggc cagctccatc ccaagcatca tgcgcatcac gatgcgccgg gcaccgccgc   360
```

```
cgacccegat tccatgccg gcgcgccgcg atccgcactg ccgtggttcg cgcgcttctt    420
caccagctat tacacgcacg gccagatcct ccggatcacc gcggcggcgg tgctgtacat    480
gctgctcggt gtgtcgctgc tcaacatcgt cgtgttctgg gcgttgccgg cgctgatcgc    540
gctggcgcag ctgttcgtct tcggcacctt cctgccgcat cgccacggcg acacgccgtt    600
cgcggacgcg cacaatgccc gcagcaacgg ctggccatgg ctggcgtcgc tggcgacctg    660
cttccacttc ggcgcctatc atcacgaaca tcacctgagc ccgtggacgc cctggtggca    720
gttgccgcgc gtcggccagc ctgccgccgg acaccggtcg ttaagcaaag accggtagac    780
tagtaagggc gaattc                                                    796

<210> SEQ ID NO 33
<211> LENGTH: 796
<212> TYPE: DNA
<213> ORGANISM: Sphingomonas melonis DC18

<400> SEQUENCE: 33
ccatggccct ttctagaaag gaggaataaa catgaccgtc gatcacgacg cacggatcag     60
cctgctgctg gccgcagcca tcggcgccgc gtggctggcg atccatgtcg gggcgatcgt    120
gtggtggcga tggagcccgg cgacggcggt gctcgcgatc cccgtcgtgc tcgtacaggc    180
gtggctgagc accggcctgt tcatcgtcgc gcacgattgc atgcacggat cgttcgtgcc    240
cggccggccc gcggtcaacc ggaccgtcgg gacgctgtgc ctcggcgcct atgcgggact    300
gtcctatggc cagctccatc ccaagcatca tgcgcatcac gatgcgccgg gcactgccgc    360 cgacccegat tccatgccg gcgcgccgcg atccgcactg ccgtggttcg cgcgcttctt    420
caccagctat tacacgcacg gccagatcct ccggatcacc gcggcggcgg tgctgtacat    480
gctgctcggt gtgtcgctgc tcaacatcgt cgtgttctgg gcgttgccgg cgctgatcgc    540
gctggcgcag ctgttcgtct tcggcacctt cctgccgcat cgccacggcg acacgccgtt    600
cgcggacgcg cacaatgccc gcagcaacgg ctggccatgg ctggcgtcgc tggcgacctg    660
cttccacttc ggcgcctatc atcacgaaca tcacctgagc ccgtggacgc cctggtggca    720
gttgccgcgc gtcggccagc ctgccgccgg acaccggtcg ttaagcaaag accggtagac    780
tagtaagggc gaattc                                                    796

<210> SEQ ID NO 34
<211> LENGTH: 796
<212> TYPE: DNA
<213> ORGANISM: Sphingomonas melonis DC18

<400> SEQUENCE: 34
ccatggccct ttctagaaag gaggaataaa catgaccgtc gatcacgacg cacggatcag     60
cctgctgctg gccgcagcca tcggcgccgc gtggctggcg atccatgtcg ggcaatcgt    120 gtggtggcga tggagcccgg cgacggcggt gctcgcgatc cccgtcgtgc tcgtacaggc    180
gtggctgagc accggcctgt tcatcgtcgc gcacgattgc atgcacggat cgttcgtgcc    240
cggccggccc gcggtcaacc ggaccgtcgg gacgctgtgc ctcggcgcct atgcgggact    300
gtcctatggc cagctccatc ccaagcatca tgcgcatcac gatgcgccgg gcaccgccgc    360 cgacccegat tccatgccg gcgcgccgcg atccgcactg ccgtggttcg cgcgcttctt    420
caccagctat tacacgcacg gccagatcct ccggatcacc gcggcggcgg tgctgtacat    480
gctgctcggt gtgtcgctgc tcaacatcgt cgtgttctgg gcgttgccgg cgctgatcgc    540
```

```
gctggcgcag ctgttcgtct tcggcacctt cctgccgcat cgccacggcg acacgccgtt    600
cgcggacgcg cacaatgccc gcagcaacgg ctggccatgg ctggcgtcgc tggcgacctg    660
cttccacttc ggcgcctatc atcacgaaca tcacctgagc ccgtggacgc cctggtggca    720
gttgccgcgc gtcggccagc ctgccgccgg acaccggtcg ttaagcaaag accggtagac    780
tagtaagggc gaattc                                                    796
```

```
<210> SEQ ID NO 35
<211> LENGTH: 796
<212> TYPE: DNA
<213> ORGANISM: Sphingomonas melonis DC18
<220> FEATURE:
<221> NAME/KEY: CDS
<222> LOCATION: (32)..(778)

<400> SEQUENCE: 35
ccatggccct ttctagaaag gaggaataaa c atg acc gtc gat cac gac gca         52
                                   Met Thr Val Asp His Asp Ala
                                    1               5 cgg atc agc ctg ctg ctg gcc gca gcc atc ggc gcc gcg tgg ctg gcg      100
Arg Ile Ser Leu Leu Leu Ala Ala Ala Ile Gly Ala Ala Trp Leu Ala
         10                  15                  20 atc cat gtc ggg gcg atc gtg tgg tgg caa tgg agc ccg gcg acg gcg      148
Ile His Val Gly Ala Ile Val Trp Trp Gln Trp Ser Pro Ala Thr Ala
 25                  30                  35 gtg ctc gcg atc ccc gtc gtg ctc gta cag gcg tgg ctg agc acc ggc      196
Val Leu Ala Ile Pro Val Val Leu Val Gln Ala Trp Leu Ser Thr Gly
40                  45                  50                  55 ctg ttc atc gtc gcg cac gat tgc atg cac gga tcg ttc gtg ccc ggc      244
Leu Phe Ile Val Ala His Asp Cys Met His Gly Ser Phe Val Pro Gly
                 60                  65                  70 cgg ccc gcg gtc aac cgg acc gtc ggg acg ctg tgc ctc ggc gcc tat      292
Arg Pro Ala Val Asn Arg Thr Val Gly Thr Leu Cys Leu Gly Ala Tyr
             75                  80                  85 gcg gga ctg tcc tat ggc cag ctc cat ccc aag cat cat gcg cat cac      340
Ala Gly Leu Ser Tyr Gly Gln Leu His Pro Lys His His Ala His His
         90                  95                 100 gat gcg ccg ggc acc gcc gcc gac ccc gat ttc cat gcc ggc gcg ccg      388
Asp Ala Pro Gly Thr Ala Ala Asp Pro Asp Phe His Ala Gly Ala Pro
    105                 110                 115 cga tcc gca ctg ccg tgg ttc gcg cgc ttc ttc acc agc tat tac acg      436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gtg ctg tac atg ctg      484
His Gly Gln Ile Leu Arg Ile Thr Ala Ala Ala Val Leu Tyr Met Leu
                140                 145                 150 ctc ggt gtg tcg ctg ctc aac atc gtc gtg ttc tgg gcg ttg ccg gcg      532
Leu Gly Val Ser Leu Leu Asn Ile Val Val Phe Trp Ala Leu Pro Ala
            155                 160                 165 ctg atc gcg ctg gcg cag ctg ttc gtc ttc ggc acc ttc ctg ccg cat      580
Leu Ile Ala Leu Ala Gln Leu Phe Val Phe Gly Thr Phe Leu Pro His
        170                 175                 180 cgc cac ggc gac acg ccg ttc gcg gac gcg cac aat gcc cgc agt aac      628
Arg His Gly Asp Thr Pro Phe Ala Asp Ala His Asn Ala Arg Ser Asn
    185                 190                 195 ggc tgg cca tgg ctg gcg tcg ctg gcg acc tgc ttc cac ttc ggc gcc      676
Gly Trp Pro Trp Leu Ala Ser Leu Ala Thr Cys Phe His Phe Gly Ala
200                 205                 210                 215 tat cat cac gaa cat cac ctg agc ccg tgg acg ccc tgg tgg cag ttg      724
Tyr His His Glu His His Leu Ser Pro Trp Thr Pro Trp Trp Gln Leu
```

```
                    220                 225                 230
ccg cgc gtc ggc cag cct gcc gcc gga cac cgg tcg tta agc aaa gac       772
Pro Arg Val Gly Gln Pro Ala Ala Gly His Arg Ser Leu Ser Lys Asp
            235                 240                 245 cgg tag actagtaagg gcgaattc                                            796
Arg

<210> SEQ ID NO 36
<211> LENGTH: 248
<212> TYPE: PRT
<213> ORGANISM: Sphingomonas melonis DC18

<400> SEQUENCE: 36

Met Thr Val Asp His Asp Ala Arg Ile Ser Leu Leu Ala Ala Ala
1               5                   10                  15

Ile Gly Ala Ala Trp Leu Ala Ile His Val Gly Ala Ile Val Trp Trp
                20                  25                  30

Gln Trp Ser Pro Ala Thr Ala Val Leu Ala Ile Pro Val Leu Val
            35                  40                  45

Gln Ala Trp Leu Ser Thr Gly Leu Phe Ile Val Ala His Asp Cys Met
    50                  55                  60

His Gly Ser Phe Val Pro Gly Arg Pro Ala Val Asn Arg Thr Val Gly
65                  70                  75                  80

Thr Leu Cys Leu Gly Ala Tyr Ala Gly Leu Ser Tyr Gly Gln Leu His
                85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125

Phe Phe Thr Ser Tyr Tyr Thr His Gly Gln Ile Leu Arg Ile Thr Ala
    130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Ala His Asn Ala Arg Ser Asn Gly Trp Pro Trp Leu Ala Ser Leu Ala
        195                 200                 205

Thr Cys Phe His Phe Gly Ala Tyr His His Glu His His Leu Ser Pro
    210                 215                 220

Trp Thr Pro Trp Trp Gln Leu Pro Arg Val Gly Gln Pro Ala Ala Gly
225                 230                 235                 240

His Arg Ser Leu Ser Lys Asp Arg
                245

<210> SEQ ID NO 37
<211> LENGTH: 796
<212> TYPE: DNA
<213> ORGANISM: Sphingomonas melonis DC18
<220> FEATURE:
<221> NAME/KEY: CDS
<222> LOCATION: (32)..(778)

<400> SEQUENCE: 37
ccatggccct ttccagaaag gaggaataaa c atg acc gtc gat cac gac gca       52
                                   Met Thr Val Asp His Asp Ala
                                   1               5
```

```
cgg atc agc ctg ctg ctg gcc gca gcc atc ggc gcc gcg tgg ctg gcg       100
Arg Ile Ser Leu Leu Leu Ala Ala Ala Ile Gly Ala Ala Trp Leu Ala
         10                  15                  20 atc cat gtc ggg gcg atc gtg tgg tgg cga tgg agc ccg gcg acg gcg       148
Ile His Val Gly Ala Ile Val Trp Trp Arg Trp Ser Pro Ala Thr Ala
 25                  30                  35 gtg ctc gcg atc ccc gtc gtg ctc gta cag gcg tgg ctg agc acc ggc       196
Val Leu Ala Ile Pro Val Val Leu Val Gln Ala Trp Leu Ser Thr Gly
 40                  45                  50                  55 ctg ttc atc gtc gcg cac gat tgc atg cac gga tcg ttc gtg ccc ggc       244
Leu Phe Ile Val Ala His Asp Cys Met His Gly Ser Phe Val Pro Gly
                 60                  65                  70 cgg ccc gcg gtc aac cgg acc gtc ggg acg ctg tgc ctc ggc gcc tat       292
Arg Pro Ala Val Asn Arg Thr Val Gly Thr Leu Cys Leu Gly Ala Tyr
         75                  80                  85 gcg gga ctg tcc tat ggc cag ctc cat ccc aag cat cat gcg cat cac       340
Ala Gly Leu Ser Tyr Gly Gln Leu His Pro Lys His His Ala His His
                 90                  95                 100 gat gcg ccg ggc acc gcc gcc gac ccc gat ttc cat gcc ggc gcg ccg       388
Asp Ala Pro Gly Thr Ala Ala Asp Pro Asp Phe His Ala Gly Ala Pro
105                 110                 115 cga tcc gca ctg ccg tgg ttc gcg cgc ttc ttc acc agc tat tac acg       436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gtg ctg tac atg ctg       484
His Gly Gln Ile Leu Arg Ile Thr Ala Ala Ala Val Leu Tyr Met Leu
                140                 145                 150 ctc ggt gtg tcg ctg ctc aac atc gtc gtg ttc tgg gcg gtg ccg gcg       532
Leu Gly Val Ser Leu Leu Asn Ile Val Val Phe Trp Ala Val Pro Ala
        155                 160                 165 ctg atc gcg ctg gcg cag ctg ttc gtc ttc ggc acc ttc ctg ccg cat       580
Leu Ile Ala Leu Ala Gln Leu Phe Val Phe Gly Thr Phe Leu Pro His
        170                 175                 180 cgc cac ggc gac acg ccg ttc gcg gac gcg cac aat gcc cgc agc aac       628
Arg His Gly Asp Thr Pro Phe Ala Asp Ala His Asn Ala Arg Ser Asn
185                 190                 195 ggc tgg cca tgg ctg gcg tcg ctg gcg acc tgc ttc cac ttc ggc gcc       676
Gly Trp Pro Trp Leu Ala Ser Leu Ala Thr Cys Phe His Phe Gly Ala
200                 205                 210                 215 tat cat cac gaa cat cac ctg agc ccg tgg acg ccc tgg tgg cag ttg       724
Tyr His His Glu His His Leu Ser Pro Trp Thr Pro Trp Trp Gln Leu
                220                 225                 230 ccg cgc gtc ggc cag cct gcc gcc gga cac cgg tcg tta agc aaa gac       772
Pro Arg Val Gly Gln Pro Ala Ala Gly His Arg Ser Leu Ser Lys Asp
        235                 240                 245 cgg tag actagtaagg gcgaattc                                           796
Arg

<210> SEQ ID NO 38
<211> LENGTH: 248
<212> TYPE: PRT
<213> ORGANISM: Sphingomonas melonis DC18

<400> SEQUENCE: 38

Met Thr Val Asp His Asp Ala Arg Ile Ser Leu Leu Ala Ala Ala
 1               5                  10                  15

Ile Gly Ala Ala Trp Leu Ala Ile His Val Gly Ala Ile Val Trp Trp
            20                  25                  30

Arg Trp Ser Pro Ala Thr Ala Val Leu Ala Ile Pro Val Val Leu Val
```

-continued

```
                 35                  40                  45
Gln Ala Trp Leu Ser Thr Gly Leu Phe Ile Val Ala His Asp Cys Met
 50                  55                  60

His Gly Ser Phe Val Pro Gly Arg Pro Ala Val Asn Arg Thr Val Gly
 65                  70                  75                  80

Thr Leu Cys Leu Gly Ala Tyr Ala Gly Leu Ser Tyr Gly Gln Leu His
                 85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125

Phe Phe Thr Ser Tyr Tyr Thr His Gly Gln Ile Leu Arg Ile Thr Ala
    130                 135                 140

Ala Ala Val Leu Tyr Met Leu Leu Gly Val Ser Leu Leu Asn Ile Val
145                 150                 155                 160

Val Phe Trp Ala Val Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Ala His Asn Ala Arg Ser Asn Gly Trp Pro Trp Leu Ala Ser Leu Ala
        195                 200                 205

Thr Cys Phe His Phe Gly Ala Tyr His His Glu His His Leu Ser Pro
    210                 215                 220

Trp Thr Pro Trp Trp Gln Leu Pro Arg Val Gly Gln Pro Ala Ala Gly
225                 230                 235                 240

His Arg Ser Leu Ser Lys Asp Arg
                245
```

<210> SEQ ID NO 39
<211> LENGTH: 796
<212> TYPE: DNA
<213> ORGANISM: Sphingomonas melonis DC18
<220> FEATURE:
<221> NAME/KEY: CDS
<222> LOCATION: (32)..(778)

<400> SEQUENCE: 39

```
ccatggccct ttctagaaag gaggagtaaa c atg acc gtc gat cac gac gca        52
                                  Met Thr Val Asp His Asp Ala
                                    1               5 cgg atc agc ctg ctg ctg gcc gca gcc atc ggc gcc gcg tgg ctg gcg      100
Arg Ile Ser Leu Leu Leu Ala Ala Ala Ile Gly Ala Ala Trp Leu Ala
         10                  15                  20 atc cat gtc ggg gcg atc gtg tgg tgg cga tgg agc ccg gcg acg gcg      148
Ile His Val Gly Ala Ile Val Trp Trp Arg Trp Ser Pro Ala Thr Ala
 25                  30                  35 gtg ctc gcg atc ccc gtc gtg ctc gta cag gcg tgg ctg agc acc ggc      196
Val Leu Ala Ile Pro Val Val Leu Val Gln Ala Trp Leu Ser Thr Gly
 40                  45                  50                  55 ctg ttc atc gtc gcg cac gat tgc atg cac gga tcg ttc gtg ccc ggc      244
Leu Phe Ile Val Ala His Asp Cys Met His Gly Ser Phe Val Pro Gly
                 60                  65                  70 cgg ccc gcg gtc aac cgg acc gtc ggg acg ctg tgc ctc ggc gcc tat      292
Arg Pro Ala Val Asn Arg Thr Val Gly Thr Leu Cys Leu Gly Ala Tyr
         75                  80                  85 gcg gga ctg tcc tat ggc cag ctc cat ccc aag cat cat gcg cat cac      340
Ala Gly Leu Ser Tyr Gly Gln Leu His Pro Lys His His Ala His His
     90                  95                 100
```

```
gat gcg ccg ggc acc gcc gcc gac ccc gat ttc cat gcc ggc gcg ccg       388
Asp Ala Pro Gly Thr Ala Ala Asp Pro Asp Phe His Ala Gly Ala Pro
105                 110                 115 cga tcc gca ctg ccg tgg ttc gcg cgc ttc ttc acc agc tat tac acg       436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gtg ctg tac atg ctg       484
His Gly Gln Ile Leu Arg Ile Thr Ala Ala Ala Val Leu Tyr Met Leu
                140                 145                 150 ctc ggt gtg tcg ctg ctc aac atc gtc gtg ttc tgg gcg ttg ccg gcg       532
Leu Gly Val Ser Leu Leu Asn Ile Val Val Phe Trp Ala Leu Pro Ala
            155                 160                 165 ctg atc gcg ctg gcg cag ctg ttc gtc ttc ggc acc ttc ctg ccg cat       580
Leu Ile Ala Leu Ala Gln Leu Phe Val Phe Gly Thr Phe Leu Pro His
        170                 175                 180 cgc cac ggc gac acg ccg ttc gcg gac gcg cac aat gcc cgc agc aac       628
Arg His Gly Asp Thr Pro Phe Ala Asp Ala His Asn Ala Arg Ser Asn
185                 190                 195 ggc tgg cca tgg ctg gcg tcg ctg gcg acc tgc ttc cac ttc ggc gcc       676
Gly Trp Pro Trp Leu Ala Ser Leu Ala Thr Cys Phe His Phe Gly Ala
200                 205                 210                 215 tat cat cac gaa cat cac ctg agc ccg tgg acg ccc tgg tgg cag ttg       724
Tyr His His Glu His His Leu Ser Pro Trp Thr Pro Trp Trp Gln Leu
                220                 225                 230 ccg cgc gtc ggc cag cct gcc gcc gga cac cgg tcg tta agc aga gac       772
Pro Arg Val Gly Gln Pro Ala Ala Gly His Arg Ser Leu Ser Arg Asp
            235                 240                 245 cgg tag actagtaagg gcgaattc                                           796
Arg

<210> SEQ ID NO 40
<211> LENGTH: 248
<212> TYPE: PRT
<213> ORGANISM: Sphingomonas melonis DC18

<400> SEQUENCE: 40

Met Thr Val Asp His Asp Ala Arg Ile Ser Leu Leu Ala Ala Ala
1               5                   10                  15

Ile Gly Ala Ala Trp Leu Ala Ile His Val Gly Ala Ile Val Trp Trp
                20                  25                  30

Arg Trp Ser Pro Ala Thr Ala Val Leu Ala Ile Pro Val Val Leu Val
            35                  40                  45

Gln Ala Trp Leu Ser Thr Gly Leu Phe Ile Val Ala His Asp Cys Met
        50                  55                  60

His Gly Ser Phe Val Pro Gly Arg Pro Ala Val Asn Arg Thr Val Gly
65                  70                  75                  80

Thr Leu Cys Leu Gly Ala Tyr Ala Gly Leu Ser Tyr Gly Gln Leu His
                85                  90                  95

Pro Lys His His Ala His His Asp Ala Pro Gly Thr Ala Ala Asp Pro
                100                 105                 110

Asp Phe His Ala Gly Ala Pro Arg Ser Ala Leu Pro Trp Phe Ala Arg
            115                 120                 125

Phe Phe Thr Ser Tyr Tyr Thr His Gly Gln Ile Leu Arg Ile Thr Ala
        130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
```

-continued

```
                        165                 170                 175
Phe Gly Thr Phe Leu Pro His Arg His Gly Asp Thr Pro Phe Ala Asp
            180                 185                 190

Ala His Asn Ala Arg Ser Asn Gly Trp Pro Trp Leu Ala Ser Leu Ala
            195                 200                 205

Thr Cys Phe His Phe Gly Ala Tyr His His Glu His His Leu Ser Pro
            210                 215                 220

Trp Thr Pro Trp Trp Gln Leu Pro Arg Val Gly Gln Pro Ala Ala Gly
225                 230                 235                 240

His Arg Ser Leu Ser Arg Asp Arg
                245

<210> SEQ ID NO 41
<211> LENGTH: 796
<212> TYPE: DNA
<213> ORGANISM: Sphingomonas melonis DC18
<220> FEATURE:
<221> NAME/KEY: CDS
<222> LOCATION: (32)..(778)

<400> SEQUENCE: 41
ccatggccct ttctagaaag gaggaataaa c atg acc gtc gat cac gac gca          52
                                   Met Thr Val Asp His Asp Ala
                                    1               5 cgg atc agc ctg ctg ctg gcc gca gcc atc ggc gcc gcg tgg ctg gcg        100
Arg Ile Ser Leu Leu Leu Ala Ala Ala Ile Gly Ala Ala Trp Leu Ala
        10                  15                  20 atc cat gtc ggg gcg atc gtg tgg tgg cga tgg agc ccg gcg acg gcg        148
Ile His Val Gly Ala Ile Val Trp Trp Arg Trp Ser Pro Ala Thr Ala
    25                  30                  35 gtg ctc gcg atc ccc gtc gtg ctc gta cag gcg tgg ctg agc acc ggc        196
Val Leu Ala Ile Pro Val Val Leu Val Gln Ala Trp Leu Ser Thr Gly
40                  45                  50                  55 ctg ttc atc gtc gcg cac gat tgc atg cac gga tcg ttc gtg ccc ggc        244
Leu Phe Ile Val Ala His Asp Cys Met His Gly Ser Phe Val Pro Gly
                60                  65                  70 cgg ccc gcg gtc aac cgg acc gtc ggg acg ctg tgc ctc ggc gcc tat        292
Arg Pro Ala Val Asn Arg Thr Val Gly Thr Leu Cys Leu Gly Ala Tyr
            75                  80                  85 gcg gga ctg tcc tat ggc cag ctc cat ccc aag cat cat gcg cat cac        340
Ala Gly Leu Ser Tyr Gly Gln Leu His Pro Lys His His Ala His His
        90                  95                 100 gat gcg ccg ggc acc gcc gcc gac ccc gat ttc cat gcc ggc gcg ccg        388
Asp Ala Pro Gly Thr Ala Ala Asp Pro Asp Phe His Ala Gly Ala Pro
    105                 110                 115 cga tcc gca ctg ccg tgg ttc gcg cgc ttc ttc acc agc tat tac acg        436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gtg ctg tac atg ctg        484
His Gly Gln Ile Leu Arg Ile Thr Ala Ala Ala Val Leu Tyr Met Leu
                140                 145                 150 ctc ggt gtg tcg ctg ctc aac atc gtc gtg ttc tgg gcg ttg ccg gcg        532
Leu Gly Val Ser Leu Leu Asn Ile Val Val Phe Trp Ala Leu Pro Ala
            155                 160                 165 ctg atc gcg ctg gcg cag ctg ttc gtc ttc ggc acc ttc ctg ccg cat        580
Leu Ile Ala Leu Ala Gln Leu Phe Val Phe Gly Thr Phe Leu Pro His
        170                 175                 180 cgc cac ggc gac acg ccg ttc gcg gac acg cac aac gcc cgc agc aac        628
Arg His Gly Asp Thr Pro Phe Ala Asp Thr His Asn Ala Arg Ser Asn
    185                 190                 195
```

```
ggc tgg cca tgg ctg gcg tcg ctg gcg acc tgc ttc cac ttc ggc gcc        676
Gly Trp Pro Trp Leu Ala Ser Leu Ala Thr Cys Phe His Phe Gly Ala
200                 205                 210                 215 tat cat cac gaa cat cac ctg agc ccg tgg acg ccc tgg tgg cag ttg        724
Tyr His His Glu His His Leu Ser Pro Trp Thr Pro Trp Trp Gln Leu
                220                 225                 230 ccg cgc gtc ggc cag cct gcc gcc gga cac cgg tcg tta agc aaa gac        772
Pro Arg Val Gly Gln Pro Ala Ala Gly His Arg Ser Leu Ser Lys Asp
                235                 240                 245 cgg tag actagtaagg gcgaattc                                            796
Arg
```

<210> SEQ ID NO 42
<211> LENGTH: 248
<212> TYPE: PRT
<213> ORGANISM: Sphingomonas melonis DC18

<400> SEQUENCE: 42

```
Met Thr Val Asp His Asp Ala Arg Ile Ser Leu Leu Ala Ala Ala
1               5                   10                  15

Ile Gly Ala Ala Trp Leu Ala Ile His Val Gly Ala Ile Val Trp Trp
                20                  25                  30

Arg Trp Ser Pro Ala Thr Ala Val Leu Ala Ile Pro Val Val Leu Val
            35                  40                  45

Gln Ala Trp Leu Ser Thr Gly Leu Phe Ile Val Ala His Asp Cys Met
        50                  55                  60

His Gly Ser Phe Val Pro Gly Arg Pro Ala Val Asn Arg Thr Val Gly
65                  70                  75                  80

Thr Leu Cys Leu Gly Ala Tyr Ala Gly Leu Ser Tyr Gly Gln Leu His
                85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125

Phe Phe Thr Ser Tyr Tyr Thr His Gly Gln Ile Leu Arg Ile Thr Ala
    130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Thr His Asn Ala Arg Ser Asn Gly Trp Pro Trp Leu Ala Ser Leu Ala
        195                 200                 205

Thr Cys Phe His Phe Gly Ala Tyr His His Glu His His Leu Ser Pro
    210                 215                 220

Trp Thr Pro Trp Trp Gln Leu Pro Arg Val Gly Gln Pro Ala Ala Gly
225                 230                 235                 240

His Arg Ser Leu Ser Lys Asp Arg
                245
```

<210> SEQ ID NO 43
<211> LENGTH: 796
<212> TYPE: DNA
<213> ORGANISM: Sphingomonas melonis DC18
<220> FEATURE:
<221> NAME/KEY: CDS

<222> LOCATION: (32)..(778)

<400> SEQUENCE: 43

```
ccatggccct ttctagaaag gaggaataaa c atg acc gtc gat cac gac gca       52
                                   Met Thr Val Asp His Asp Ala
                                    1               5 cgg atc agc ctg ctg ctg gcc gca gcc atc ggc gcc gcg tgg ctg gcg      100
Arg Ile Ser Leu Leu Leu Ala Ala Ala Ile Gly Ala Ala Trp Leu Ala
         10                  15                  20 atc cat gtc ggg gcg atc gtg tgg tgg cga tgg agc ccg gcg acg gcg     148
Ile His Val Gly Ala Ile Val Trp Trp Arg Trp Ser Pro Ala Thr Ala
 25                  30                  35 gtg ctc gcg atc ccc gtc gtg cta gta cag gcg tgg ctg agc acc ggc     196
Val Leu Ala Ile Pro Val Val Leu Val Gln Ala Trp Leu Ser Thr Gly
 40                  45                  50                  55 ctg ttc atc gtc gcg cac gat tgc atg cac gga tcg ttc gtg ccc ggc     244
Leu Phe Ile Val Ala His Asp Cys Met His Gly Ser Phe Val Pro Gly
                 60                  65                  70 cgg ccc gcg gtc aac cgg acc gtc ggg acg ctg tgc ctc ggc gcc tat     292
Arg Pro Ala Val Asn Arg Thr Val Gly Thr Leu Cys Leu Gly Ala Tyr
             75                  80                  85 gcg gga ctg tcc tat ggc cag ctc cat ccc aag cat cat gcg cat cac     340
Ala Gly Leu Ser Tyr Gly Gln Leu His Pro Lys His His Ala His His
         90                  95                 100 gat gcg ccg ggc acc gcc gcc gac ccc gat ttc cat gcc ggc gcg ccg     388
Asp Ala Pro Gly Thr Ala Ala Asp Pro Asp Phe His Ala Gly Ala Pro
105                 110                 115 cga tcc gca ctg ccg tgg ttc gcg cgc ttc ttc acc agc tat tac acg     436
Arg Ser Ala Leu Pro Trp Phe Ala Arg Phe Phe Thr Ser Tyr Tyr Thr
120                 125                 130                 135 cac ggc cag atc ctc cgg atc acc gtt gcg gcg gtg ctg tac atg ctg     484
His Gly Gln Ile Leu Arg Ile Thr Val Ala Ala Val Leu Tyr Met Leu
                140                 145                 150 ctc ggt gtg tcg ctg ctc aac atc gtc gtg ttc tgg gcg ttg ccg gcg     532
Leu Gly Val Ser Leu Leu Asn Ile Val Val Phe Trp Ala Leu Pro Ala
            155                 160                 165 ctg atc gcg ctg gcg cag ctg ttc gtc ttc ggc acc ttc ctg ccg cat     580
Leu Ile Ala Leu Ala Gln Leu Phe Val Phe Gly Thr Phe Leu Pro His
        170                 175                 180 cgc cac ggc gac acg ccg ttc gcg gac gcg cac aat gcc cgc agc aac     628
Arg His Gly Asp Thr Pro Phe Ala Asp Ala His Asn Ala Arg Ser Asn
    185                 190                 195 ggc tgg cca tgg ctg gcg tcg ctg gcg acc tgc ttc cac ttc ggc gcc     676
Gly Trp Pro Trp Leu Ala Ser Leu Ala Thr Cys Phe His Phe Gly Ala
200                 205                 210                 215 tat cat cac gaa cat cac ctg agc ccg tgg acg ccc tgg tgg cag ttg     724
Tyr His His Glu His His Leu Ser Pro Trp Thr Pro Trp Trp Gln Leu
                220                 225                 230 ccg cgc gtc ggc cag cct gcc gcc gga cac cgg tcg tta agc aaa gac     772
Pro Arg Val Gly Gln Pro Ala Ala Gly His Arg Ser Leu Ser Lys Asp
            235                 240                 245 cgg tag actagtaagg gcgaattc                                          796
Arg
```

<210> SEQ ID NO 44
<211> LENGTH: 248
<212> TYPE: PRT
<213> ORGANISM: Sphingomonas melonis DC18

<400> SEQUENCE: 44

```
Met Thr Val Asp His Asp Ala Arg Ile Ser Leu Leu Ala Ala Ala
 1               5                  10                  15

Ile Gly Ala Ala Trp Leu Ala Ile His Val Gly Ala Ile Val Trp Trp
             20                  25                  30

Arg Trp Ser Pro Ala Thr Ala Val Leu Ala Ile Pro Val Val Leu Val
         35                  40                  45

Gln Ala Trp Leu Ser Thr Gly Leu Phe Ile Val Ala His Asp Cys Met
     50                  55                  60

His Gly Ser Phe Val Pro Gly Arg Pro Ala Val Asn Arg Thr Val Gly
 65                  70                  75                  80

Thr Leu Cys Leu Gly Ala Tyr Ala Gly Leu Ser Tyr Gly Gln Leu His
                 85                  90                  95

Pro Lys His His Ala His His Asp Ala Pro Gly Thr Ala Ala Asp Pro
             100                 105                 110

Asp Phe His Ala Gly Ala Pro Arg Ser Ala Leu Pro Trp Phe Ala Arg
         115                 120                 125

Phe Phe Thr Ser Tyr Tyr Thr His Gly Gln Ile Leu Arg Ile Thr Val
     130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                 165                 170                 175

Phe Gly Thr Phe Leu Pro His Arg His Gly Asp Thr Pro Phe Ala Asp
             180                 185                 190

Ala His Asn Ala Arg Ser Asn Gly Trp Pro Trp Leu Ala Ser Leu Ala
         195                 200                 205

Thr Cys Phe His Phe Gly Ala Tyr His His Glu His His Leu Ser Pro
     210                 215                 220

Trp Thr Pro Trp Trp Gln Leu Pro Arg Val Gly Gln Pro Ala Ala Gly
225                 230                 235                 240

His Arg Ser Leu Ser Lys Asp Arg
                 245

<210> SEQ ID NO 45
<211> LENGTH: 796
<212> TYPE: DNA
<213> ORGANISM: Sphingomonas melonis DC18
<220> FEATURE:
<221> NAME/KEY: CDS
<222> LOCATION: (32)..(778)

<400> SEQUENCE: 45
ccatggccct ttctagaaag gaggaataaa c atg acc gtc gat cac gac gca      52
                                  Met Thr Val Asp His Asp Ala
                                   1               5 cgg atc agc ctg ctg ctg gcc gca gcc atc ggc gcc gcg tgg ctg gcg    100
Arg Ile Ser Leu Leu Leu Ala Ala Ala Ile Gly Ala Ala Trp Leu Ala
         10                  15                  20 atc cat gtc ggg gcg atc gtg tgg tgg cga tgg agc ccg gcg acg gcg    148
Ile His Val Gly Ala Ile Val Trp Trp Arg Trp Ser Pro Ala Thr Ala
 25                  30                  35 gtg ctc gcg atc ccc gtc gtg ctc gta cag gcg tgg ctg agc acc ggc    196
Val Leu Ala Ile Pro Val Val Leu Val Gln Ala Trp Leu Ser Thr Gly
40                  45                  50                  55 ctg ttc atc gtc gcg cac gat tgc atg cac gga tcg ttc gtg ccc ggc    244
Leu Phe Ile Val Ala His Asp Cys Met His Gly Ser Phe Val Pro Gly
                 60                  65                  70
```

-continued

```
cgg ccc gcg gtc aac cgg acc gtc ggg acg ctg tgc ctc ggc gcc tat      292
Arg Pro Ala Val Asn Arg Thr Val Gly Thr Leu Cys Leu Gly Ala Tyr
         75                  80                  85 gcg gga ctg tcc tat ggc cag ctc cat ccc aag cat cat gcg cat cac      340
Ala Gly Leu Ser Tyr Gly Gln Leu His Pro Lys His His Ala His His
         90                  95                 100 gat gcg ccg ggc acc gcc gcc gac ccc gat ttc cat gcc ggc gcg ccg      388
Asp Ala Pro Gly Thr Ala Ala Asp Pro Asp Phe His Ala Gly Ala Pro
    105                 110                 115 cga tcc gca ctg ccg tgg ttc gcg cgc ttc ttc acc agc tat tac acg      436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gtg ctg tac atg ctg      484
His Gly Gln Ile Leu Arg Ile Thr Ala Ala Ala Val Leu Tyr Met Leu
                140                 145                 150 ctc ggt gtg tcg ctg ctc aac atc gtc gtg ttc tgg gcg ttg ccg gcg      532
Leu Gly Val Ser Leu Leu Asn Ile Val Val Phe Trp Ala Leu Pro Ala
                155                 160                 165 ctg atc gcg ctg gcg cag ctg ttc gtc ttc ggc acc ttc ctg ccg cat      580
Leu Ile Ala Leu Ala Gln Leu Phe Val Phe Gly Thr Phe Leu Pro His
        170                 175                 180 cgc cac ggc gac acg ccg ttc gcg gac gcg cac aat gcc cgc agc aac      628
Arg His Gly Asp Thr Pro Phe Ala Asp Ala His Asn Ala Arg Ser Asn
    185                 190                 195 ggc tgg cca cgg ctg gcg tcg ctg gcg acc tgc ttc cac ttc ggc acc      676
Gly Trp Pro Arg Leu Ala Ser Leu Ala Thr Cys Phe His Phe Gly Thr
200                 205                 210                 215 tat cat cac gaa cat cac ctg agc ccg tgg acg ccc tgg tgg cag ttg      724
Tyr His His Glu His His Leu Ser Pro Trp Thr Pro Trp Trp Gln Leu
                220                 225                 230 ccg cgc gtc ggc cag cct gcc gcc gga cac cgg tcg tta agc aaa gac      772
Pro Arg Val Gly Gln Pro Ala Ala Gly His Arg Ser Leu Ser Lys Asp
        235                 240                 245 cgg tag actagtaagg gcgaattc                                          796
Arg
```

<210> SEQ ID NO 46
<211> LENGTH: 248
<212> TYPE: PRT
<213> ORGANISM: Sphingomonas melonis DC18

<400> SEQUENCE: 46

```
Met Thr Val Asp His Asp Ala Arg Ile Ser Leu Leu Ala Ala Ala
1               5                   10                  15

Ile Gly Ala Ala Trp Leu Ala Ile His Val Gly Ala Ile Val Trp Trp
            20                  25                  30

Arg Trp Ser Pro Ala Thr Ala Val Leu Ala Ile Pro Val Val Leu Val
        35                  40                  45

Gln Ala Trp Leu Ser Thr Gly Leu Phe Ile Val Ala His Asp Cys Met
    50                  55                  60

His Gly Ser Phe Val Pro Gly Arg Pro Ala Val Asn Arg Thr Val Gly
65                  70                  75                  80

Thr Leu Cys Leu Gly Ala Tyr Ala Gly Leu Ser Tyr Gly Gln Leu His
                85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125
```

```
Phe Phe Thr Ser Tyr Tyr Thr His Gly Gln Ile Leu Arg Ile Thr Ala
    130                 135                 140
Ala Ala Val Leu Tyr Met Leu Leu Gly Val Ser Leu Leu Asn Ile Val
145                 150                 155                 160
Val Phe Trp Ala Leu Pro Ala Leu Ile Ala Leu Ala Gln Leu Phe Val
                165                 170                 175
Phe Gly Thr Phe Leu Pro His Arg His Gly Asp Thr Pro Phe Ala Asp
                180                 185                 190
Ala His Asn Ala Arg Ser Asn Gly Trp Pro Arg Leu Ala Ser Leu Ala
            195                 200                 205
Thr Cys Phe His Phe Gly Thr Tyr His His Glu His His Leu Ser Pro
    210                 215                 220
Trp Thr Pro Trp Trp Gln Leu Pro Arg Val Gly Gln Pro Ala Ala Gly
225                 230                 235                 240

His Arg Ser Leu Ser Lys Asp Arg
                245
```

<210> SEQ ID NO 47
<211> LENGTH: 796
<212> TYPE: DNA
<213> ORGANISM: Sphingomonas melonis DC18

<400> SEQUENCE: 47

```
ccatggccct ttctagaaag gaggaataaa catgaccgtc gatcacgacg cacggatcag    60
cctgctgctg gccgcagcca tcggcgccgc gtggctggcg atccatgtcg ggcgatcgt    120
gtggtggcga tggagcccgg cgacggcggt gctcgcgatc cccgtcgtgc tcgtacaggc    180
gtggctgagc accggcctgt tcatcgtcgc gcacgattgc atgcacggat cgttcgtgcc    240
cggccggccc gcggtcaacc ggaccgtcgg gacgctgtgc ctcggtgcct atgcgggact    300
gtcctatggc cagctccatc ccaagcatca tgcgcatcac gatgcgccgg gcaccgccgc    360
cgaccccgat ttccatgccg gcgcgccgcg atccgcactg ccgtggttcg cgcgcttctt    420
caccagctat tacacgcacg ccagatcct ccggatcacc gcggcggcgg tgctgtacat    480
gctgctcggt gtgtcgctgc tcaacatcgt cgtgttctgg gcgttgccgg cgctgatcgc    540
gctggcgcag ctgttcgtct cggcaccttc cctgccgcat cgccacgcg acacgccgtt    600
cgcggacgcg cacaatgccc gcagcaacgg ctggccacgg ctggcgtcgc tggcgacctg    660
cttccacttc ggcacctatc atcacgaaca tcacctgagc ccgtggacgc cctggtggca    720
gttgccgcgc gtcggccagc ctgccgccgg acaccggtcg ttaagcaaag accggtagac    780
tagtaagggc gaattc                                                    796
```

<210> SEQ ID NO 48
<211> LENGTH: 796
<212> TYPE: DNA
<213> ORGANISM: Sphingomonas melonis DC18

<400> SEQUENCE: 48

```
ccatggccct ttctagaaag gaggaataaa catgacagtc gatcacgacg cacggatcag    60
cctgctgctg gccgcagcca tcggcgccgc gtggctggcg atccatgtcg ggcgatcgt    120
gtggtggcga tggagcccgg cgacggcggt gctcgcgatc cccgtcgtgc tcgtacaggc    180
gtggctgagc accggcctgt tcatcgtcgc gcacgattgc atgcacggat cgttcgtgcc    240
cggccggccc gcggtcaacc ggaccgtcgg gacgctgtgc ctcggcgcct atgcgggact    300
gtcctatggc cagctccatc ccaagcatca tgcgcatcac gatgcgccgg gcaccgccgc    360
```

```
cgaccccgat tccatgccg gcgcgccgcg atccgcactg ccgtggttcg cgcgcttctt    420
caccagctat tacacgcacg gccagatcct ccggatcacc gcggcggcgg tgctgtacat    480
gctgctcggt gtgtcgctgc tcaacatcgt cgtgttctgg gcgttgccgg cgctgatcgc    540
gctggcgcag ctgttcgtct tcggcacctt cctgccgcat cgccacggcg acacgccgtt    600
cgcggacgcg cacaatgccc gcagcaacgg ctggccacgg ctggcgtcgc tggcgacctg    660
cttccacttc ggcacctatc atcacgaaca tcacctgagc ccgtggacgc cctggtggca    720
gttgccgcgc gtcggccagc tgccgccgg acaccggtcg ttaagcaaag accggtagac    780
tagtaagggc gaattc                                                    796

<210> SEQ ID NO 49
<211> LENGTH: 796
<212> TYPE: DNA
<213> ORGANISM: Sphingomonas melonis DC18
<220> FEATURE:
<221> NAME/KEY: CDS
<222> LOCATION: (32)..(778)

<400> SEQUENCE: 49
ccatggccct ttctagaaag gaggaataaa c atg acc gtc gat cac gac gca          52
                                  Met Thr Val Asp His Asp Ala
                                   1               5 cgg atc agc ctg ctg ctg gcc gca gcc atc ggc gcc gcg tgg ctg gcg        100
Arg Ile Ser Leu Leu Leu Ala Ala Ala Ile Gly Ala Ala Trp Leu Ala
         10                  15                  20 atc cat gtc ggg gcg atc gtg tgg tgg cga tgg agc ccg gcg acg gcg        148
Ile His Val Gly Ala Ile Val Trp Trp Arg Trp Ser Pro Ala Thr Ala
     25                  30                  35 gtg ctc gcg atc ccc gtc gtg ctc gta cag gcg tgg ctg agc acc ggc        196
Val Leu Ala Ile Pro Val Val Leu Val Gln Ala Trp Leu Ser Thr Gly
40                  45                  50                  55 ctg ttc atc gtc gcg cac gat tgc atg cac gga tcg ttc gtg ccc ggc        244
Leu Phe Ile Val Ala His Asp Cys Met His Gly Ser Phe Val Pro Gly
                 60                  65                  70 cgg ccc gcg gtc aac cgg acc gtc ggg acg ctg tgc ctc ggc gcc tat        292
Arg Pro Ala Val Asn Arg Thr Val Gly Thr Leu Cys Leu Gly Ala Tyr
             75                  80                  85 gcg gga ctg tcc tat ggc cag ctc cat ccc aag cat cat gcg cat cac        340
Ala Gly Leu Ser Tyr Gly Gln Leu His Pro Lys His His Ala His His
         90                  95                 100 gat gcg cca ggc acc gcc gcc gac ccc gat ttc cat gcc ggc gcg ccg        388
Asp Ala Pro Gly Thr Ala Ala Asp Pro Asp Phe His Ala Gly Ala Pro
    105                 110                 115 cga tcc gca ctg ccg tgg ttc gcg cgc ttc ttc gcc agc tat tac acg        436
Arg Ser Ala Leu Pro Trp Phe Ala Arg Phe Phe Ala Ser Tyr Tyr Thr
120                 125                 130                 135 cac ggc cag atc ctc cgg atc acc gcg gcg gcg gtg ctg tac atg ctg        484
His Gly Gln Ile Leu Arg Ile Thr Ala Ala Ala Val Leu Tyr Met Leu
                140                 145                 150 ctc ggt gtg tcg ctg ctc aac atc gtc gtg ttc tgg gcg ttg ccg gcg        532
Leu Gly Val Ser Leu Leu Asn Ile Val Val Phe Trp Ala Leu Pro Ala
            155                 160                 165 ctg atc gcg ctg gcg cag ctg ttc gtc ttc ggc acc ttc ctg ccg cat        580
Leu Ile Ala Leu Ala Gln Leu Phe Val Phe Gly Thr Phe Leu Pro His
        170                 175                 180 cgc cac ggc gac acg ccg ttc gcg gac gcg cac aat gcc cgc agc aac        628
Arg His Gly Asp Thr Pro Phe Ala Asp Ala His Asn Ala Arg Ser Asn
    185                 190                 195
```

|  |  |  |  |  |  |  |  |  |  |  |  |  |  |  |  |
|---|---|---|---|---|---|---|---|---|---|---|---|---|---|---|---|
| ggc | tgg | cca | cgg | ctg | gcg | tcg | ctg | gcg | acc | tgc | ttc | cac | ttc | ggc | acc | 676 |
| Gly | Trp | Pro | Arg | Leu | Ala | Ser | Leu | Ala | Thr | Cys | Phe | His | Phe | Gly | Thr |  |
| 200 |  |  |  | 205 |  |  |  |  | 210 |  |  |  |  | 215 |  |  |

|  |  |  |  |  |  |  |  |  |  |  |  |  |  |  |  |
|---|---|---|---|---|---|---|---|---|---|---|---|---|---|---|---|
| tat | cat | cac | gaa | cat | cac | ctg | agc | ccg | tgg | acg | ccc | tgg | tgg | cag | ttg | 724 |
| Tyr | His | His | Glu | His | His | Leu | Ser | Pro | Trp | Thr | Pro | Trp | Trp | Gln | Leu |  |
|  |  |  |  | 220 |  |  |  |  | 225 |  |  |  |  | 230 |  |  |

|  |  |  |  |  |  |  |  |  |  |  |  |  |  |  |  |
|---|---|---|---|---|---|---|---|---|---|---|---|---|---|---|---|
| ccg | cgc | gtc | ggc | cag | cct | gcc | gcc | gga | cac | cgg | tcg | tta | agc | aaa | gac | 772 |
| Pro | Arg | Val | Gly | Gln | Pro | Ala | Ala | Gly | His | Arg | Ser | Leu | Ser | Lys | Asp |  |
|  |  |  | 235 |  |  |  |  | 240 |  |  |  |  | 245 |  |  |  |

|  |  |  |
|---|---|---|
| cgg | tag actagtaagg gcgaattc | 796 |
| Arg |  |  |

<210> SEQ ID NO 50
<211> LENGTH: 248
<212> TYPE: PRT
<213> ORGANISM: Sphingomonas melonis DC18

<400> SEQUENCE: 50

Met Thr Val Asp His Asp Ala Arg Ile Ser Leu Leu Ala Ala
1               5                   10                  15

Ile Gly Ala Ala Trp Leu Ala Ile His Val Gly Ala Ile Val Trp Trp
            20                  25                  30

Arg Trp Ser Pro Ala Thr Ala Val Leu Ala Ile Pro Val Val Leu Val
        35                  40                  45

Gln Ala Trp Leu Ser Thr Gly Leu Phe Ile Val Ala His Asp Cys Met
    50                  55                  60

His Gly Ser Phe Val Pro Gly Arg Pro Ala Val Asn Arg Thr Val Gly
65                  70                  75                  80

Thr Leu Cys Leu Gly Ala Tyr Ala Gly Leu Ser Tyr Gly Gln Leu His
                85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125

Phe Phe Ala Ser Tyr Tyr Thr His Gly Gln Ile Leu Arg Ile Thr Ala
    130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Ala His Asn Ala Arg Ser Asn Gly Trp Pro Arg Leu Ala Ser Leu Ala
        195                 200                 205

Thr Cys Phe His Phe Gly Thr Tyr His His Glu His His Leu Ser Pro
    210                 215                 220

Trp Thr Pro Trp Trp Gln Leu Pro Arg Val Gly Gln Pro Ala Ala Gly
225                 230                 235                 240

His Arg Ser Leu Ser Lys Asp Arg
                245

<210> SEQ ID NO 51
<211> LENGTH: 796
<212> TYPE: DNA
<213> ORGANISM: Sphingomonas melonis DC18
<220> FEATURE:
<221> NAME/KEY: CDS

```
<222> LOCATION: (32)..(778)

<400> SEQUENCE: 51
ccatggccct ttctagaaag gaggaataaa c atg acc gtc gat cac gac gca         52
                                   Met Thr Val Asp His Asp Ala
                                     1               5 cgg atc agc ctg ctg ctg gcc gca gcc atc ggc gcc gca tgg ctg gcg        100
Arg Ile Ser Leu Leu Leu Ala Ala Ala Ile Gly Ala Ala Trp Leu Ala
         10                  15                  20 atc cat gtc ggg gcg atc gtg tgg tgg cga tgg agc ccg gcg acg gcg        148
Ile His Val Gly Ala Ile Val Trp Trp Arg Trp Ser Pro Ala Thr Ala
     25                  30                  35 gtg ctc gcg atc ccc gtc gtg ctc gta cag gcg tgg ctg agc acc ggc        196
Val Leu Ala Ile Pro Val Val Leu Val Gln Ala Trp Leu Ser Thr Gly
 40                  45                  50                  55 ctg ttc atc gtc gcg cac gat tgc atg cac gga tcg ttc gtg ccc ggc        244
Leu Phe Ile Val Ala His Asp Cys Met His Gly Ser Phe Val Pro Gly
                 60                  65                  70 cgg ccc gcg gtc aac cgg acc gtc ggg acg ctg tgc ctc ggc gcc tat        292
Arg Pro Ala Val Asn Arg Thr Val Gly Thr Leu Cys Leu Gly Ala Tyr
             75                  80                  85 gcg gga ctg tcc tat ggc cag ctc cat ccc aag cat cat gcg cat cac        340
Ala Gly Leu Ser Tyr Gly Gln Leu His Pro Lys His His Ala His His
         90                  95                 100 gat gcg ccg ggc acc gcc gcc gac ccc gat ttc cat gcc ggc gcg ccg        388
Asp Ala Pro Gly Thr Ala Ala Asp Pro Asp Phe His Ala Gly Ala Pro
    105                 110                 115 cga tcc gca ctg ccg tgg ttc gcg cgc ttc ttc acc agc tat tac acg        436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gtg ctg tac atg ctg        484
His Gly Gln Ile Leu Arg Ile Thr Ala Ala Ala Val Leu Tyr Met Leu
                140                 145                 150 ctc ggt gtg tcg ctg ctc aac atc gtc gtg ttc tgg gcg ttg ccg gcg        532
Leu Gly Val Ser Leu Leu Asn Ile Val Val Phe Trp Ala Leu Pro Ala
            155                 160                 165 ctg atc gcg ctg gcg cag ctg ttc gtc ttc ggc acc ttc ctg ccg cat        580
Leu Ile Ala Leu Ala Gln Leu Phe Val Phe Gly Thr Phe Leu Pro His
        170                 175                 180 cgc cac ggc gac acg ccg ttc gcg gac gcg cac aat gcc cgc agc aac        628
Arg His Gly Asp Thr Pro Phe Ala Asp Ala His Asn Ala Arg Ser Asn
    185                 190                 195 ggc tgg cca cgg ctg gcg tcg ctg gcg acc tgc ttc cac ttc ggc acc        676
Gly Trp Pro Arg Leu Ala Ser Leu Ala Thr Cys Phe His Phe Gly Thr
200                 205                 210                 215 tat cat cac gaa cat cac ctg agc ccg cgg acg ccc tgg tgg cag ttg        724
Tyr His His Glu His His Leu Ser Pro Arg Thr Pro Trp Trp Gln Leu
                220                 225                 230 ccg cgc gtc ggc cag cct gcc gcc gga cac cgg tcg tta agc aaa gac        772
Pro Arg Val Gly Gln Pro Ala Ala Gly His Arg Ser Leu Ser Lys Asp
            235                 240                 245 cgg tag actagtaagg gcgaattc                                            796
Arg

<210> SEQ ID NO 52
<211> LENGTH: 248
<212> TYPE: PRT
<213> ORGANISM: Sphingomonas melonis DC18

<400> SEQUENCE: 52
```

```
Met Thr Val Asp His Asp Ala Arg Ile Ser Leu Leu Ala Ala Ala
1               5                   10                  15

Ile Gly Ala Ala Trp Leu Ala Ile His Val Gly Ala Ile Val Trp Trp
                20                  25                  30

Arg Trp Ser Pro Ala Thr Ala Val Leu Ala Ile Pro Val Val Leu Val
            35                  40                  45

Gln Ala Trp Leu Ser Thr Gly Leu Phe Ile Val Ala His Asp Cys Met
50                  55                  60

His Gly Ser Phe Val Pro Gly Arg Pro Ala Val Asn Arg Thr Val Gly
65              70                  75                  80

Thr Leu Cys Leu Gly Ala Tyr Ala Gly Leu Ser Tyr Gly Gln Leu His
                85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125

Phe Phe Thr Ser Tyr Tyr Thr His Gly Gln Ile Leu Arg Ile Thr Ala
130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Ala His Asn Ala Arg Ser Asn Gly Trp Pro Arg Leu Ala Ser Leu Ala
        195                 200                 205

Thr Cys Phe His Phe Gly Thr Tyr His His Glu His His Leu Ser Pro
    210                 215                 220

Arg Thr Pro Trp Trp Gln Leu Pro Arg Val Gly Gln Pro Ala Ala Gly
225                 230                 235                 240

His Arg Ser Leu Ser Lys Asp Arg
                245
```

<210> SEQ ID NO 53
<211> LENGTH: 796
<212> TYPE: DNA
<213> ORGANISM: Sphingomonas melonis DC18
<220> FEATURE:
<221> NAME/KEY: CDS
<222> LOCATION: (32)..(778)

<400> SEQUENCE: 53

```
ccatggccct ttctagaaag gaggaataaa c atg acc gtc gat cac gac gca      52
                                   Met Thr Val Asp His Asp Ala
                                   1               5 cgg atc agc ctg ctg ctg gcc gca gcc atc ggc gcc gcg tgg ctg gcg   100
Arg Ile Ser Leu Leu Leu Ala Ala Ala Ile Gly Ala Ala Trp Leu Ala
        10                  15                  20 atc cat gtc ggg gcg atc atg tgg tgg cga tgg agc ccg gcg acg gcg   148
Ile His Val Gly Ala Ile Met Trp Trp Arg Trp Ser Pro Ala Thr Ala
    25                  30                      35 gtg ctc gcg atc ccc gtc gtg ctc gta cag gcg tgg ctg agc acc ggc   196
Val Leu Ala Ile Pro Val Val Leu Val Gln Ala Trp Leu Ser Thr Gly
40                  45                  50                  55 ctg ttc atc gtc gcg cac gat tgc atg cac gga tcg ttc gtg ccc ggc   244
Leu Phe Ile Val Ala His Asp Cys Met His Gly Ser Phe Val Pro Gly
                60                  65                  70
```

```
cgg ccc gcg gtc aac cgg acc gtc ggg acg ctg tgc ctc ggc gcc tat      292
Arg Pro Ala Val Asn Arg Thr Val Gly Thr Leu Cys Leu Gly Ala Tyr
         75                  80                  85 gcg gga ctg tcc tat ggc cag ctc cat ccc aag cat cat gcg cat cac      340
Ala Gly Leu Ser Tyr Gly Gln Leu His Pro Lys His His Ala His His
         90                  95                 100 gat gcg ccg ggc acc gcc gcc gac ccc gat ttc cat gcc ggc gcg ccg      388
Asp Ala Pro Gly Thr Ala Ala Asp Pro Asp Phe His Ala Gly Ala Pro
105                 110                 115 cga tcc gca ctg ccg tgg ttc gcg cgc ttc ttc gcc agc tat tac acg      436
Arg Ser Ala Leu Pro Trp Phe Ala Arg Phe Phe Ala Ser Tyr Tyr Thr
120                 125                 130                 135 cac ggc cag atc ctc cgg atc acc gcg gcg gcg gtg ctg tac atg ctg      484
His Gly Gln Ile Leu Arg Ile Thr Ala Ala Ala Val Leu Tyr Met Leu
        140                 145                 150 ctc ggt gtg tcg ctg ctc aac atc gtc gtg ttc tgg gcg ttg ccg gcg      532
Leu Gly Val Ser Leu Leu Asn Ile Val Val Phe Trp Ala Leu Pro Ala
        155                 160                 165 ctg atc gcg ctg gcg cag ctg ttc gtc ttc ggc acc ttc ctg ccg cat      580
Leu Ile Ala Leu Ala Gln Leu Phe Val Phe Gly Thr Phe Leu Pro His
        170                 175                 180 cgc cac ggc gac acg ccg ttc gcg gac gcg cac aat gcc cgc agc aac      628
Arg His Gly Asp Thr Pro Phe Ala Asp Ala His Asn Ala Arg Ser Asn
185                 190                 195 ggc tgg cca cgg ctg gcg tcg ctg gcg acc tgc ttc cac ttc ggc acc      676
Gly Trp Pro Arg Leu Ala Ser Leu Ala Thr Cys Phe His Phe Gly Thr
200                 205                 210                 215 tat cat cac gaa cat cac ctg agc ccg tgg acg ccc tgg tgg cag ttg      724
Tyr His His Glu His His Leu Ser Pro Trp Thr Pro Trp Trp Gln Leu
            220                 225                 230 ccg cgc gtc ggc cag cct gcc gcc gga cac cgg tcg tta agc aaa gac      772
Pro Arg Val Gly Gln Pro Ala Ala Gly His Arg Ser Leu Ser Lys Asp
            235                 240                 245 cgg tag actagtaagg gcgaattc                                          796
Arg

<210> SEQ ID NO 54
<211> LENGTH: 248
<212> TYPE: PRT
<213> ORGANISM: Sphingomonas melonis DC18

<400> SEQUENCE: 54

Met Thr Val Asp His Asp Ala Arg Ile Ser Leu Leu Ala Ala Ala
1               5                   10                  15

Ile Gly Ala Ala Trp Leu Ala Ile His Val Gly Ala Ile Met Trp Trp
            20                  25                  30

Arg Trp Ser Pro Ala Thr Ala Val Leu Ala Ile Pro Val Val Leu Val
        35                  40                  45

Gln Ala Trp Leu Ser Thr Gly Leu Phe Ile Val Ala His Asp Cys Met
    50                  55                  60

His Gly Ser Phe Val Pro Gly Arg Pro Ala Val Asn Arg Thr Val Gly
65                  70                  75                  80

Thr Leu Cys Leu Gly Ala Tyr Ala Gly Leu Ser Tyr Gly Gln Leu His
                85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125
```

```
Phe Phe Ala Ser Tyr Tyr Thr His Gly Gln Ile Leu Arg Ile Thr Ala
    130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Ala His Asn Ala Arg Ser Asn Gly Trp Pro Arg Leu Ala Ser Leu Ala
        195                 200                 205

Thr Cys Phe His Phe Gly Thr Tyr His His Glu His His Leu Ser Pro
    210                 215                 220

Trp Thr Pro Trp Trp Gln Leu Pro Arg Val Gly Gln Pro Ala Ala Gly
225                 230                 235                 240

His Arg Ser Leu Ser Lys Asp Arg
                245

<210> SEQ ID NO 55
<211> LENGTH: 796
<212> TYPE: DNA
<213> ORGANISM: Sphingomonas melonis DC18
<220> FEATURE:
<221> NAME/KEY: CDS
<222> LOCATION: (32)..(778)

<400> SEQUENCE: 55
ccatggccct ttctagaaag gaggaataaa c atg acc gtc gat cac gac gca      52
                                  Met Thr Val Asp His Asp Ala
                                    1               5 cgg atc agc ctg ctg ctg gcc gca gcc atc ggc gcc gcg tgg ctg gcg    100
Arg Ile Ser Leu Leu Leu Ala Ala Ala Ile Gly Ala Ala Trp Leu Ala
         10                  15                  20 atc cat gtc ggg gcg atc gtg tgg tgg cga tgg agc ccg gcg acg gcg    148
Ile His Val Gly Ala Ile Val Trp Trp Arg Trp Ser Pro Ala Thr Ala
     25                  30                  35 gtg ctc gcg atc ccc gtc gtg ctc gta cag gcg tgg ctg agc acc ggc    196
Val Leu Ala Ile Pro Val Val Leu Val Gln Ala Trp Leu Ser Thr Gly
 40                  45                  50                  55 ctg ttc atc gtc gcg cac gat tgc atg cac gga tcg ttc gtg ccc ggc    244
Leu Phe Ile Val Ala His Asp Cys Met His Gly Ser Phe Val Pro Gly
                 60                  65                  70 cgg ccc gcg gtc aac cgg acc gtc ggg acg ctg tgc ctc ggc gcc tat    292
Arg Pro Ala Val Asn Arg Thr Val Gly Thr Leu Cys Leu Gly Ala Tyr
             75                  80                  85 gcg gga ctg tcc tat ggc cag ctc cat ccc aag cat cat gcg cat cac    340
Ala Gly Leu Ser Tyr Gly Gln Leu His Pro Lys His His Ala His His
         90                  95                 100 gat gcg ccg ggc acc gcc gcc gac ccc gat ttc cat gcc ggc gcg ccg    388
Asp Ala Pro Gly Thr Ala Ala Asp Pro Asp Phe His Ala Gly Ala Pro
     105                 110                 115 cga tcc gca ctg ccg tgg ttc gcg cgc ttc ttc acc agc tat tac acg    436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gag ctg tac atg ctg    484
His Gly Gln Ile Leu Arg Ile Thr Ala Ala Ala Glu Leu Tyr Met Leu
                 140                 145                 150 ctc ggt gtg tcg ctg ctc aac atc gtc gtg ttc tgg gcg ttg ccg gcg    532
Leu Gly Val Ser Leu Leu Asn Ile Val Val Phe Trp Ala Leu Pro Ala
             155                 160                 165
```

```
ctg atc gcg ctg gcg cag ctg ttc gtc ttc ggc acc ttc ctg ccg cat    580
Leu Ile Ala Leu Ala Gln Leu Phe Val Phe Gly Thr Phe Leu Pro His
        170                 175                 180 cgc cac ggc gac acg ccg ttc gcg gac gcg cac aat gcc cgc agc aac    628
Arg His Gly Asp Thr Pro Phe Ala Asp Ala His Asn Ala Arg Ser Asn
185                 190                 195 ggc tgg cca cgg ctg gcg tcg ctg gcg acc tgc ttc cac ttc ggc acc    676
Gly Trp Pro Arg Leu Ala Ser Leu Ala Thr Cys Phe His Phe Gly Thr
200                 205                 210                 215 tat cat cac gaa cat cac ctg agc ccg tgg acg ccc tgg tgg cag ttg    724
Tyr His His Glu His His Leu Ser Pro Trp Thr Pro Trp Trp Gln Leu
            220                 225                 230 ccg cgc gtc ggc cag cct gcc gcc gga cac cgg tcg tta agc aaa gac    772
Pro Arg Val Gly Gln Pro Ala Ala Gly His Arg Ser Leu Ser Lys Asp
        235                 240                 245 cgg tag actagtaagg gcgaattc                                        796
Arg

<210> SEQ ID NO 56
<211> LENGTH: 248
<212> TYPE: PRT
<213> ORGANISM: Sphingomonas melonis DC18

<400> SEQUENCE: 56

Met Thr Val Asp His Asp Ala Arg Ile Ser Leu Leu Ala Ala Ala
1               5                   10                  15

Ile Gly Ala Ala Trp Leu Ala Ile His Val Gly Ala Ile Val Trp Trp
                20                  25                  30

Arg Trp Ser Pro Ala Thr Ala Val Leu Ala Ile Pro Val Val Leu Val
            35                  40                  45

Gln Ala Trp Leu Ser Thr Gly Leu Phe Ile Val Ala His Asp Cys Met
    50                  55                  60

His Gly Ser Phe Val Pro Gly Arg Pro Ala Val Asn Arg Thr Val Gly
65                  70                  75                  80

Thr Leu Cys Leu Gly Ala Tyr Ala Gly Leu Ser Tyr Gly Gln Leu His
                85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125

Phe Phe Thr Ser Tyr Tyr Thr His Gly Gln Ile Leu Arg Ile Thr Ala
    130                 135                 140

Ala Ala Glu Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Ala His Asn Ala Arg Ser Asn Gly Trp Pro Arg Leu Ala Ser Leu Ala
        195                 200                 205

Thr Cys Phe His Phe Gly Thr Tyr His His Glu His His Leu Ser Pro
    210                 215                 220

Trp Thr Pro Trp Trp Gln Leu Pro Arg Val Gly Gln Pro Ala Ala Gly
225                 230                 235                 240

His Arg Ser Leu Ser Lys Asp Arg
                245
```

<210> SEQ ID NO 57
<211> LENGTH: 796
<212> TYPE: DNA
<213> ORGANISM: Sphingomonas melonis DC18
<220> FEATURE:
<221> NAME/KEY: CDS
<222> LOCATION: (32)..(778)

<400> SEQUENCE: 57

| | | |
|---|---|---|
| ccatggccct ttctagaaag gaggaataaa c atg acc gtc gat cac gac gca<br>                                                      Met Thr Val Asp His Asp Ala<br>                                                       1              5 | | 52 |
| cgg atc agc ctg ctg ctg gcc gca gcc atc ggc gcc gcg tgg ctg gcg<br>Arg Ile Ser Leu Leu Leu Ala Ala Ala Ile Gly Ala Ala Trp Leu Ala<br>          10                    15                    20 | | 100 |
| atc cat gtc ggg gcg atc gtg tgg tgg cga tgg agc ccg gcg acg gcg<br>Ile His Val Gly Ala Ile Val Trp Trp Arg Trp Ser Pro Ala Thr Ala<br> 25                        30                    35 | | 148 |
| gtg ctc gcg atc ccc gtc gtg ctc gta cag gcg tgg ctg agc acc ggc<br>Val Leu Ala Ile Pro Val Val Leu Val Gln Ala Trp Leu Ser Thr Gly<br> 40                        45                    50                    55 | | 196 |
| ctg ttc atc gtc gcg cac gat tgc atg cac gga tcg ttc gtg ccc ggc<br>Leu Phe Ile Val Ala His Asp Cys Met His Gly Ser Phe Val Pro Gly<br>                     60                    65                                  70 | | 244 |
| cgg ccc gcg gtc aac cgg acc gtc ggg acg ctg tgc ctc ggc gcc tat<br>Arg Pro Ala Val Asn Arg Thr Val Gly Thr Leu Cys Leu Gly Ala Tyr<br>                75                        80                    85 | | 292 |
| gcg gga ctg tcc tat ggc cag ctc cat ccc aag cat cat gcg cat cac<br>Ala Gly Leu Ser Tyr Gly Gln Leu His Pro Lys His His Ala His His<br>          90                    95                            100 | | 340 |
| gat gcg ccg ggc acc gcc gcc gac ccc gat ttc cat gcc ggc gcg ccg<br>Asp Ala Pro Gly Thr Ala Ala Asp Pro Asp Phe His Ala Gly Ala Pro<br>105                          110                    115 | | 388 |
| cga tcc gca ctg ccg tgg ttc gcg cgc ttc ttc acc agc tat tac acg<br>Arg Ser Ala Leu Pro Trp Phe Ala Arg Phe Phe Thr Ser Tyr Tyr Thr<br>120                        125                    130                    135 | | 436 |
| cac ggc cag atc ctc cgg atc acc gcg gcg gcg gtg ctg tac atg ctg<br>His Gly Gln Ile Leu Arg Ile Thr Ala Ala Ala Val Leu Tyr Met Leu<br>                140                      145                    150 | | 484 |
| ctc ggt gtg tcg ctg ctc aac atc gtc gtg ttc tgg gcg ttg ccg gcg<br>Leu Gly Val Ser Leu Leu Asn Ile Val Val Phe Trp Ala Leu Pro Ala<br>                       155                        160                    165 | | 532 |
| ctg atc gcg ctg gcg cag ctg ttc gtc ttc ggc acc ttc ctg ccg cat<br>Leu Ile Ala Leu Ala Gln Leu Phe Val Phe Gly Thr Phe Leu Pro His<br>170                          175                    180 | | 580 |
| cgc cac ggc gac acg ccg ttc gcg gac gcg cac aat gcc cgc agc aac<br>Arg His Gly Asp Thr Pro Phe Ala Asp Ala His Asn Ala Arg Ser Asn<br>     185                        190                    195 | | 628 |
| ggc tgg cca cgg ctg gtg tcg ctg gcg acc tgc ttc cac ttc ggc gcc<br>Gly Trp Pro Arg Leu Val Ser Leu Ala Thr Cys Phe His Phe Gly Ala<br>200                          205                    210                    215 | | 676 |
| tat cat cac gaa cat cac ctg agc ccg tgg acg ccc tgg tgg cag ttg<br>Tyr His His Glu His His Leu Ser Pro Trp Thr Pro Trp Trp Gln Leu<br>                     220                        225                    230 | | 724 |
| ccg cgc gtc ggc cag cct gcc gcc gga cac cgg tcg tta agc aaa gac<br>Pro Arg Val Gly Gln Pro Ala Ala Gly His Arg Ser Leu Ser Lys Asp<br>                    235                        240                    245 | | 772 |
| cgg tag actagtaagg gcgaattc<br>Arg | | 796 |

<210> SEQ ID NO 58
<211> LENGTH: 248
<212> TYPE: PRT
<213> ORGANISM: Sphingomonas melonis DC18

<400> SEQUENCE: 58

```
Met Thr Val Asp His Asp Ala Arg Ile Ser Leu Leu Leu Ala Ala Ala
1               5                   10                  15

Ile Gly Ala Ala Trp Leu Ala Ile His Val Gly Ala Ile Val Trp Trp
            20                  25                  30

Arg Trp Ser Pro Ala Thr Ala Val Leu Ala Ile Pro Val Val Leu Val
        35                  40                  45

Gln Ala Trp Leu Ser Thr Gly Leu Phe Ile Val Ala His Asp Cys Met
    50                  55                  60

His Gly Ser Phe Val Pro Gly Arg Pro Ala Val Asn Arg Thr Val Gly
65                  70                  75                  80

Thr Leu Cys Leu Gly Ala Tyr Ala Gly Leu Ser Tyr Gly Gln Leu His
                85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125

Phe Phe Thr Ser Tyr Tyr Thr His Gly Gln Ile Leu Arg Ile Thr Ala
    130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Ala His Asn Ala Arg Ser Asn Gly Trp Pro Arg Leu Val Ser Leu Ala
        195                 200                 205

Thr Cys Phe His Phe Gly Ala Tyr His His Glu His His Leu Ser Pro
    210                 215                 220

Trp Thr Pro Trp Trp Gln Leu Pro Arg Val Gly Gln Pro Ala Ala Gly
225                 230                 235                 240

His Arg Ser Leu Ser Lys Asp Arg
                245
```

<210> SEQ ID NO 59
<211> LENGTH: 796
<212> TYPE: DNA
<213> ORGANISM: Sphingomonas melonis DC18

<400> SEQUENCE: 59

```
ccatggccct tctagaaaag gaggaataaa catgaccgtc gatcacgatg cacggatcag      60
cctgctgctg gccgcagcca tcggcgccgc gtggctggcg atccatgtcg gggcgatcgt     120
gtggtggcga tggagcccgg cgacggcggt gctcgcgatc ccgtcgtgc tcgtacaggc      180 gtggctgagc accggcctgt tcatcgtcgc gcacgattgc atgcacggat cgttcgtgcc     240
cggccggcct gcggtcaacc ggaccgtcgg gacgctgtgc ctcggcgcct atgcgggact     300
gtcctatggc cagctccatc ccaagcatca tgcgcatcac gatgcgccgg gcaccgccgc     360
cgaccccgat ttccatgccg gcgcgccgcg atccgcactg ccgtggttcg cgcgcttctt     420
caccagctat tacacgcacg gccagatcct ccggatcacc gcggcggcgg tgctgtacat     480
```

-continued

```
gctgctcggt gtgtcgctgc tcaacatcgt cgtgttctgg gcgttgccgg cgctgatcgc    540
gctggcgcag ctgttcgtct tcggcacctt cctgccgcat cgccacggcg acacgccgtt    600
cgcggacgcg cacaatgccc gcagcaacgg ctggccacgg ctggtgtcgc tggcgacctg    660
cttccacttc ggcgcctatc atcacgaaca tcacctgagc ccgtggacgc cctggtggca    720
gttgccgcgc gtcggccagc tgccgccgg acaccggtcg ttaagcaaag accggtagac    780
tagtaagggc gaattc                                                   796

<210> SEQ ID NO 60
<211> LENGTH: 796
<212> TYPE: DNA
<213> ORGANISM: Sphingomonas melonis DC18

<400> SEQUENCE: 60
ccatggccct ttctagaaag gaggaataaa catgaccgtc gatcacgacg cacggatcag     60
cctgctgctg gccgcagcca tcggcgccgc gtggctggcg atccatgtcg ggcgatcgt    120 gtggtggcga tggagcccgg cgacggcggt gctcgcgatc ccgtcgtgc tcgtacaggc    180 gtggctgagc accggcctgt tcatcgtcgc gcacgattgc atgcacggat cgttcgtgcc    240
cggccggccc gcggtcaacc ggaccgtcgg gacgctgtgc ctcggcgcct atgcgggact    300
gtcctatggc cagctccatc ccaagcatca tgccatcac gatgcgccgg caccgccgc    360 cgaccccgat ttccatgccg gcgcgccgcg atccgcactg ccgtggttcg cgcgcttctt    420
caccagctat tacacgcacg gccagatcct ccggatcacc gcggcggcgg tgctgtacat    480
gctgctcggt gtgtcgctgc tcaacatcgt cgtgttctgg gcgctgccgg cgctgatcgc    540
gctggcgcag ctgttcgtct tcggcacctt cctgccgcat cgccacggcg acacgccgtt    600
cgcggacgcg cacaatgccc gcagcaacgg ctggccgcgg ctggtgtcgc tggcgacctg    660
cttccacttc ggcgcctatc atcacgaaca tcacctgagc ccgtggacgc cctggtggca    720
gttgccgcgc gtcggccagc tgccgccgg acaccggtcg ttaagcaaag accggtagac    780
tagtaagggc gaattc                                                   796

<210> SEQ ID NO 61
<211> LENGTH: 796
<212> TYPE: DNA
<213> ORGANISM: Sphingomonas melonis DC18
<220> FEATURE:
<221> NAME/KEY: CDS
<222> LOCATION: (32)..(778)

<400> SEQUENCE: 61
ccatggccct ttctagaaag gaggaataaa c atg acc gtc gat cac gac gca        52
                                   Met Thr Val Asp His Asp Ala
                                     1               5 cgg atc agc ctg ctg ctg gcc gca gcc atc ggc gcc gcg tgg ctg gcg      100
Arg Ile Ser Leu Leu Leu Ala Ala Ala Ile Gly Ala Ala Trp Leu Ala
         10                  15                  20 atc cat gtc ggg gcg atc gtg tgg tgg cga tgg agc ccg gcg acg gcg      148
Ile His Val Gly Ala Ile Val Trp Trp Arg Trp Ser Pro Ala Thr Ala
 25                  30                  35 gtg ctc gcg atc ccc gtc gtg ctc gta cag gcg tgg ctg agc acc ggc      196
Val Leu Ala Ile Pro Val Val Leu Val Gln Ala Trp Leu Ser Thr Gly
 40                  45                  50                  55 ctg ttc atc gtc gcg cac gat tgc atg cac gga tcg ttc gtg ccc ggc      244
Leu Phe Ile Val Ala His Asp Cys Met His Gly Ser Phe Val Pro Gly
             60                  65                  70
```

```
cgg ccc gcg gtc aac cgg acc gtc ggg acg ctg tgc ctc ggc gcc tat        292
Arg Pro Ala Val Asn Arg Thr Val Gly Thr Leu Cys Leu Gly Ala Tyr
         75                  80                  85 gcg gga ctg tcc tat ggc cag ctc cat ccc aag cat cat gcg cat cac        340
Ala Gly Leu Ser Tyr Gly Gln Leu His Pro Lys His His Ala His His
         90                  95                 100 gat gcg ccg ggc acc gcc gcc gac ccc gat ttc cat gcc ggc gcg ccg        388
Asp Ala Pro Gly Thr Ala Ala Asp Pro Asp Phe His Ala Gly Ala Pro
105                 110                 115 cga tcc gca ctg ccg tgg ttc gcg cgc ttc ttc acc agc tat tac acg        436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gtg ctg tac atg ctg        484
His Gly Gln Ile Leu Arg Ile Thr Ala Ala Ala Val Leu Tyr Met Leu
                140                 145                 150 ctc ggt gcg tcg ctg ctc aac atc gtc gtg ttc tgg gcg ttg ccg gcg        532
Leu Gly Ala Ser Leu Leu Asn Ile Val Val Phe Trp Ala Leu Pro Ala
                155                 160                 165 ctg atc gcg ctg gcg cag ctg ttc gtc ttc ggc acc ttc ctg ccg cat        580
Leu Ile Ala Leu Ala Gln Leu Phe Val Phe Gly Thr Phe Leu Pro His
        170                 175                 180 cgc cac ggc gac acg ccg ttc gcg gac gcg cac aat gcc cgc agc aac        628
Arg His Gly Asp Thr Pro Phe Ala Asp Ala His Asn Ala Arg Ser Asn
185                 190                 195 ggc tgg cca cgg ctg gtg tcg ctg gcg acc tgc ttc cac ttc ggc gcc        676
Gly Trp Pro Arg Leu Val Ser Leu Ala Thr Cys Phe His Phe Gly Ala
200                 205                 210                 215 tat cat cac gaa cat cac ctg agc ccg tgg acg ccc tgg tgg cag ttg        724
Tyr His His Glu His His Leu Ser Pro Trp Thr Pro Trp Trp Gln Leu
                220                 225                 230 ccg cgc gtc ggc cag cct gcc gcc gga cac cgg tcg tta agc aaa gac        772
Pro Arg Val Gly Gln Pro Ala Ala Gly His Arg Ser Leu Ser Lys Asp
        235                 240                 245 cgg tag actagtaagg gcgaattc                                            796
Arg

<210> SEQ ID NO 62
<211> LENGTH: 248
<212> TYPE: PRT
<213> ORGANISM: Sphingomonas melonis DC18

<400> SEQUENCE: 62

Met Thr Val Asp His Asp Ala Arg Ile Ser Leu Leu Ala Ala Ala
1               5                   10                  15

Ile Gly Ala Ala Trp Leu Ala Ile His Val Gly Ala Ile Val Trp Trp
                20                  25                  30

Arg Trp Ser Pro Ala Thr Ala Val Leu Ala Ile Pro Val Val Leu Val
        35                  40                  45

Gln Ala Trp Leu Ser Thr Gly Leu Phe Ile Val Ala His Asp Cys Met
    50                  55                  60

His Gly Ser Phe Val Pro Gly Arg Pro Ala Val Asn Arg Thr Val Gly
65                  70                  75                  80

Thr Leu Cys Leu Gly Ala Tyr Ala Gly Leu Ser Tyr Gly Gln Leu His
                85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125
```

```
            Phe Phe Thr Ser Tyr Tyr Thr His Gly Gln Ile Leu Arg Ile Thr Ala
                130                 135                 140
            Ala Ala Val Leu Tyr Met Leu Leu Gly Ala Ser Leu Leu Asn Ile Val
            145                 150                 155                 160
            Val Phe Trp Ala Leu Pro Ala Leu Ile Ala Leu Ala Gln Leu Phe Val
                            165                 170                 175
            Phe Gly Thr Phe Leu Pro His Arg His Gly Asp Thr Pro Phe Ala Asp
                        180                 185                 190
            Ala His Asn Ala Arg Ser Asn Gly Trp Pro Arg Leu Val Ser Leu Ala
                    195                 200                 205
            Thr Cys Phe His Phe Gly Ala Tyr His His Glu His His Leu Ser Pro
                210                 215                 220
            Trp Thr Pro Trp Trp Gln Leu Pro Arg Val Gly Gln Pro Ala Ala Gly
            225                 230                 235                 240
            His Arg Ser Leu Ser Lys Asp Arg
                            245

<210> SEQ ID NO 63
<211> LENGTH: 796
<212> TYPE: DNA
<213> ORGANISM: Sphingomonas melonis DC18
<220> FEATURE:
<221> NAME/KEY: CDS
<222> LOCATION: (32)..(778)

<400> SEQUENCE: 63
ccatggccct ttctagaaag gaggaataaa c atg acc gtc gat cac gac gca           52
                                   Met Thr Val Asp His Asp Ala
                                    1               5 cgg atc agc ctg ctg ctg gcc gca gcc atc ggc gcc gcg tgg ctg gcg        100
Arg Ile Ser Leu Leu Leu Ala Ala Ala Ile Gly Ala Ala Trp Leu Ala
            10                  15                  20 atc cat gtc ggg gcg atc gtg tgg tgg cga tgg agc ccg gcg gcg gcg        148
Ile His Val Gly Ala Ile Val Trp Trp Arg Trp Ser Pro Ala Ala Ala
        25                  30                  35 gtg ttc gcg atc ccc gtc gtg ctc gta cag gcg tgg ctg agc acc ggc        196
Val Phe Ala Ile Pro Val Val Leu Val Gln Ala Trp Leu Ser Thr Gly
40                  45                  50                  55 ctg ttc atc gtc gca cac gat tgc atg cac gga tcg ttc gtg ccc ggc        244
Leu Phe Ile Val Ala His Asp Cys Met His Gly Ser Phe Val Pro Gly
                60                  65                  70 cgg ccc tcg gtc aac cgg acc gtc ggg acg ctg tgc ctc ggc gcc tat        292
Arg Pro Ser Val Asn Arg Thr Val Gly Thr Leu Cys Leu Gly Ala Tyr
            75                  80                  85 gcg gga ctg tcc tat ggc cag ctc cat ccc aag cat cat gcg cat cac        340
Ala Gly Leu Ser Tyr Gly Gln Leu His Pro Lys His His Ala His His
        90                  95                  100 gat gcg ccg ggc acc gcc gcc gac ccc gat ttc cat gcc ggc gcg ccg        388
Asp Ala Pro Gly Thr Ala Ala Asp Pro Asp Phe His Ala Gly Ala Pro
    105                 110                 115 cga tcc gca ctg ccg tgg ttc gcg cgc ttc ttc acc agc tat tac acg        436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gtg ctg tac atg ctg        484
His Gly Gln Ile Leu Arg Ile Thr Ala Ala Ala Val Leu Tyr Met Leu
                140                 145                 150 ctc ggt gtg tcg ctg ctc aac atc gtc gtg ttc tgg gcg ttg ccg gcg        532
Leu Gly Val Ser Leu Leu Asn Ile Val Val Phe Trp Ala Leu Pro Ala
            155                 160                 165
```

```
ctg atc gcg ctg gcg cag ctg ttc gtc ttc ggc acc ttc ctg ccg cat    580
Leu Ile Ala Leu Ala Gln Leu Phe Val Phe Gly Thr Phe Leu Pro His
        170                 175                 180 cgc cac ggc gac acg ccg ttc gcg gac gcg cac aat gcc cgc agc aac    628
Arg His Gly Asp Thr Pro Phe Ala Asp Ala His Asn Ala Arg Ser Asn
185                 190                 195 ggc tgg cca cgg ctg gtg tcg ctg gcg acc tgc ttc cac ttc ggc gcc    676
Gly Trp Pro Arg Leu Val Ser Leu Ala Thr Cys Phe His Phe Gly Ala
200                 205                 210                 215 tat cat cac gaa cat cac ctg agc ccg tgg acg ccc tgg tgg cag ttg    724
Tyr His His Glu His His Leu Ser Pro Trp Thr Pro Trp Trp Gln Leu
                220                 225                 230 ccg cgc gtc ggc cag cct gcc gcc gga cac cgg tcg tta ggc aaa gac    772
Pro Arg Val Gly Gln Pro Ala Ala Gly His Arg Ser Leu Gly Lys Asp
            235                 240                 245 cgg tag actagtaagg gcgaattc                                        796
Arg
```

<210> SEQ ID NO 64
<211> LENGTH: 248
<212> TYPE: PRT
<213> ORGANISM: Sphingomonas melonis DC18

<400> SEQUENCE: 64

Met Thr Val Asp His Asp Ala Arg Ile Ser Leu Leu Ala Ala Ala
1               5                   10                  15

Ile Gly Ala Ala Trp Leu Ala Ile His Val Gly Ala Ile Val Trp Trp
            20                  25                  30

Arg Trp Ser Pro Ala Ala Ala Val Phe Ala Ile Pro Val Val Leu Val
        35                  40                  45

Gln Ala Trp Leu Ser Thr Gly Leu Phe Ile Val Ala His Asp Cys Met
    50                  55                  60

His Gly Ser Phe Val Pro Gly Arg Pro Ser Val Asn Arg Thr Val Gly
65                  70                  75                  80

Thr Leu Cys Leu Gly Ala Tyr Ala Gly Leu Ser Tyr Gly Gln Leu His
                85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125

Phe Phe Thr Ser Tyr Tyr Thr His Gly Gln Ile Leu Arg Ile Thr Ala
    130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Ala His Asn Ala Arg Ser Asn Gly Trp Pro Arg Leu Val Ser Leu Ala
        195                 200                 205

Thr Cys Phe His Phe Gly Ala Tyr His His Glu His His Leu Ser Pro
    210                 215                 220

Trp Thr Pro Trp Trp Gln Leu Pro Arg Val Gly Gln Pro Ala Ala Gly
225                 230                 235                 240

His Arg Ser Leu Gly Lys Asp Arg
                245

<210> SEQ ID NO 65
<211> LENGTH: 796
<212> TYPE: DNA
<213> ORGANISM: Sphingomonas melonis DC18
<220> FEATURE:
<221> NAME/KEY: CDS
<222> LOCATION: (32)..(778)

<400> SEQUENCE: 65

```
ccatggccct ttctagaaag gaggaataaa c atg acc gtc gat cac gac gca        52
                                   Met Thr Val Asp His Asp Ala
                                   1               5 cgg atc agc ctg ctg ctg gcc gca gcc atc ggc gcc gcg tgg ctg gcg       100
Arg Ile Ser Leu Leu Leu Ala Ala Ala Ile Gly Ala Ala Trp Leu Ala
        10                  15                  20 atc cat gtc ggg gcg atc gtg tgg tgg cga tgg agc ccg gcg acg gcg       148
Ile His Val Gly Ala Ile Val Trp Trp Arg Trp Ser Pro Ala Thr Ala
 25                  30                  35 gtg ctc gcg atc ccc gtc gtg ctc gta cag gcg tgg ctg agc acc ggc       196
Val Leu Ala Ile Pro Val Val Leu Val Gln Ala Trp Leu Ser Thr Gly
40                  45                  50                  55 ctg ttc atc gtc gcg cac gat tgc atg cac gga tcg ttc gtg ccc ggc       244
Leu Phe Ile Val Ala His Asp Cys Met His Gly Ser Phe Val Pro Gly
                60                  65                  70 cgg ccc gcg gtc aac cgg acc gtc ggg acg ctg tgc ctc ggc gcc tat       292
Arg Pro Ala Val Asn Arg Thr Val Gly Thr Leu Cys Leu Gly Ala Tyr
             75                  80                  85 gcg gga ctg tcc tat ggc cag ctc cac ccc aag cat cat gcg cat cac       340
Ala Gly Leu Ser Tyr Gly Gln Leu His Pro Lys His His Ala His His
         90                  95                 100 gat gcg ccg ggc acc gcc gcc gac ccc gat ttc cat gcc ggc gcg ccg       388
Asp Ala Pro Gly Thr Ala Ala Asp Pro Asp Phe His Ala Gly Ala Pro
    105                 110                 115 cga tca gca ctg ccg tgg ttc gcg cgc ttc ttc acc agc tat tac acg       436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gtg ctg tac atg ctg       484
His Gly Gln Ile Leu Arg Ile Thr Ala Ala Ala Val Leu Tyr Met Leu
                140                 145                 150 ctc ggt gtg tcg ctg ctc aac atc gtc gtg ttc tgg gcg ttg ccg gcg       532
Leu Gly Val Ser Leu Leu Asn Ile Val Val Phe Trp Ala Leu Pro Ala
            155                 160                 165 ctg atc gcg ctg gcg cag ctg ttc gtc ttc ggc acc ttc ctg ccg cat       580
Leu Ile Ala Leu Ala Gln Leu Phe Val Phe Gly Thr Phe Leu Pro His
        170                 175                 180 cgc cac ggc gac acg ccg ttc gcg gac gcg cac aat gcc cgc agc aac       628
Arg His Gly Asp Thr Pro Phe Ala Asp Ala His Asn Ala Arg Ser Asn
    185                 190                 195 ggc tgg cca cag ctg gtg tcg ctg gcg acc tgc ttc cac ttc ggc gcc       676
Gly Trp Pro Gln Leu Val Ser Leu Ala Thr Cys Phe His Phe Gly Ala
200                 205                 210                 215 tat cat cac gaa cat cac ctg agc ccg tgg acg ccc tgg tgg cag ttg       724
Tyr His His Glu His His Leu Ser Pro Trp Thr Pro Trp Trp Gln Leu
                220                 225                 230 ccg cgc gtc ggc cag cct gcc gcc gga cac cgg tcg tta agc aaa gac       772
Pro Arg Val Gly Gln Pro Ala Ala Gly His Arg Ser Leu Ser Lys Asp
            235                 240                 245 cgg tag actagtaagg gcgaattc                                           796
Arg
```

-continued

<210> SEQ ID NO 66
<211> LENGTH: 248
<212> TYPE: PRT
<213> ORGANISM: Sphingomonas melonis DC18

<400> SEQUENCE: 66

Met Thr Val Asp His Asp Ala Arg Ile Ser Leu Leu Leu Ala Ala Ala
1               5                   10                  15

Ile Gly Ala Ala Trp Leu Ala Ile His Val Gly Ala Ile Val Trp Trp
            20                  25                  30

Arg Trp Ser Pro Ala Thr Ala Val Leu Ala Ile Pro Val Val Leu Val
        35                  40                  45

Gln Ala Trp Leu Ser Thr Gly Leu Phe Ile Val Ala His Asp Cys Met
    50                  55                  60

His Gly Ser Phe Val Pro Gly Arg Pro Ala Val Asn Arg Thr Val Gly
65                  70                  75                  80

Thr Leu Cys Leu Gly Ala Tyr Ala Gly Leu Ser Tyr Gly Gln Leu His
                85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125

Phe Phe Thr Ser Tyr Tyr Thr His Gly Gln Ile Leu Arg Ile Thr Ala
    130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Ala His Asn Ala Arg Ser Asn Gly Trp Pro Gln Leu Val Ser Leu Ala
        195                 200                 205

Thr Cys Phe His Phe Gly Ala Tyr His His Glu His His Leu Ser Pro
    210                 215                 220

Trp Thr Pro Trp Trp Gln Leu Pro Arg Val Gly Gln Pro Ala Ala Gly
225                 230                 235                 240

His Arg Ser Leu Ser Lys Asp Arg
                245

<210> SEQ ID NO 67
<211> LENGTH: 796
<212> TYPE: DNA
<213> ORGANISM: Sphingomonas melonis DC18
<220> FEATURE:
<221> NAME/KEY: CDS
<222> LOCATION: (32)..(778)

<400> SEQUENCE: 67
ccatggccct ttctagaaag gaggaataaa c atg acc gtc gat cac gac gca      52
                                   Met Thr Val Asp His Asp Ala
                                   1               5 cgg atc agc ctg ctg ctg gcc gca gcc atc ggc gcc gcg tgg ctg gcg    100
Arg Ile Ser Leu Leu Leu Ala Ala Ala Ile Gly Ala Ala Trp Leu Ala
        10                  15                  20 atc cat gtc ggg gcg atc gtg tgg tgg cga tgg agc ccg gcg acg gcg    148
Ile His Val Gly Ala Ile Val Trp Trp Arg Trp Ser Pro Ala Thr Ala
    25                  30                  35 gtg ctc gcg atc ccc gtc gtg ctc gta cag gcg tgg ctg agc acc gga    196

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Val | Leu | Ala | Ile | Pro | Val | Val | Leu | Val | Gln | Ala | Trp | Leu | Ser | Thr | Gly | |
| 40  |     |     |     | 45  |     |     |     |     | 50  |     |     |     |     | 55  |     |     |

```
ctg ttc atc gtc gcg cac gat tgc atg cac gga tcg ttc gtg ccc ggc      244
Leu Phe Ile Val Ala His Asp Cys Met His Gly Ser Phe Val Pro Gly
                    60              65                  70 cgg ccc gcg gtc aac cgg acc gtc ggg acg ctg tgc ctc ggc gcc tat      292
Arg Pro Ala Val Asn Arg Thr Val Gly Thr Leu Cys Leu Gly Ala Tyr
            75              80                  85 gcg gga ctg tcc tat ggc cag ctc cat ccc aag cat cat gcg cat cac      340
Ala Gly Leu Ser Tyr Gly Gln Leu His Pro Lys His His Ala His His
        90              95                  100 gat gcg ccg ggc acc gcc gcc gac ccc gat ttc cat gcc ggc gcg ccg      388
Asp Ala Pro Gly Thr Ala Ala Asp Pro Asp Phe His Ala Gly Ala Pro
    105                 110                 115 cga tcc gca ctg ccg tgg ttc gcg cgc ttc ttc acc agc tat tac acg      436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gtg ctg tac atg ctg      484
His Gly Gln Ile Leu Arg Ile Thr Ala Ala Ala Val Leu Tyr Met Leu
                140                 145                 150 ctc ggt gtg tcg ctg ctc aac atc gtc gtg ttc tgg gcg ttg ccg gcg      532
Leu Gly Val Ser Leu Leu Asn Ile Val Val Phe Trp Ala Leu Pro Ala
            155                 160                 165 ctg atc gcg ctg gcg cag ctg ttc gtc ttc ggc acc ttc ctg ccg cat      580
Leu Ile Ala Leu Ala Gln Leu Phe Val Phe Gly Thr Phe Leu Pro His
        170                 175                 180 cgc cac ggc gac acg ccg ttc gcg gac gcg cac aat gcc cgc agc aac      628
Arg His Gly Asp Thr Pro Phe Ala Asp Ala His Asn Ala Arg Ser Asn
185                 190                 195 ggc tgg cca cgg ctg gcg tcg ctg gtg acc tgc ttc cac ttc ggc gcc      676
Gly Trp Pro Arg Leu Ala Ser Leu Val Thr Cys Phe His Phe Gly Ala
200                 205                 210                 215 tat cat cac gaa cat cac ctg agc ccg tgg acg ccc tgg tgg cag ttg      724
Tyr His His Glu His His Leu Ser Pro Trp Thr Pro Trp Trp Gln Leu
                220                 225                 230 ccg cgc gtc ggc cag cct gcc gcc gga cac cgg tcg tta agc aaa gac      772
Pro Arg Val Gly Gln Pro Ala Ala Gly His Arg Ser Leu Ser Lys Asp
            235                 240                 245 cgg tag actagtaagg gcgaattc                                         796
Arg
```

<210> SEQ ID NO 68
<211> LENGTH: 248
<212> TYPE: PRT
<213> ORGANISM: Sphingomonas melonis DC18

<400> SEQUENCE: 68

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Thr | Val | Asp | His | Asp | Ala | Arg | Ile | Ser | Leu | Leu | Ala | Ala | Ala | |
| 1   |     |     |     | 5   |     |     |     |     | 10  |     |     |     |     | 15  |     |
|     |     |     |     |     |     |     |     |     |     |     |     |     |     |     |     |
| Ile | Gly | Ala | Ala | Trp | Leu | Ala | Ile | His | Val | Gly | Ala | Ile | Val | Trp | Trp |
|     |     |     | 20  |     |     |     |     | 25  |     |     |     |     | 30  |     |     |
|     |     |     |     |     |     |     |     |     |     |     |     |     |     |     |     |
| Arg | Trp | Ser | Pro | Ala | Thr | Ala | Val | Leu | Ala | Ile | Pro | Val | Val | Leu | Val |
|     |     |     | 35  |     |     |     |     | 40  |     |     |     |     | 45  |     |     |
|     |     |     |     |     |     |     |     |     |     |     |     |     |     |     |     |
| Gln | Ala | Trp | Leu | Ser | Thr | Gly | Leu | Phe | Ile | Val | Ala | His | Asp | Cys | Met |
|     |     |     | 50  |     |     |     |     | 55  |     |     |     |     | 60  |     |     |
|     |     |     |     |     |     |     |     |     |     |     |     |     |     |     |     |
| His | Gly | Ser | Phe | Val | Pro | Gly | Arg | Pro | Ala | Val | Asn | Arg | Thr | Val | Gly |
| 65  |     |     |     |     | 70  |     |     |     |     | 75  |     |     |     |     | 80  |
|     |     |     |     |     |     |     |     |     |     |     |     |     |     |     |     |
| Thr | Leu | Cys | Leu | Gly | Ala | Tyr | Ala | Gly | Leu | Ser | Tyr | Gly | Gln | Leu | His |
|     |     |     |     | 85  |     |     |     |     | 90  |     |     |     |     | 95  |     |

```
Pro Lys His His Ala His His Asp Ala Pro Gly Thr Ala Ala Asp Pro
            100                 105                 110
Asp Phe His Ala Gly Ala Pro Arg Ser Ala Leu Pro Trp Phe Ala Arg
        115                 120                 125
Phe Phe Thr Ser Tyr Tyr Thr His Gly Gln Ile Leu Arg Ile Thr Ala
    130                 135                 140
Ala Ala Val Leu Tyr Met Leu Gly Val Ser Leu Leu Asn Ile Val
145                 150                 155                 160
Val Phe Trp Ala Leu Pro Ala Leu Ile Ala Leu Ala Gln Leu Phe Val
                165                 170                 175
Phe Gly Thr Phe Leu Pro His Arg His Gly Asp Thr Pro Phe Ala Asp
            180                 185                 190
Ala His Asn Ala Arg Ser Asn Gly Trp Pro Arg Leu Ala Ser Leu Val
        195                 200                 205
Thr Cys Phe His Phe Gly Ala Tyr His His Glu His His Leu Ser Pro
    210                 215                 220
Trp Thr Pro Trp Trp Gln Leu Pro Arg Val Gly Gln Pro Ala Ala Gly
225                 230                 235                 240
His Arg Ser Leu Ser Lys Asp Arg
                245

<210> SEQ ID NO 69
<211> LENGTH: 796
<212> TYPE: DNA
<213> ORGANISM: Sphingomonas melonis DC18
<220> FEATURE:
<221> NAME/KEY: CDS
<222> LOCATION: (32)..(778)

<400> SEQUENCE: 69
ccatggccct ttctagaaag gaggaataaa c atg acc gtc gat cac gac gca        52
                                   Met Thr Val Asp His Asp Ala
                                   1               5 cgg gtc agc ctg ctg ctg gcc gca gcc atc ggc gcc gcg tgg ctg gcg     100
Arg Val Ser Leu Leu Leu Ala Ala Ala Ile Gly Ala Ala Trp Leu Ala
        10                  15                  20 atc cat gtc ggg gcg atc gtg tgg tgg cga tgg agc ccg gcg acg gcg     148
Ile His Val Gly Ala Ile Val Trp Trp Arg Trp Ser Pro Ala Thr Ala
 25                  30                  35 gtg ctc gcg atc ccc gtc gtg ctc gta cag gcg tgg ctg agc acc gga     196
Val Leu Ala Ile Pro Val Val Leu Val Gln Ala Trp Leu Ser Thr Gly
40                  45                  50                  55 ctg ttc atc gtc gcg cac gat tgc atg cac gga tcg ttc gtg ccc ggc     244
Leu Phe Ile Val Ala His Asp Cys Met His Gly Ser Phe Val Pro Gly
                60                  65                  70 cgg ccc gcg gtc aac cgg acc gtc ggg acg ctg tgc ctc ggc gcc tat     292
Arg Pro Ala Val Asn Arg Thr Val Gly Thr Leu Cys Leu Gly Ala Tyr
            75                  80                  85 gcg gga ctg tcc tat ggc cag ctc cat ccc aag cat cat gcg cat cac     340
Ala Gly Leu Ser Tyr Gly Gln Leu His Pro Lys His His Ala His His
        90                  95                  100 gat gcg ccg ggc acc gcc gcc gac ccc gat ttc cat gcc ggc gcg ccg     388
Asp Ala Pro Gly Thr Ala Ala Asp Pro Asp Phe His Ala Gly Ala Pro
    105                 110                 115 cga tcc gca ctg ccg tgg ttc gcg cgc ttc ttc acc agc tat tac acg     436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gtg ctg tac atg ctg     484
```

```
                His Gly Gln Ile Leu Arg Ile Thr Ala Ala Ala Val Leu Tyr Met Leu
                                140                 145                 150 ctc ggt gtg tcg ctg ctc aac atc gtc gtg ttc tgg gcg ttg ccg gcg      532
Leu Gly Val Ser Leu Leu Asn Ile Val Val Phe Trp Ala Leu Pro Ala
                155                 160                 165 ctg atc gcg ctg gcg cag ctg ttc gtc ttc ggc acc ttc ctg ccg cat      580
Leu Ile Ala Leu Ala Gln Leu Phe Val Phe Gly Thr Phe Leu Pro His
        170                 175                 180 cgc cac ggc gac acg ccg ttc gcg gac gcg cac aat gcc cgc agc aac      628
Arg His Gly Asp Thr Pro Phe Ala Asp Ala His Asn Ala Arg Ser Asn
    185                 190                 195 ggc tgg cca cgg ctg gcg tcg ctg gtg acc tgc ttc cac ttc ggc gcc      676
Gly Trp Pro Arg Leu Ala Ser Leu Val Thr Cys Phe His Phe Gly Ala
200                 205                 210                 215 tat cat cac gaa cat cac ctg agc ccg tgg acg ccc tgg tgg cag ttg      724
Tyr His His Glu His His Leu Ser Pro Trp Thr Pro Trp Trp Gln Leu
                220                 225                 230 ccg cgc gtc ggc cag cct gcc gcc gga cac cgg tcg tta agc aaa gac      772
Pro Arg Val Gly Gln Pro Ala Ala Gly His Arg Ser Leu Ser Lys Asp
                235                 240                 245 cgg tag actagtaagg gcgaattc                                          796
Arg

<210> SEQ ID NO 70
<211> LENGTH: 248
<212> TYPE: PRT
<213> ORGANISM: Sphingomonas melonis DC18

<400> SEQUENCE: 70

Met Thr Val Asp His Asp Ala Arg Val Ser Leu Leu Ala Ala Ala
1               5                   10                  15

Ile Gly Ala Ala Trp Leu Ala Ile His Val Gly Ala Ile Val Trp Trp
            20                  25                  30

Arg Trp Ser Pro Ala Thr Ala Val Leu Ala Ile Pro Val Leu Val
        35                  40                  45

Gln Ala Trp Leu Ser Thr Gly Leu Phe Ile Val Ala His Asp Cys Met
    50                  55                  60

His Gly Ser Phe Val Pro Gly Arg Pro Ala Val Asn Arg Thr Val Gly
65                  70                  75                  80

Thr Leu Cys Leu Gly Ala Tyr Ala Gly Leu Ser Tyr Gly Gln Leu His
                85                  90                  95

Pro Lys His His Ala His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125

Phe Phe Thr Ser Tyr Tyr Thr His Gly Gln Ile Leu Arg Ile Thr Ala
    130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Ala His Asn Ala Arg Ser Asn Gly Trp Pro Arg Leu Ala Ser Leu Val
        195                 200                 205

Thr Cys Phe His Phe Gly Ala Tyr His His Glu His His Leu Ser Pro
    210                 215                 220
```

```
Trp Thr Pro Trp Trp Gln Leu Pro Arg Val Gly Gln Pro Ala Ala Gly
225                 230                 235                 240

His Arg Ser Leu Ser Lys Asp Arg
                245

<210> SEQ ID NO 71
<211> LENGTH: 796
<212> TYPE: DNA
<213> ORGANISM: Spingomonas melonis DC18
<220> FEATURE:
<221> NAME/KEY: CDS
<222> LOCATION: (32)..(778)

<400> SEQUENCE: 71
ccatggccct ttctagaaag gaggaacaaa c atg acc gtc gat cac gac gca         52
                                   Met Thr Val Asp His Asp Ala
                                   1               5 cgg atc agc ctg ctg ctg gcc gca gcc atc ggc gcc gcg tgg ctg gcg       100
Arg Ile Ser Leu Leu Leu Ala Ala Ala Ile Gly Ala Ala Trp Leu Ala
         10                  15                  20 atc cat gtc ggg gcg atc gtg tgg tgg cga tgg agc ccg gcg acg gcg       148
Ile His Val Gly Ala Ile Val Trp Trp Arg Trp Ser Pro Ala Thr Ala
     25                  30                  35 gtg ctc gcg atc ccc gtc gtg ctc gta cag gcg tgg ctg agc acc ggt       196
Val Leu Ala Ile Pro Val Val Leu Val Gln Ala Trp Leu Ser Thr Gly
40                  45                  50                  55 ctg ttc atc gtc gcg cac gat tgc atg cac gga tcg ttc gtg ccc ggc       244
Leu Phe Ile Val Ala His Asp Cys Met His Gly Ser Phe Val Pro Gly
             60                  65                  70 cgg ccc gcg gtc aac cgg acc gtc ggg acg ctg tgc ctc ggc gcc tat       292
Arg Pro Ala Val Asn Arg Thr Val Gly Thr Leu Cys Leu Gly Ala Tyr
         75                  80                  85 gcg gga ctg tcc tat ggc cag ctc ctt ccc aag cat cat gcg cat cac       340
Ala Gly Leu Ser Tyr Gly Gln Leu Leu Pro Lys His His Ala His His
     90                  95                 100 gat gcg ccg ggc acc gcc gcc gac ccc gat ttc cat gcc ggc gcg ccg       388
Asp Ala Pro Gly Thr Ala Ala Asp Pro Asp Phe His Ala Gly Ala Pro
105                 110                 115 cga tcc gca ctg ccg tgg ttc gcg cgc ttc ttc acc agc tat tac acg       436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gtg ctg tac atg ctg       484
His Gly Gln Ile Leu Arg Ile Thr Ala Ala Ala Val Leu Tyr Met Leu
             140                 145                 150 ctc ggt gtg tcg ctg ctc aac atc gtc gtg ttc tgg gcg ttg ccg gcg       532
Leu Gly Val Ser Leu Leu Asn Ile Val Val Phe Trp Ala Leu Pro Ala
         155                 160                 165 ctg atc gcg ctg gcg cag ctg ttc gtc ttc ggc acc ttc ctg ccg cat       580
Leu Ile Ala Leu Ala Gln Leu Phe Val Phe Gly Thr Phe Leu Pro His
     170                 175                 180 cgc cac ggc gac acg ccg ttc gcg gac gcg cac aat gcc cgc agc aac       628
Arg His Gly Asp Thr Pro Phe Ala Asp Ala His Asn Ala Arg Ser Asn
185                 190                 195 ggc tgg cca cgg ctg gcg tcg ctg gcg acc tgc ttc cac ttc ggc gcc       676
Gly Trp Pro Arg Leu Ala Ser Leu Ala Thr Cys Phe His Phe Gly Ala
200                 205                 210                 215 tat cat cac gaa cat cac ctg agc ccg tgg acg ccc tgg tgg cag ttg       724
Tyr His His Glu His His Leu Ser Pro Trp Thr Pro Trp Trp Gln Leu
             220                 225                 230 ccg cgc gtc ggc cag cct gcc gcc gga cac cgg tcg tta agc aaa gac       772
Pro Arg Val Gly Gln Pro Ala Ala Gly His Arg Ser Leu Ser Lys Asp
```

```
Pro Arg Val Gly Gln Pro Ala Ala Gly His Arg Ser Leu Ser Lys Asp
            235                 240                 245 cgg tag actagtaagg gcgaattc                                          796
Arg

<210> SEQ ID NO 72
<211> LENGTH: 248
<212> TYPE: PRT
<213> ORGANISM: Spingomonas melonis DC18

<400> SEQUENCE: 72

Met Thr Val Asp His Asp Ala Arg Ile Ser Leu Leu Leu Ala Ala Ala
1               5                   10                  15

Ile Gly Ala Ala Trp Leu Ala Ile His Val Gly Ala Ile Val Trp Trp
            20                  25                  30

Arg Trp Ser Pro Ala Thr Ala Val Leu Ala Ile Pro Val Val Leu Val
        35                  40                  45

Gln Ala Trp Leu Ser Thr Gly Leu Phe Ile Val Ala His Asp Cys Met
    50                  55                  60

His Gly Ser Phe Val Pro Gly Arg Pro Ala Val Asn Arg Thr Val Gly
65                  70                  75                  80

Thr Leu Cys Leu Gly Ala Tyr Ala Gly Leu Ser Tyr Gly Gln Leu Leu
                85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125

Phe Phe Thr Ser Tyr Tyr Thr His Gly Gln Ile Leu Arg Ile Thr Ala
    130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Ala His Asn Ala Arg Ser Asn Gly Trp Pro Arg Leu Ala Ser Leu Ala
        195                 200                 205

Thr Cys Phe His Phe Gly Ala Tyr His His Glu His His Leu Ser Pro
    210                 215                 220

Trp Thr Pro Trp Trp Gln Leu Pro Arg Val Gly Gln Pro Ala Ala Gly
225                 230                 235                 240

His Arg Ser Leu Ser Lys Asp Arg
                245

<210> SEQ ID NO 73
<211> LENGTH: 796
<212> TYPE: DNA
<213> ORGANISM: Spingomonas melonis DC18
<220> FEATURE:
<221> NAME/KEY: CDS
<222> LOCATION: (32)..(778)

<400> SEQUENCE: 73
ccatggccct ttctagaaag gaggaataaa c atg acc gtc gat cac gac gca      52
                                   Met Thr Val Asp His Asp Ala
                                   1               5 cgg atc agc ctg ctg ctg gcc gca gcc atc ggc gcc gcg tgg ctg gcg   100
Arg Ile Ser Leu Leu Leu Ala Ala Ala Ile Gly Ala Ala Trp Leu Ala
```

```
               10                  15                  20
atc cat gtc ggg gcg atc gtg tgg tgg cga tgg agc ccg gcg acg gcg    148
Ile His Val Gly Ala Ile Val Trp Trp Arg Trp Ser Pro Ala Thr Ala
     25                  30                  35 gtg ctc gcg atc ccc gtc gtg ctc gta cag gcg tgg ctg agc acc ggc    196
Val Leu Ala Ile Pro Val Val Leu Val Gln Ala Trp Leu Ser Thr Gly
 40                  45                  50                  55 ctg ttc atc gtc gcg cac gat tgc atg cac gga tcg ttc gtg ccc ggc    244
Leu Phe Ile Val Ala His Asp Cys Met His Gly Ser Phe Val Pro Gly
                     60                  65                  70 cgg ccc gcg gtc aac cgg acc gtc ggg acg ctg tgc ctc ggc gcc tat    292
Arg Pro Ala Val Asn Arg Thr Val Gly Thr Leu Cys Leu Gly Ala Tyr
             75                  80                  85 gcg gga ctg tcc tat ggc cag ctc ctt ccc aag cat cat gcg cat cac    340
Ala Gly Leu Ser Tyr Gly Gln Leu Leu Pro Lys His His Ala His His
         90                  95                 100 gat gcg ccg ggc acc gcc gcc gac ccc gat ttc cat gcc ggc gcg ccg    388
Asp Ala Pro Gly Thr Ala Ala Asp Pro Asp Phe His Ala Gly Ala Pro
    105                 110                 115 cga tcc gca ctg ccg tgg ttc gcg cgc ttc ttc acc agc tat tac acg    436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gtg ctg tac atg ttg    484
His Gly Gln Ile Leu Arg Ile Thr Ala Ala Ala Val Leu Tyr Met Leu
                140                 145                 150 ctc ggt gtg tcg ctg ctc aac atc gtc gtg ttc tgg gcg ttg ccg gcg    532
Leu Gly Val Ser Leu Leu Asn Ile Val Val Phe Trp Ala Leu Pro Ala
            155                 160                 165 ctg atc gcg ctg gcg cag ctg ttc gtc ttc ggc acc ttc ctg ccg cat    580
Leu Ile Ala Leu Ala Gln Leu Phe Val Phe Gly Thr Phe Leu Pro His
        170                 175                 180 cgc cac ggc gac acg ccg ttc gcg gac gag cac aat gcc cgc agc aac    628
Arg His Gly Asp Thr Pro Phe Ala Asp Glu His Asn Ala Arg Ser Asn
    185                 190                 195 ggc tgg cca cgg ctg gcg tcg ctg gcg acc tgc ttc cac ttc ggc gcc    676
Gly Trp Pro Arg Leu Ala Ser Leu Ala Thr Cys Phe His Phe Gly Ala
200                 205                 210                 215 tat cat cac gaa cat cac ctg agc ccg tgg acg ccc tgg tgg cag ttg    724
Tyr His His Glu His His Leu Ser Pro Trp Thr Pro Trp Trp Gln Leu
                220                 225                 230 ccg cgc gtc ggc cag cct gcc gcc gga cac cgg tcg tta agc aaa gac    772
Pro Arg Val Gly Gln Pro Ala Ala Gly His Arg Ser Leu Ser Lys Asp
            235                 240                 245 cgg tag actagtaagg gcgaattc                                        796
Arg

<210> SEQ ID NO 74
<211> LENGTH: 248
<212> TYPE: PRT
<213> ORGANISM: Spingomonas melonis DC18

<400> SEQUENCE: 74

Met Thr Val Asp His Asp Ala Arg Ile Ser Leu Leu Ala Ala Ala
1               5                   10                  15

Ile Gly Ala Ala Trp Leu Ala Ile His Val Gly Ala Ile Val Trp Trp
                20                  25                  30

Arg Trp Ser Pro Ala Thr Ala Val Leu Ala Ile Pro Val Val Leu Val
            35                  40                  45

Gln Ala Trp Leu Ser Thr Gly Leu Phe Ile Val Ala His Asp Cys Met
```

```
                50                  55                  60
His Gly Ser Phe Val Pro Gly Arg Pro Ala Val Asn Arg Thr Val Gly
 65                  70                  75                  80

Thr Leu Cys Leu Gly Ala Tyr Ala Gly Leu Ser Tyr Gly Gln Leu Leu
                 85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125

Phe Phe Thr Ser Tyr Tyr Thr His Gly Gln Ile Leu Arg Ile Thr Ala
    130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Glu His Asn Ala Arg Ser Asn Gly Trp Pro Arg Leu Ala Ser Leu Ala
        195                 200                 205

Thr Cys Phe His Phe Gly Ala Tyr His His Glu His His Leu Ser Pro
    210                 215                 220

Trp Thr Pro Trp Trp Gln Leu Pro Arg Val Gly Gln Pro Ala Ala Gly
225                 230                 235                 240

His Arg Ser Leu Ser Lys Asp Arg
                245

<210> SEQ ID NO 75
<211> LENGTH: 44
<212> TYPE: DNA
<213> ORGANISM: artificial sequence
<220> FEATURE:
<223> OTHER INFORMATION: primer

<400> SEQUENCE: 75
aatgcccgca gcaacggctg gccatggctg gcgtcgctgg cgac                    44

<210> SEQ ID NO 76
<211> LENGTH: 44
<212> TYPE: DNA
<213> ORGANISM: artificial sequence
<220> FEATURE:
<223> OTHER INFORMATION: primer

<400> SEQUENCE: 76
gtcgccagcg acgccagcca tggccagccg ttgctgcggg catt                    44

<210> SEQ ID NO 77
<211> LENGTH: 796
<212> TYPE: DNA
<213> ORGANISM: Sphingomonas melonis DC18
<220> FEATURE:
<221> NAME/KEY: CDS
<222> LOCATION: (32)..(778)

<400> SEQUENCE: 77
ccatggccct ttctagaaag gaggaataaa c atg acc gtc gat cac gac gca      52
                                  Met Thr Val Asp His Asp Ala
                                   1               5 cgg atc agc ctg ctg ctg gcc gca gcc atc ggc gcc gcg tgg ctg gcg    100
Arg Ile Ser Leu Leu Leu Ala Ala Ala Ile Gly Ala Ala Trp Leu Ala
```

```
                    10              15              20
atc cat gtc ggg gcg atc gtg tgg tgg cga tgg agc ccg gcg acg gcg      148
Ile His Val Gly Ala Ile Val Trp Trp Arg Trp Ser Pro Ala Thr Ala
     25                  30                  35 gtg ctc gcg atc ccc gtc gtg ctc gta cag gcg tgg ctg agc acc ggc      196
Val Leu Ala Ile Pro Val Val Leu Val Gln Ala Trp Leu Ser Thr Gly
 40                  45                  50                  55 ctg ttc atc gtc gcg cac gat tgc atg cac gga tcg ttc gtg ccc ggc      244
Leu Phe Ile Val Ala His Asp Cys Met His Gly Ser Phe Val Pro Gly
                     60                  65                  70 cgg ccc gcg gtc aac cgg acc gtc ggg acg ctg tgc ctc ggc gcc tat      292
Arg Pro Ala Val Asn Arg Thr Val Gly Thr Leu Cys Leu Gly Ala Tyr
                 75                  80                  85 gcg gga ctg tcc tat ggc cag ctc cat ccc aag cat cat gcg cat cac      340
Ala Gly Leu Ser Tyr Gly Gln Leu His Pro Lys His His Ala His His
             90                  95                 100 gat gcg ccg ggc acc gcc gcc gac ccc gat ttc cat gcc ggc gcg ccg      388
Asp Ala Pro Gly Thr Ala Ala Asp Pro Asp Phe His Ala Gly Ala Pro
        105                 110                 115 cga tcc gca ctg ccg tgg ttc gcg cgc ttc ttc acc agc tat tac acg      436
Arg Ser Ala Leu Pro Trp Phe Ala Arg Phe Phe Thr Ser Tyr Tyr Thr
120                 125                 130                 135 cac ggc cag atc ctc cgg atc acc gcg gcg gcg gtg ctg tac atg ctg      484
His Gly Gln Ile Leu Arg Ile Thr Ala Ala Ala Val Leu Tyr Met Leu
                140                 145                 150 ctc ggt gtg tcg ctg ctc aac atc gtc gtg ttc tgg gcg ttg ccg gcg      532
Leu Gly Val Ser Leu Leu Asn Ile Val Val Phe Trp Ala Leu Pro Ala
                155                 160                 165 ctg atc gcg ctg gcg cag ctg ttc gtc ttc ggc acc ttc ctg ccg cat      580
Leu Ile Ala Leu Ala Gln Leu Phe Val Phe Gly Thr Phe Leu Pro His
            170                 175                 180 cgc cac ggc gac acg ccg ttc gcg gac gcg cac aat gcc cgc agc aac      628
Arg His Gly Asp Thr Pro Phe Ala Asp Ala His Asn Ala Arg Ser Asn
        185                 190                 195 ggc tgg cca tgg ctg gcg tcg ctg gcg acc tgc ttc cac ttg ggc gcc      676
Gly Trp Pro Trp Leu Ala Ser Leu Ala Thr Cys Phe His Leu Gly Ala
200                 205                 210                 215 tat cat cac gaa cat cac ctg agc ccg tgg acg ccc tgg tgg cag ttg      724
Tyr His His Glu His His Leu Ser Pro Trp Thr Pro Trp Trp Gln Leu
                220                 225                 230 ccg cgc gtc ggc cag cct gcc gcc gga cac cgg tcg tta agc aaa gac      772
Pro Arg Val Gly Gln Pro Ala Ala Gly His Arg Ser Leu Ser Lys Asp
            235                 240                 245 cgg tag actagtaagg gcgaattc                                          796
Arg

<210> SEQ ID NO 78
<211> LENGTH: 248
<212> TYPE: PRT
<213> ORGANISM: Sphingomonas melonis DC18

<400> SEQUENCE: 78

Met Thr Val Asp His Asp Ala Arg Ile Ser Leu Leu Ala Ala Ala
 1               5                  10                  15

Ile Gly Ala Ala Trp Leu Ala Ile His Val Gly Ala Ile Val Trp Trp
                 20                  25                  30

Arg Trp Ser Pro Ala Thr Ala Val Leu Ala Ile Pro Val Val Leu Val
             35                  40                  45

Gln Ala Trp Leu Ser Thr Gly Leu Phe Ile Val Ala His Asp Cys Met
```

```
              50                  55                  60
His Gly Ser Phe Val Pro Gly Arg Pro Ala Val Asn Arg Thr Val Gly
 65                  70                  75                  80

Thr Leu Cys Leu Gly Ala Tyr Ala Gly Leu Ser Tyr Gly Gln Leu His
                 85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
            115                 120                 125

Phe Phe Thr Ser Tyr Tyr Thr His Gly Gln Ile Leu Arg Ile Thr Ala
        130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
                180                 185                 190

Ala His Asn Ala Arg Ser Asn Gly Trp Pro Trp Leu Ala Ser Leu Ala
            195                 200                 205

Thr Cys Phe His Leu Gly Ala Tyr His His Glu His His Leu Ser Pro
        210                 215                 220

Trp Thr Pro Trp Trp Gln Leu Pro Arg Val Gly Gln Pro Ala Ala Gly
225                 230                 235                 240

His Arg Ser Leu Ser Lys Asp Arg
                245

<210> SEQ ID NO 79
<211> LENGTH: 47
<212> TYPE: DNA
<213> ORGANISM: artificial sequence
<220> FEATURE:
<223> OTHER INFORMATION: primer

<400> SEQUENCE: 79 tggcccttte tagaaaggag gaattaacca tgaccgtcga tcacgac          47

<210> SEQ ID NO 80
<211> LENGTH: 47
<212> TYPE: DNA
<213> ORGANISM: artificial sequence
<220> FEATURE:
<223> OTHER INFORMATION: primer

<400> SEQUENCE: 80
gtcgtgatcg acggtcatgg ttaattcctc ctttctagaa agggcca          47

<210> SEQ ID NO 81
<211> LENGTH: 796
<212> TYPE: DNA
<213> ORGANISM: Sphingomonas melonis DC18

<400> SEQUENCE: 81
ccatggccct ttctagaaag gaggaattaa catgaccgtc gatcacgacg cacggatcag    60
cctgctgctg gccgcagcca tcggcgccgc gtggctggcg atccatgtcg ggcgatcgt   120
gtggtggcga tggagcccgg cgacggcggt gctcgcgatc ccgtcgtgc tcgtacaggc   180
gtggctgagc accggcctgt tcatcgtcgc gcacgattgc atgcacggat cgttcgtgcc   240
cggccggccc gcggtcaacc ggaccgtcgg gacgctgtgc ctcggcgcct atgcgggact   300
```

-continued

```
gtcctatggc cagctccatc ccaagcatca tgcgcatcac gatgcgccgg gcaccgccgc    360
cgaccccgat ttccatgccg gcgcgccgcg atccgcactg ccgtggttcg cgcgcttctt    420
caccagctat tacacgcacg gccagatcct ccggatcacc gcggcggcgg tgctgtacat    480
gctgctcggt gtgtcgctgc tcaacatcgt cgtgttctgg gcgttgccgg cgctgatcgc    540
gctggcgcag ctgttcgtct tcggcaccct cctgccgcat cgccacggcg acacgccgtt    600
cgcggacacg cacaacgccc gcagcaacgg ctggccatgg ctggcgtcgc tggcgacctg    660
cttccacttc ggcgcctatc atcacgaaca tcacctgagc ccgtggacgc cctggtggca    720
gttgccgcgc gtcggccagc ctgccgccgg acaccggtcg ttaagcaaag accggtagac    780
tagtaagggc gaattc                                                    796
```